(12) United States Patent
Rosenthal et al.

(10) Patent No.: US 12,171,654 B2
(45) Date of Patent: Dec. 24, 2024

(54) NASAL IMPLANTS AND METHODS OF USE

(71) Applicant: Spirox, Inc., Maple Grove, MN (US)

(72) Inventors: Michael H. Rosenthal, Redwood City, CA (US); Brian Domecus, Redwood City, CA (US); Piyush Arora, Redwood City, CA (US); Halil I. Karabey, Redwood City, CA (US); Gilbert Laroya, Redwood City, CA (US); Michael S. Mirizzi, Redwood City, CA (US); Scott J. Baron, Redwood City, CA (US)

(73) Assignee: Stryker Corporation, Portage, MI (US)

( * ) Notice: Subject to any disclaimer, the term of this patent is extended or adjusted under 35 U.S.C. 154(b) by 21 days.

(21) Appl. No.: 18/098,479

(22) Filed: Jan. 18, 2023

(65) Prior Publication Data
US 2023/0149156 A1    May 18, 2023

Related U.S. Application Data

(63) Continuation of application No. 16/474,952, filed as application No. PCT/US2017/068419 on Dec. 26, 2017, now Pat. No. 11,576,770.
(Continued)

(51) Int. Cl.
*A61F 2/18* (2006.01)
*A61F 5/08* (2006.01)
(Continued)

(52) U.S. Cl.
CPC .............. *A61F 2/186* (2013.01); *A61F 5/08* (2013.01); *A61L 27/58* (2013.01);
(Continued)

(58) Field of Classification Search
CPC .... A61F 2/18; A61F 2/186; A61F 5/08; A61F 2002/0081; A61F 2002/3093;
(Continued)

(56) References Cited

U.S. PATENT DOCUMENTS 7,780,730 B2   8/2010   Saidi
9,173,733 B1  11/2015   Lim et al.
(Continued)

FOREIGN PATENT DOCUMENTS

CN   202105048        1/2012
DE   203 07 058 U1    8/2003
(Continued)

OTHER PUBLICATIONS

English Translation of Abstract of Chinese Patent Application No. CN 202105048U dated Jul. 13, 2021.
(Continued)

*Primary Examiner* — Dinah Baria
(74) *Attorney, Agent, or Firm* — McDonnell Bohnen Hulbert & Berghoff LLP

(57) ABSTRACT

Described are implants for placing in a body, tools for delivering the implants, and systems and methods for using implants and tools for placing in a body and more particularly to nasal implants, tools for delivering nasal implants, and systems and methods for using such implants and tools.

20 Claims, 63 Drawing Sheets

Related U.S. Application Data

(60) Provisional application No. 62/440,920, filed on Dec. 30, 2016.

(51) Int. Cl.
*A61L 27/58* (2006.01)
*A61F 2/00* (2006.01)

(52) U.S. Cl.
CPC ............... *A61F 2002/0081* (2013.01); *A61F 2210/0004* (2013.01); *A61F 2220/0016* (2013.01); *A61F 2230/0091* (2013.01); *A61F 2250/0018* (2013.01); *A61F 2250/0039* (2013.01)

(58) Field of Classification Search
CPC ...... A61F 2210/0004; A61F 2250/0039; A61F 2250/0018; A61F 2220/0016; A61F 2230/0091; A61L 27/58
See application file for complete search history.

(56) References Cited

U.S. PATENT DOCUMENTS

| | | |
|---|---|---|
| 2007/0005094 A1 | 1/2007 | Eaton et al. |
| 2008/0015540 A1 | 1/2008 | Muni et al. |
| 2009/0312791 A1 | 12/2009 | Lindh, Sr. et al. |
| 2010/0100170 A1 | 4/2010 | Tan et al. |
| 2010/0249818 A1 | 9/2010 | Jinno et al. |
| 2011/0251634 A1 | 10/2011 | Gonzales et al. |
| 2013/0060348 A1* | 3/2013 | Hodgkinson ............ A61L 31/16 623/23.76 |
| 2014/0243975 A1 | 8/2014 | Saidi et al. |
| 2014/0288592 A1 | 9/2014 | Hussain et al. |
| 2015/0100133 A1 | 4/2015 | Xie et al. |
| 2015/0148902 A1 | 5/2015 | Komrit |
| 2016/0058556 A1 | 3/2016 | Rosenthal et al. |
| 2016/0287367 A1 | 10/2016 | Rontal |
| 2017/0105836 A1 | 4/2017 | Baron et al. |

FOREIGN PATENT DOCUMENTS

| | | |
|---|---|---|
| JP | 2010-227438 | 10/2010 |
| JP | 2015-533589 | 11/2015 |
| WO | 2006107957 | 10/2006 |
| WO | 2007134215 | 11/2007 |
| WO | 2015192162 | 12/2015 |
| WO | 2017053824 | 3/2017 |

OTHER PUBLICATIONS

International Search Report and the Written Opinion for PCT/US2017068419 dated Apr. 26, 2018 (13 pages).

\* cited by examiner

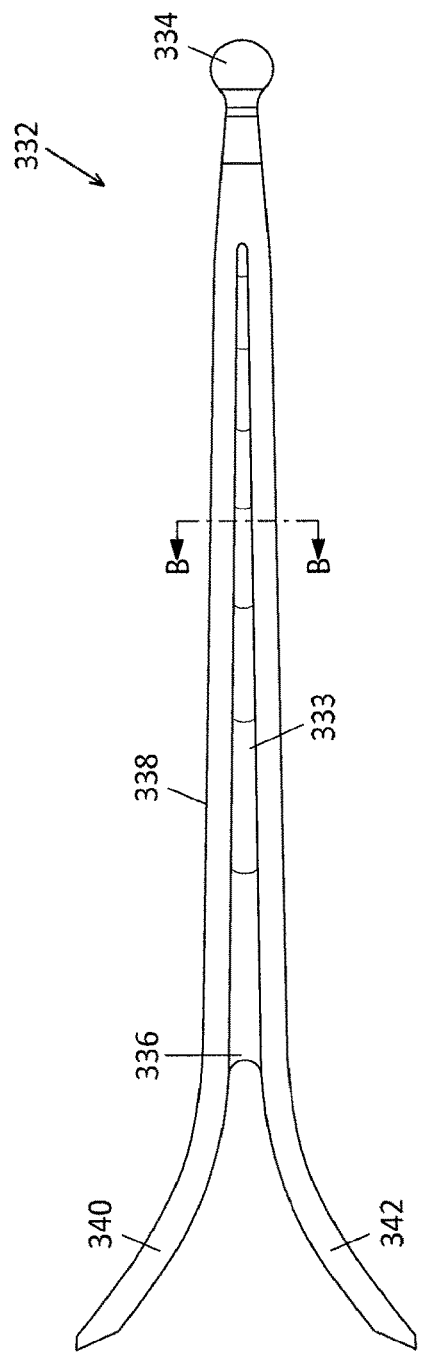
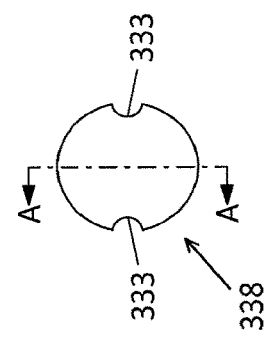
FIG. 3A
FIG. 3B $$I_x = \frac{b h^3}{12}$$

$$I_x = \frac{\pi r^4}{4}$$
$$= \frac{\pi d^4}{64}$$

$$I_x = \frac{\pi (d_o^4 - d_i^4)}{4}$$
$$= \frac{\pi (r_o^4 - r_i^4)}{64}$$

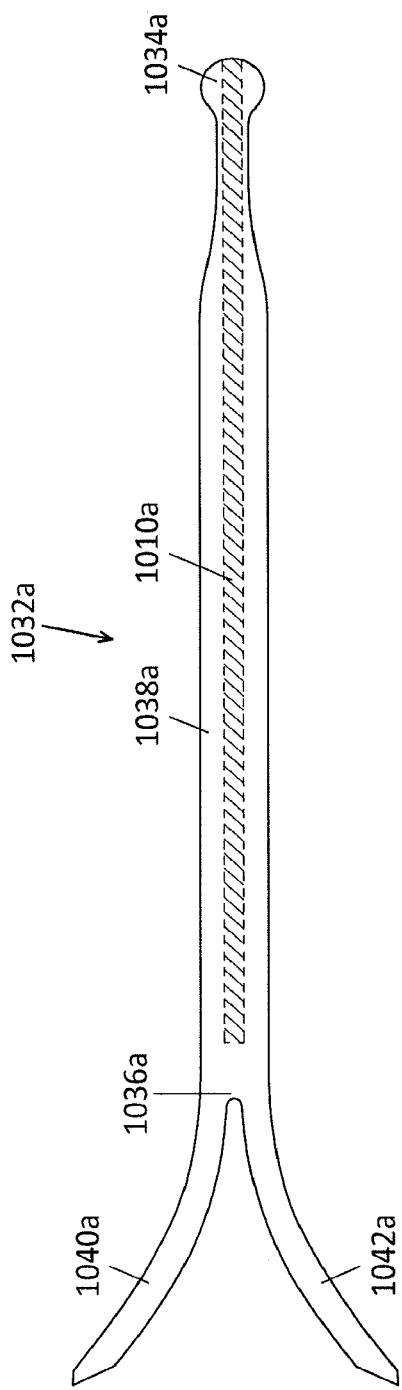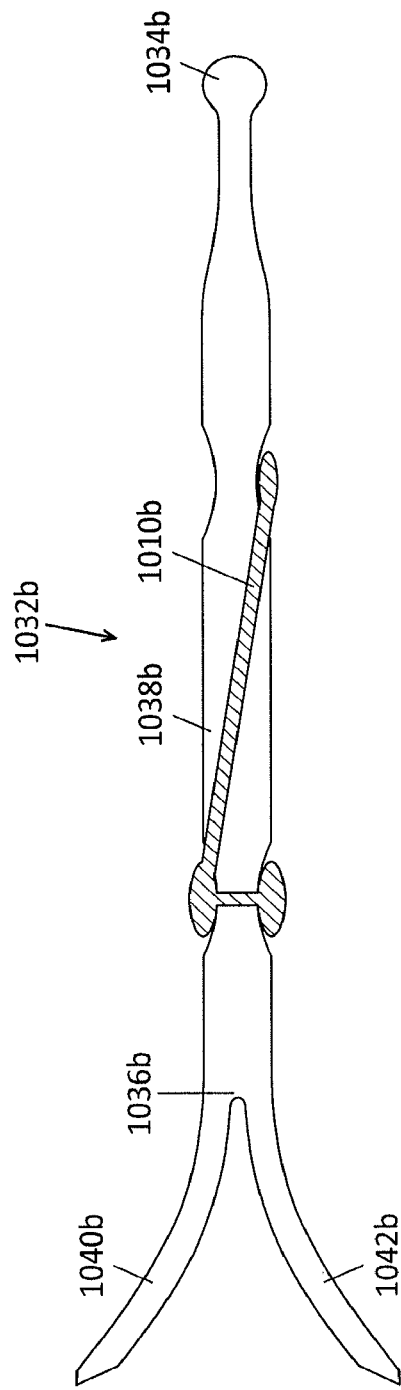
FIG. 10A
FIG. 10B

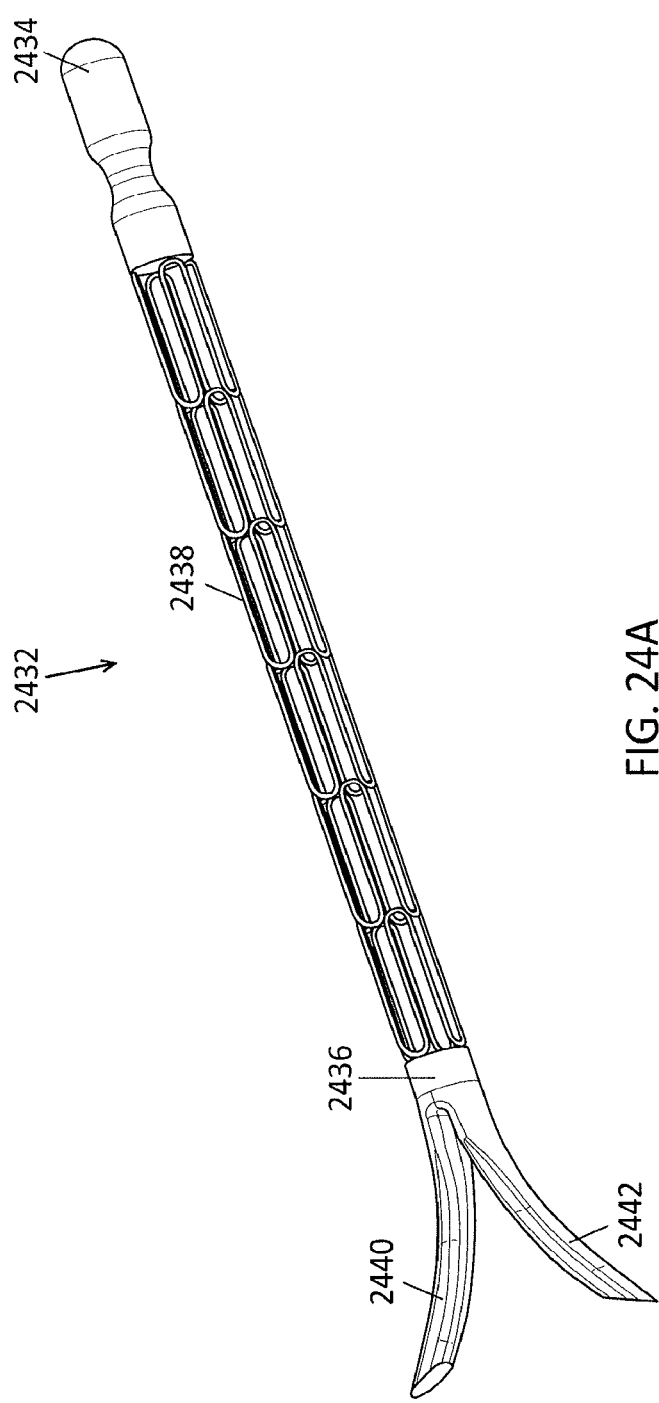
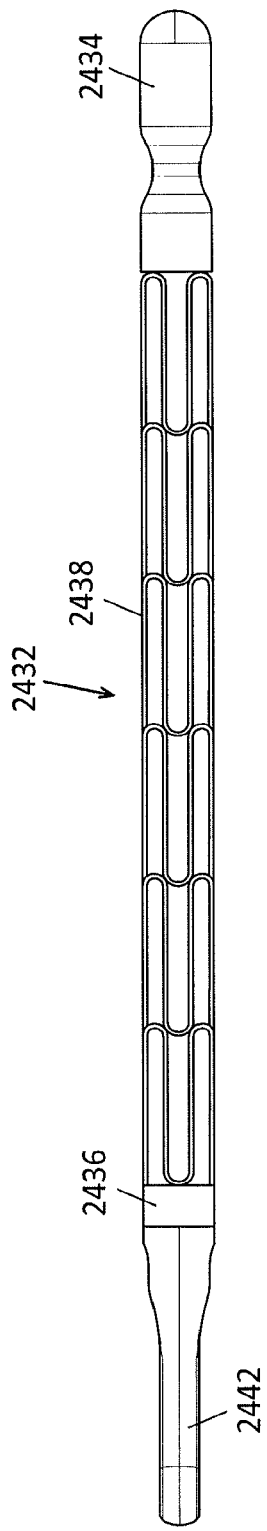
FIG. 24A
FIG. 24B

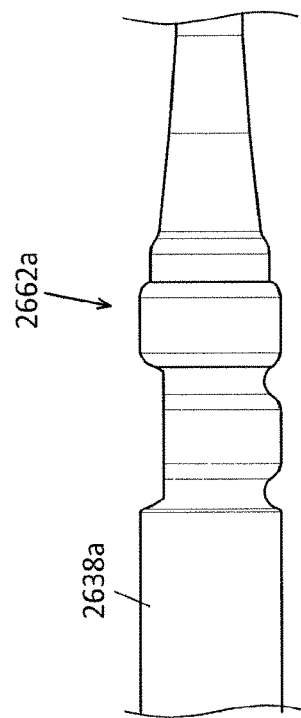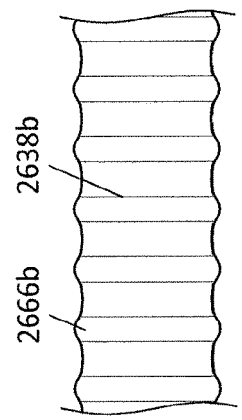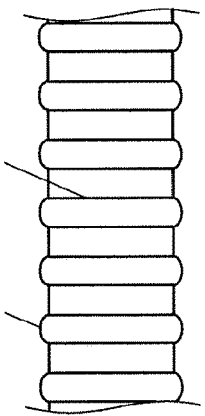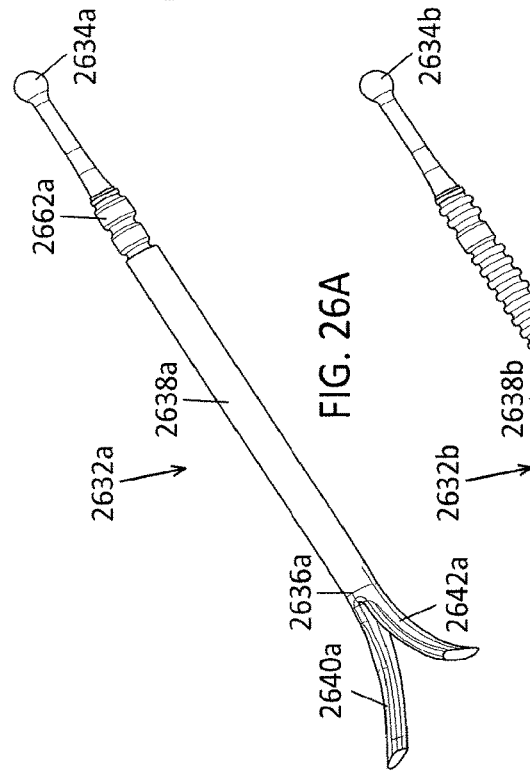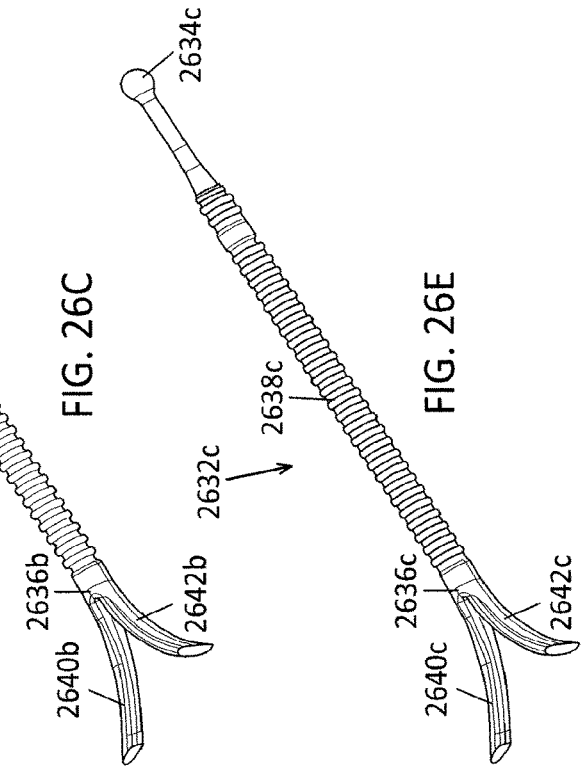

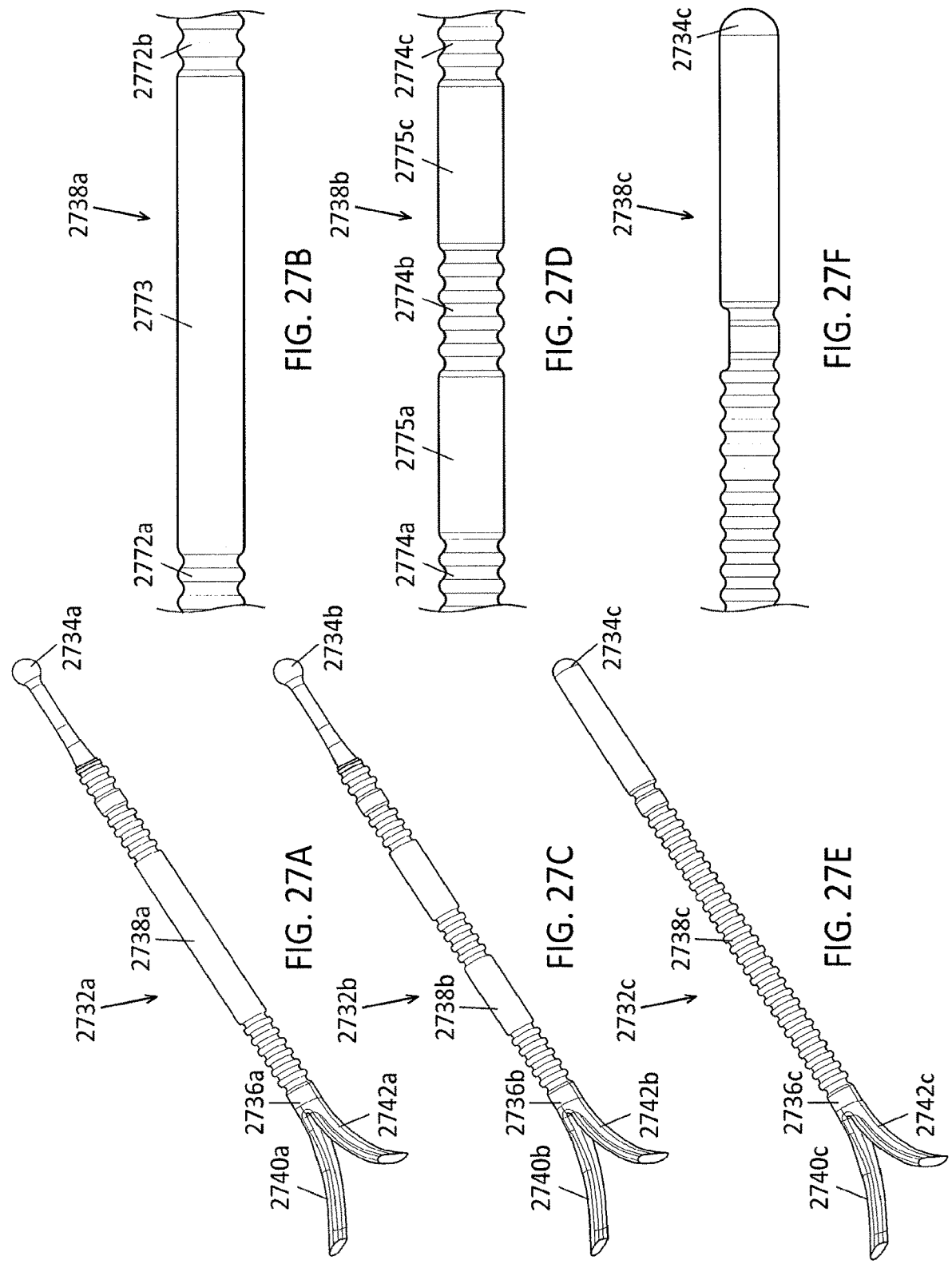

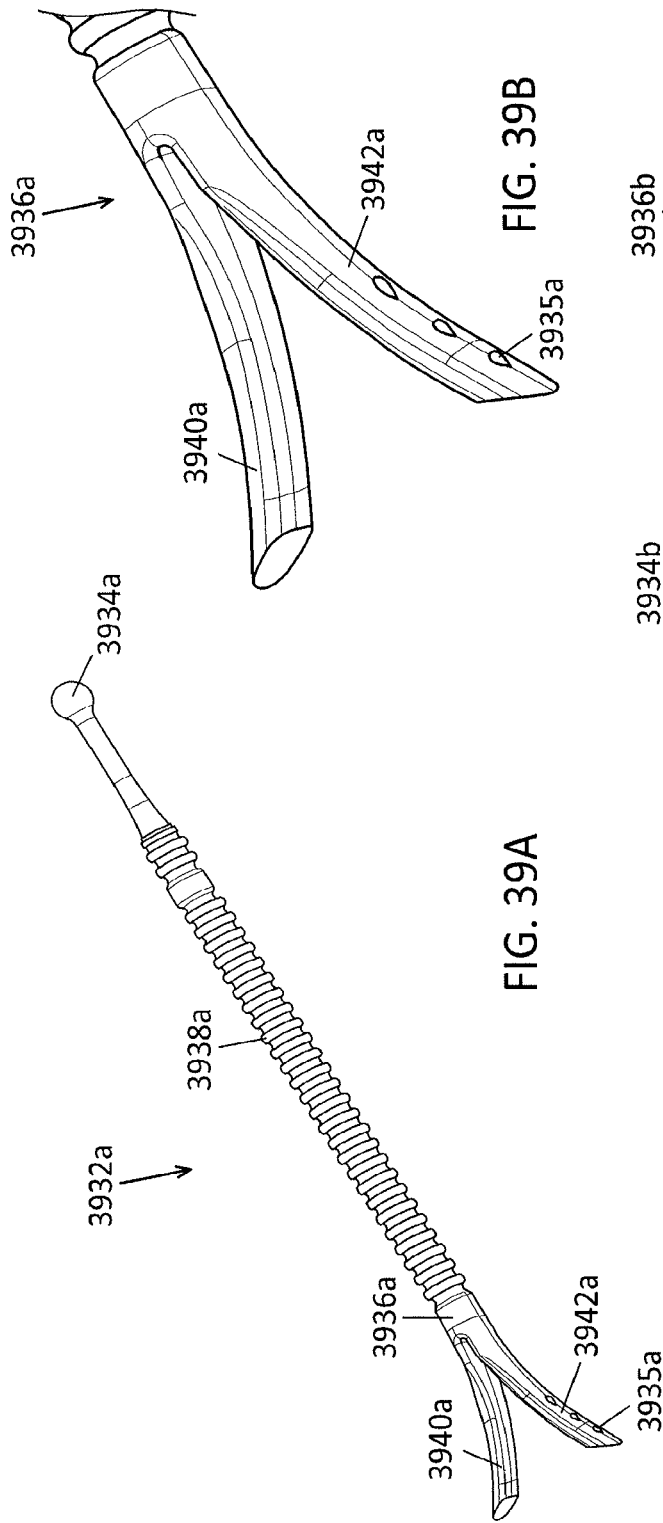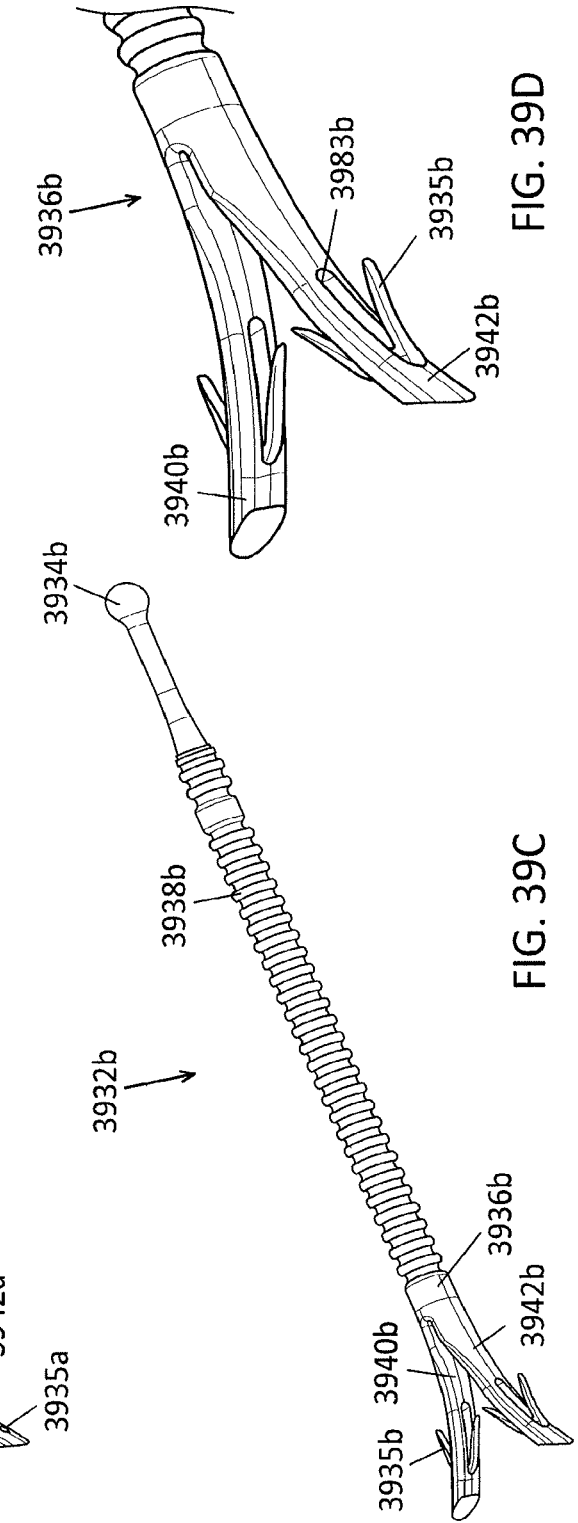

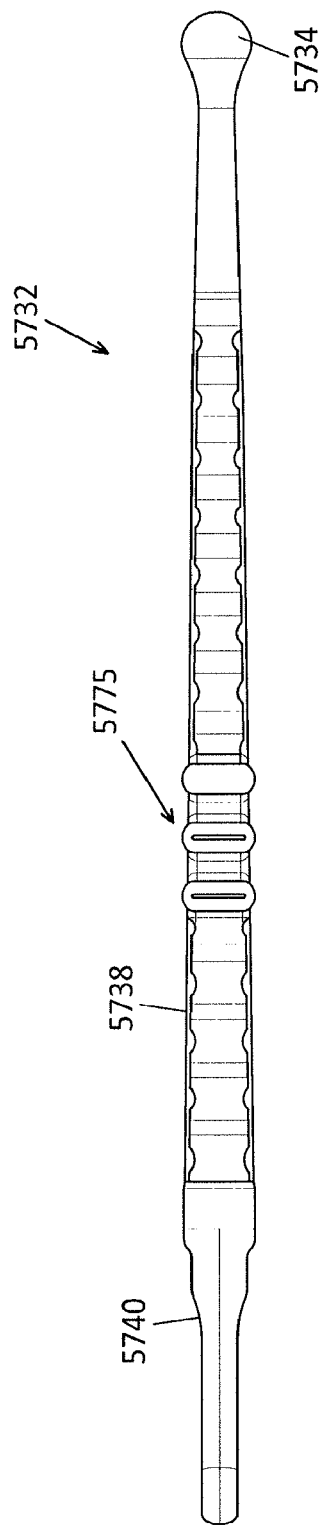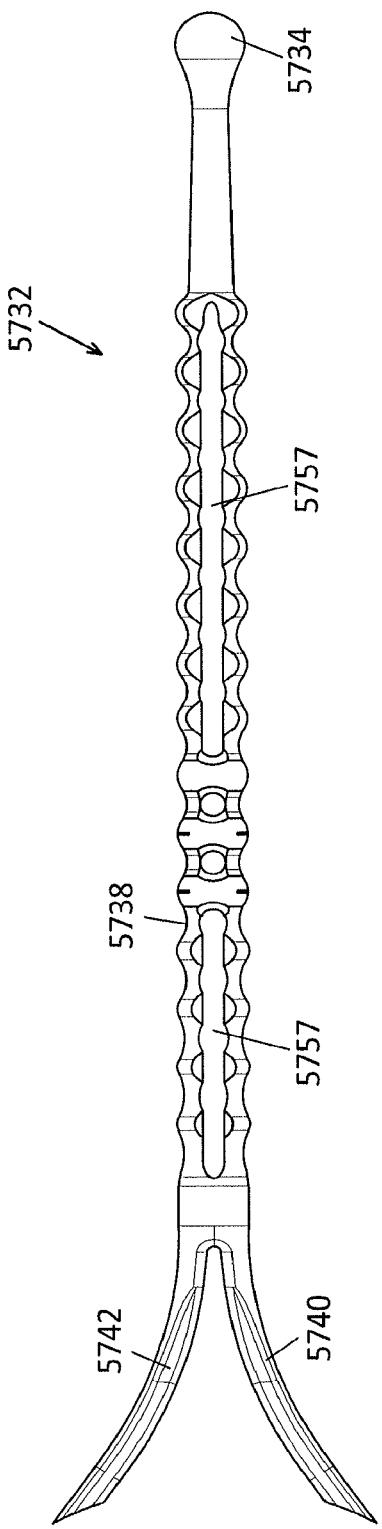
FIG. 57A
FIG. 57B

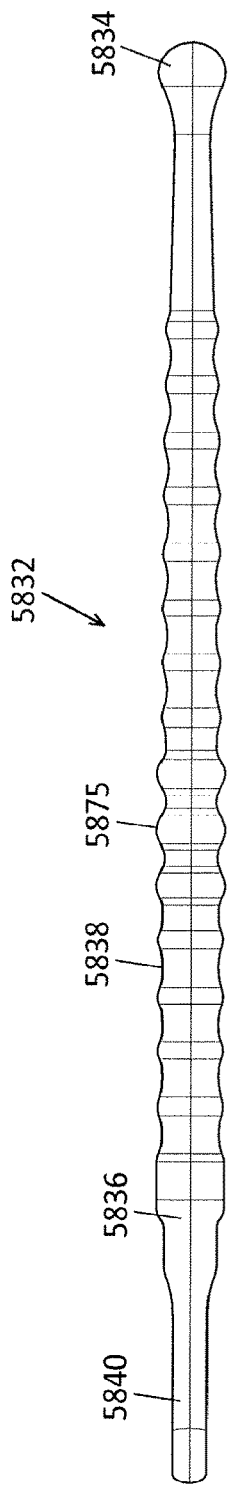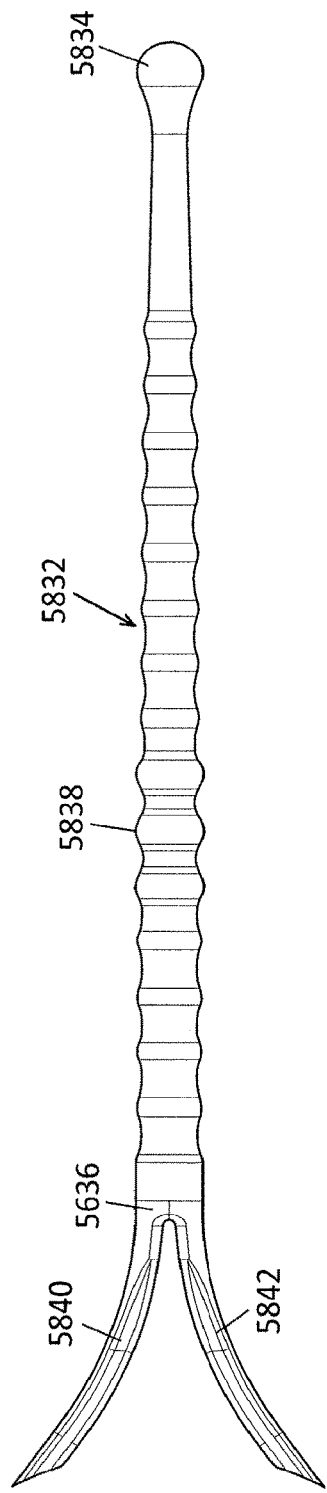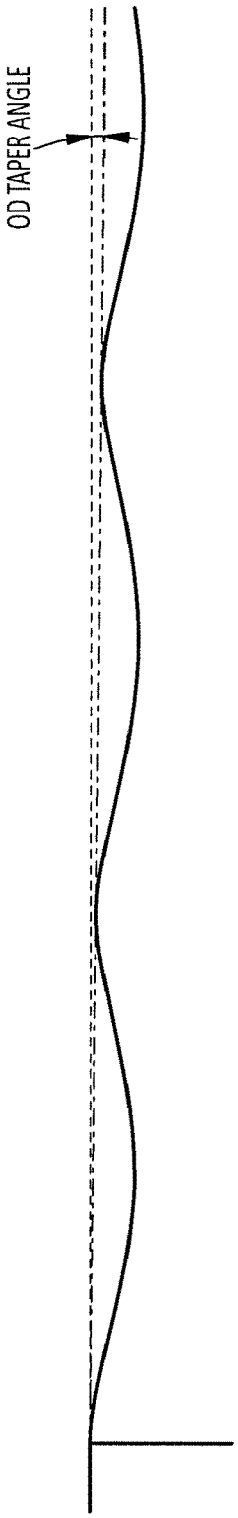
FIG. 58A
FIG. 58B
FIG. 58C

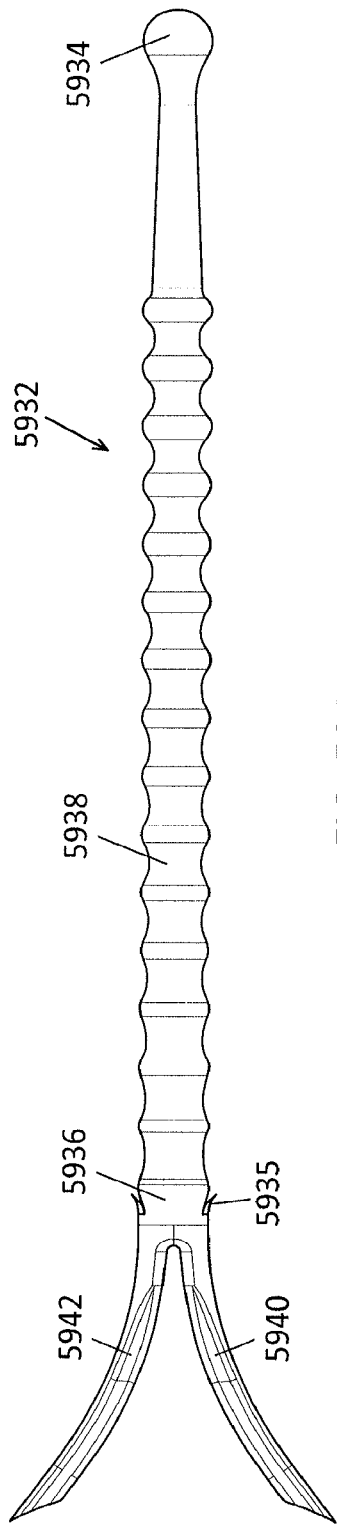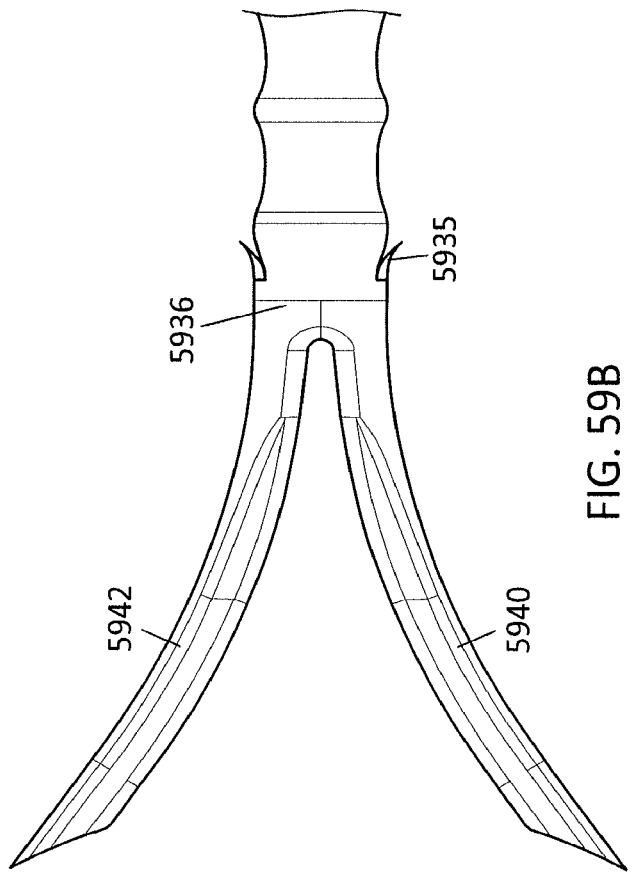
FIG. 59A
FIG. 59B

NASAL IMPLANTS AND METHODS OF USE

CROSS REFERENCE TO RELATED APPLICATIONS

This application is a continuation of U.S. application Ser. No. 16/474,952, filed Jun. 28, 2019, which is a national stage entry of International Patent Application No. PCT/US2017/068419, filed Dec. 26, 2017, which claims priority to U.S. Provisional Application No. 62/440,920, filed Dec. 30, 2016, and titled "NASAL IMPLANTS AND METHODS OF USE", the contents of which are hereby incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention pertains to implants for placing in a body, tools for delivering the implants, and systems and methods for using implants and tools for placing in a body and more particularly to nasal implants, tools for delivering nasal implants, and systems and methods for using such implants and tools.

BACKGROUND

The particular nasal anatomy of an individual may cause or contribute to various problems, such as cosmetic concerns, difficulty breathing, sleep apnea, or snoring, and may impact an individual's health or reduce the quality of life. For example, the structure of an external or internal nasal valve may resist airflow from the nose to the lungs and prevent an individual from getting sufficient oxygen to the blood.

Nasal valve collapse is a frequent cause of nasal airway obstruction, characterized by a loss of support from lateral nasal cartilages typically observed following rhinoplasty, nasal trauma, or in aged patients. Properly functioning nasal cartilage acts to keep the nasal passages open. If the lateral cartilages become weak, they collapse inward when a person inhales due to the negative pressure from the flow of air. This problem is currently largely untreated due to the complexity and highly variable results associated with current repair techniques, combined with the fact that a majority of patients are elderly or have a history of nasal surgery. These complex surgical procedures have been developed to correct valve collapse by reinforcing the lateral cartilages so adequate support can permit valve openings and thus eliminate the nasal airway obstruction.

Overall, nasal valve collapse is an oftentimes untreated problem due to inconsistent results from a myriad of very complex procedures performed by very few surgeons. As such, there remains a need for an endoscopic method to repair nasal valves in a simple, consistent manner.

U.S. Pat. Nos. 8,133,276, 7,780,730, and U.S. Patent Publication No. 2012/0109298 describe implants that can be introduced into the nasal region of an individual using non-surgical injection techniques for treating a nasal valve of an individual. Further, U.S. Patent Publication No. 2016/0058556 describes nasal implants that can be used to treat the nasal valve of an individual.

However, there is a continued need for improvements to address problems attributed to nasal anatomy that are easier to use, last longer, are less invasive, are less expensive to manufacture, and work better.

SUMMARY OF THE DISCLOSURE

The present invention relates to nasal implants, systems for delivering nasal implants, and methods of delivering nasal implants to support a nasal valve of an individual.

In general, in one embodiment, a nasal implant includes a central body having a proximal end and a distal end and first and second arms disposed at the distal end of the central body. The first arm has a proximal end fixed to the distal end of the central body and a distal end not fixed to the body. The distal end of the first arm is adapted to move away from a central longitudinal axis of the central body from a delivery configuration toward a deployed configuration. The second arm has a proximal end fixed to the distal end of the central body and a distal end not fixed to the body. The distal end of the second arm is adapted to move away from a central longitudinal axis of the central body from a delivery configuration toward a deployed configuration. The nasal implant further includes a plurality of barbs configured to engage with tissue when the nasal implant is deployed.

This and other embodiments can include one or more of the following feathers. The plurality of barbs can extend from the central body. The plurality of barbs can extend from the distal end of the central body and point towards the proximal end of the central body. The plurality of barbs can extend at an angle of 15 degrees or greater relative to the central body. There can be two barbs, and the two barbs can extend from opposing surfaces of the central body. There can be a plurality of barbs that extend down each of the opposing surfaces, and the plurality of barbs on each surface can have a staggered configuration along the central body. The plurality of barbs can extend from the first arm and second arm. The plurality of barbs can extend from an outer surface of the first arm and an outer surface of the second arm away from the central longitudinal axis of the central body. The plurality of barbs can extend from an inner surface of the first arm and an inner surface of the second arm towards the central longitudinal axis of the central body. The plurality of barbs on each arm can have a staggered configuration. The plurality of barbs can extend in line or parallel with a plane formed by the first arm and the second arm in the deployed configuration. The plurality of barbs can extend transversely to a plane formed by the first arm and the second arm in the deployed configuration. The plurality of barbs each can have a complementary shape to a plurality of openings on the central body or the first and seconds arm such that, when the nasal implant is in the delivery configuration, the plurality of barbs are engaged with the openings on the central body or the first and second arms. The plurality of barbs can have a notch or tooth configuration. The implant can further include a plurality of openings in the central body portion adapted to allow tissue ingrowth. The implant can further include a plurality of openings in the first and second arms adapted to allow tissue ingrowth. The central body can include a hollow or open structure along a central longitudinal axis of the implant. The central body can include a solid structure along a central longitudinal axis of the implant. The central body can include a closed pitch spiral configuration. The central body can include a unidirectional helix spiral configuration. The central body can include a bi-directional helix spiral configuration. The central body can include an open coil configuration. The central body can include a solid shaft with a spiral cut outer surface. The central body can include a solid shaft with a dual, bi-directional spiral cut outer surface. The implant can further include a first faceted tip on the distal end of the first arm and a second faceted tip on the distal end of the second arm. The implant can further include a first sharpened tip on the distal end of the first arm and a second sharpened tip on the distal end of the second arm. The faceted tip or sharpened tip can include a surface formed from a planar cut at an angle of 45 degrees or less. The faceted tip or sharpened tip can include a surface formed from a planar cut at an angle of 35 degrees or less. The faceted tip or sharpened tip can include two or more surfaces formed from planar cuts. The first arm and the second arm can have an offset configuration such that, in the delivery configuration, the first arm and second arm overlie each other along or adjacent to the central longitudinal axis of the body. The body can consist essentially of a bioabsorbable material. At least one portion of the implant can be composed of a bioabsorbable material. The nasal implant can include two or more different materials. The implant can be made of a material selected from the group consisting of: a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, poly-L-lactic acid (PLLA), poly-D-lactic acid (PDLA), poly-D,L-lactic acid (PLDLLA), or a blend or copolymer thereof. The proximal end can include an atraumatic rounded tip. An outer surface of the nasal implant can include a plasma treated portion. The plasma treated portion can have an increased hydrophilicity. The plasma treated portion can have an increased hydrophobicity.

In general, in one embodiment, a nasal implant includes a central body having a proximal end and a distal end and first and second arms disposed at the distal end. The first arm has a proximal end fixed to the distal end of the central body and a distal end not fixed to the body. The distal end is adapted to move away from a central longitudinal axis of the central body from a delivery configuration toward a deployed configuration. The second arm has a proximal end fixed to the distal end of the central body and a distal end not fixed to the body. The distal end of the second arm is adapted to move away from a central longitudinal axis of the central body from a delivery configuration toward a deployed configuration. The implant has a first stiffness along a first plane of the central body and a second stiffness along a second plane of the central body.

This and other embodiments can include one or more of the following features. The first plane can be formed by the first arm and the second arm in the deployed configuration. The second stiffness can be less than the first stiffness. The first stiffness or the second stiffness can be about 70 N*mm2 to about 150 N*mm2 The first stiffness or the second stiffness can be about 90 N*mm2 to about 105 N*mm2 The second plane can be orthogonal to the first plane. The implant can further include: a stiffness modification adapted to provide the first stiffness and the second stiffness. The stiffness modification can include one or more notches or grooves along at least a portion of a longitudinal length of the central body. The stiffness modification can include flattened surfaces on opposing sides of the central body. The stiffness modification can include a stress distributing rib along the length of the flattened surfaces. The stiffness modification can include one or more openings along the central body. The stiffness modification can include a hollow core along the central body. The stiffness modification can include a tapered cross-section along an axis of the central body with a larger cross-section adjacent the distal end and a smaller size towards the proximal end. The stiffness modification can include the central body having a plurality of different cross-section sizes including a first cross-section adjacent the distal end of the central body, a second-cross section adjacent the first-cross-section, and a third cross-section adjacent to the second-cross-section and the proximal end of the central body, the first cross-section can be larger than the second-cross section and the second cross-section is larger than the third cross-section. The stiffness modification can include a scalloped pattern on an outer surface of the central body. The stiffness modification can include a stiff inner material and a more flexible outer material. The stiffness modification can include the central body having a patterned outer surface with undulations having a varying frequency. The stiffness modification can include a plurality of directional fibers within the implant. The stiffness modification can include a patterned second material on an outer surface of the central body. The stiffness modification can include a repeating pattern on an outer surface of the central body with a first larger cross-section and a second smaller cross-section. The stiffness modification can include a plurality of articulating sections that provide flexibility along a plane orthogonal to the plane defined by the first arm and the second arm in the deployed configuration. The central body can have a tapering outside diameter that decreases from the distal end towards the proximal end. The central body can include a plurality of undulations therein. A diameter of the undulations can increase from the distal end to the proximal end. The central body can include a tapered core therein such that the diameter of the inner core decreases from the distal end to the proximal end. There can be between 6 and 24 undulations along an entire length of the central body. The implant can further include a plurality of openings in the central body portion adapted to allow tissue ingrowth. The implant can further include a plurality of openings in the first and second arms adapted to allow tissue ingrowth. The central body can include a hollow or open structure along a central longitudinal axis of the implant. The central body can include a solid structure along a central longitudinal axis of the implant. The central body can include a closed pitch spiral configuration. The central body can include a uni-directional helix spiral configuration. The central body can include a bi-directional helix spiral configuration. The central body can include an open coil configuration. The central body can include a solid shaft with a spiral cut outer surface. The central body can include a solid shaft with a dual, bi-directional spiral cut outer surface. The implant can further include a first faceted tip on the distal end of the first arm and a second faceted tip on the distal end of the second arm. The implant can further include a first sharpened tip on the distal end of the first arm and a second sharpened tip on the distal end of the second arm. The faceted tip or sharpened tip can include a surface formed from a planar cut at an angle of 45 degrees or less. The faceted tip or sharpened tip can include two or more surfaces formed from planar cuts. The first arm and the second arm can have an offset configuration such that, in the delivery configuration, the first arm and second arm overlie each other along or adjacent to the central longitudinal axis of the body. The body can consist essentially of a bioabsorbable material. At least one portion of the implant can be composed of a bioabsorbable material. The nasal implant can include two or more different materials. The implant can be made of a material selected from the group consisting of: a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, poly-L-lactic acid (PLLA), poly-D-lactic acid (PDLA), poly-D,L-lactic acid (PLDLLA), or a blend or copolymer thereof. The proximal end can include an atraumatic rounded tip. An outer surface of the nasal implant can include a plasma treated portion. The plasma treated portion can have an increased hydrophilicity. The plasma treated portion can have an increased hydrophobicity.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A-3B show a nasal implant with grooves configured to provide modified stiffness.

FIGS. 10A-10B show embodiments of nasal implants made of a composite structure for modified stiffness.

FIGS. 24A-24B show a nasal implant having a laser cut cylindrical pattern for modified stiffness.

FIGS. 26A-26F show additional embodiments of nasal implants.

FIGS. 27A-27F show additional embodiments of nasal implants.

FIGS. 39A-39D show additional embodiments of nasal implants with barbs thereon.

FIGS. 47A-48B show a nasal implant with a plurality of small barbs extending from the inside surface of each of the arms.

FIGS. 48A-48B show another nasal implant with a plurality of small barbs extending from the inside surface of each of the arms.

FIGS. 57A-57D show a nasal implant with a stress distribution rib along the central body.

FIGS. 58A-58C show a nasal implant with a tapered outer diameter.

FIGS. 59A-59B show a nasal implant with barbs thereon.

DETAILED DESCRIPTION

Described herein are devices configured for suspending nasal valves. Specifically, described herein are implants used to support the upper and lateral cartilage.

In some embodiments, the nasal implants described herein can include a central body, two arms, and one or more tissue engagement structures, such as barbs, to improve engagement between the implant and the nasal anatomy. The tissue engagement structures can be on the central body and/or on the arms. In some embodiments, the barbs can include a plurality of tiny barbs that can prevent the withdrawal of the implant. The tiny barbs can be formed with a small cut or slit in the exterior of the implant.

In some embodiments, the nasal implants described herein can include sections with preferential bending or stiffness along different dimensions and at different areas of the implant. The implants can be relatively stiff in some directions to support the nasal valve while allowing bending in other directions to improve movement with the nasal anatomy.

In some embodiments, the nasal implants can also include a sharpened surface to improve the ability of the nasal implant to pierce nasal tissue. In one example, the implant includes a faceted tip.

The size, geometry, and configurations of the nasal implants described herein can be selected to provide the desired amount of support to the body tissue adjacent to the desired implant location. For example, the nasal implant can be relatively stiff in the area adjacent to the nasal valve while being relatively flexible along proximal portions of the implant to move with more flexible portions of the nasal tissue.

Figure 1:
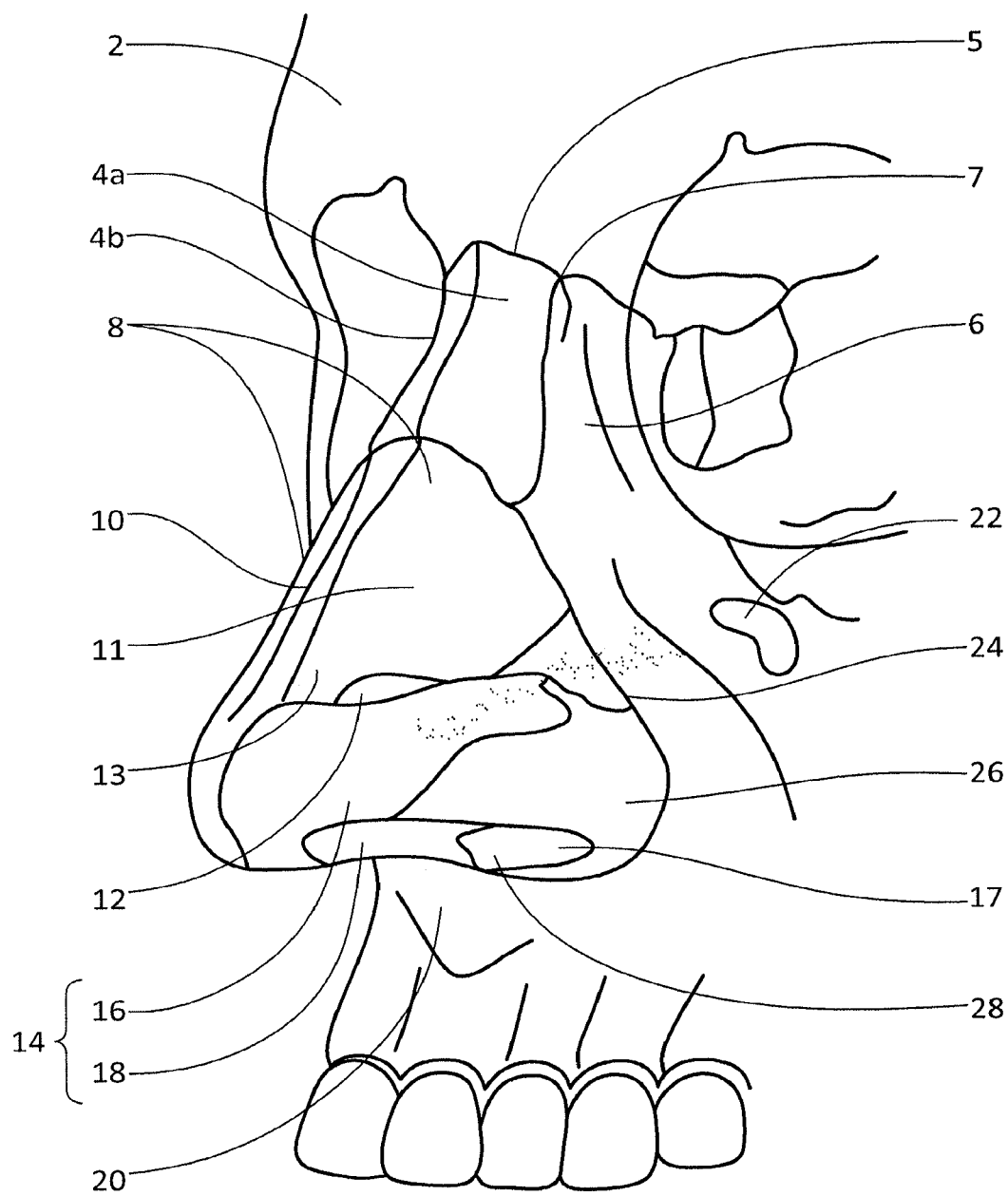
FIG. 1 is a diagram of the structural anatomy and tissues of the face.

FIG. 1 shows the underlying structural anatomy and tissues of a face. The outer layers of overlying skin and muscle have been removed to better show the underlying cartilage and bone that provide structure. The nose sits in the middle of the face and has important responsibilities in olfaction (smelling) and controlling respiration. The nose controls respiration by restricting the flow of air. The nose has two airflow pathways, one on each side of the nose (starting with each nostril) which combine to form a single airflow pathway into the body. Air from the nose flows through the trachea and into the lungs where the air is spread out in the lobules of the lungs and oxygen is absorbed for use by the entire body. Each of the two airflow pathways in the nose has several segments including two types of nasal valves (called external nasal valves and internal nasal valves) along each nasal airflow pathway that act to control airflow through the nose and so together the external and internal valves control airflow into and out of the body. The amount of airflow resistance caused by the valves needs to be "just right"; either too much or too little resistance causes breathing and other problems. The valves are tissues that surround the airflow and the amount of resistance they provide to the airflow is determined largely by their shape and their size (their internal cross-sectional area). The internal nasal valve on each pathway is the narrowest segment of the pathway in the nose and generally creates most of the resistance. Besides the important function of controlling airflow, the internal nasal valves also help give the nose its distinctive shape. A nasal valve is shaped and supported by various structures in the nose and face, with upper lateral cartilage playing a significant role in its form and function. Large and even small changes in internal nasal valve structure can impair nasal breathing, as well as change the cosmetic appearance of the nose. These changes generally act to reduce the cross-sectional area of the internal valve, and can be caused by surgery, another medical treatment, or trauma to the face. Additionally, there are variations of nasal valve structure between individuals, with some individuals having significantly narrowed valves due to weakened or misshaped cartilage, commonly observed as a pinched nose. A narrowed valve region increases the acceleration of airflow and simultaneously decreases intraluminal pressure, causing the valves to collapse. While even normal nasal valves can collapse under great respiratory pressures, dysfunctional internal valves can collapse even during normal breathing, with reduced oxygen flow, snoring and mouth breathing as undesirable consequences.

The nose includes the external nose that protrudes from the face and a nasal cavity underneath the external nose. From top to bottom, the external nose has a root, a bridge, a dorsum (ridge), a free tip (apex), and a columella. The external nose is appended to the piriform aperture, the continuous free edges of the pear shaped opening of the nasal cavity in the skull and is formed by the nasal bones and the maxilla. As shown in FIG. 1, the nose sits in the middle of the face, framed by the bones of the head, with frontal bone 2 superior to the nose, lateral maxilla frontal process 6 lateral to it, and the maxilla anterior nasal spine 20 inferior to it (another lateral maxilla frontal process on the other side of the nose is not visible in this view). The external nose can be roughly divided into three layers from outside to inside: an overlying skin and muscle layer (removed in this view), a middle cartilage and bony framework layer, and an inner mucosal layer (not readily visible in this view).

While the middle cartilage and bony framework layer provides form, structure, and support to the nose, it is also organized to allow the nose to be flexible and wiggle and bend in different directions. It can also be roughly divided into three sections: from top to bottom, they are an upper (superior) bony third, and middle and lower (inferior) cartilaginous thirds. The upper third includes paired left nasal bone 4a and right nasal bone 4b that are joined in the middle of the nose and form the top (or superior) part of the bridge of the nose. Nasal bone 4a (along with lateral maxilla frontal process 6) joins frontal bone 2 superiorly to form the nasofrontal (nasion) suture line 5. Laterally, nasal bone 4a joins the maxilla at its frontal process 6 to form a fibrous joint at the maxilla nasal bone suture line 7 (or nasomaxillary suture line). The middle third of the cartilage and bony framework layer includes septal cartilage 10 which forms part of the septum of the nose and internally separates the nostrils and the two airflow pathways. Lateral process 8 of septal cartilage 10 merges superiorly with upper lateral cartilage 11 (another lateral process on the other side of the nose that merges with upper lateral cartilage on the other side of the nose is not visible in this view). FIG. 1 also shows minor alar cartilage 24, one of several accessory cartilages which provide support and allow movement of the nose, and which impact the complex 3-dimensional shape of the nose. Upper lateral cartilage 11 is normally fairly stiff and it has much of the responsibility for supporting the side of the nose. In conjunction with septal cartilage tissue, it helps to form the internal nasal valve, which is inside the nose under the upper lateral cartilage and not readily visible in this view. As mentioned above, there are two internal nasal valves (one on either side of the nose). Each internal nasal valve is formed by and bordered medially by septal cartilage 10, laterally by the caudal margin 13 of the upper lateral cartilage, and inferiorly by the head of inferior turbinate (not visible in this view) and surrounds an opening through which air flows. The attachment of the upper lateral cartilage to the septum (septal cartilage) forms an angle that defines the internal nasal valve angle (also called simply "valve angle"). The internal nasal valve angle is the narrowest part of the nasal airway and creates resistance that controls airflow through it. There is some natural variation between individuals in their nasal valve angles, and valve angles may change over time as a natural consequence of aging. Valve angle is determined in part by genetics, and an ethnic group has a particular average valve angle associated with it. There is also variation in valve angles between individuals, even within a particular ethnic group, and between an individual's left and right valves. Nasal valve angles may also be altered as a result of surgery, trauma or another intervention. A valve with a valve angle of less than about 10 degrees may generally be considered collapsed, causing nasal airway obstruction with nasal sidewall collapse upon inspiration and may merit treatment such as described herein. A valve angle that is greater 10 degrees may also cause some airway obstruction, cosmetic concern or another concern and may also merit treatment but its dysfunction is generally not as severe as a collapsed valve. Valves in need of treatment may be candidates for treatment using the implants, devices, systems and methods described herein.

The lower third of the cartilage and bony framework layer includes major alar cartilage (also referred to as lower lateral cartilage or inferior lateral cartilage, based on its location and to distinguish it from upper lateral cartilage) that help shape the nostrils and the tip of the nose. This cartilage is softer and more mobile than upper lateral cartilage, and it allows the tip of the nose to move. Major alar cartilage 14 is U-shaped and includes lateral crus 16 and medial crus 18. Major alar cartilage 14 forms part of external valve around nostril 17 (also called nares), though it does not quite reach the bone laterally. The lower third of the cartilage and bony framework layer also includes alar fibrofatty tissue 26 of alar that fills the gap between lateral crus 16 and the bone. FIG. 1 also shows small accessory alar cartilage 12 that links the major alar and lateral cartilage 8 of the cartilage and bony framework layer.

As mentioned above, the nose is a complex, 3-dimensional structure. It may be desirable to change its shape or better support its structure in order to improve or maintain its function or appearance (cosmesis), but it can be difficult to change one aspect of the nose without adversely affecting another part. Indeed, previous surgical interventions are one cause of altered nasal valve function that may be treated using the systems and methods described herein. Described herein are implants, devices, systems and methods function for changing or supporting an aspect of a body structure or shape, including of the nose.

Figure 2A:
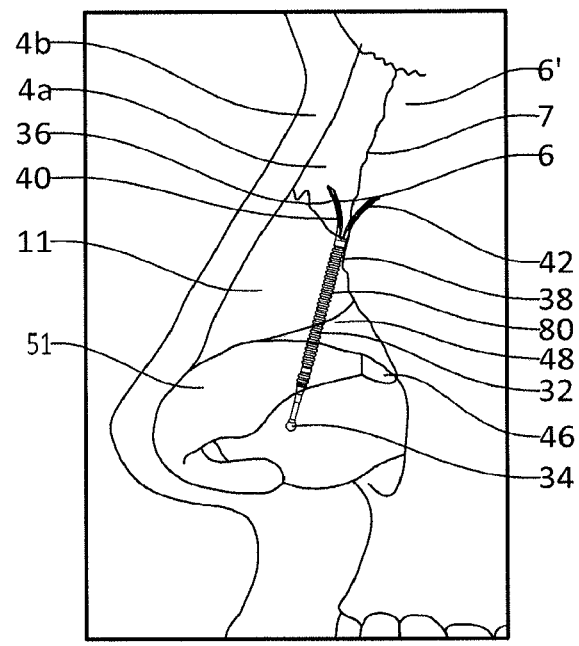
FIGS. 2A-2B show front and side views of an exemplary implant in a patient's nasal anatomy.
Figure 2B:
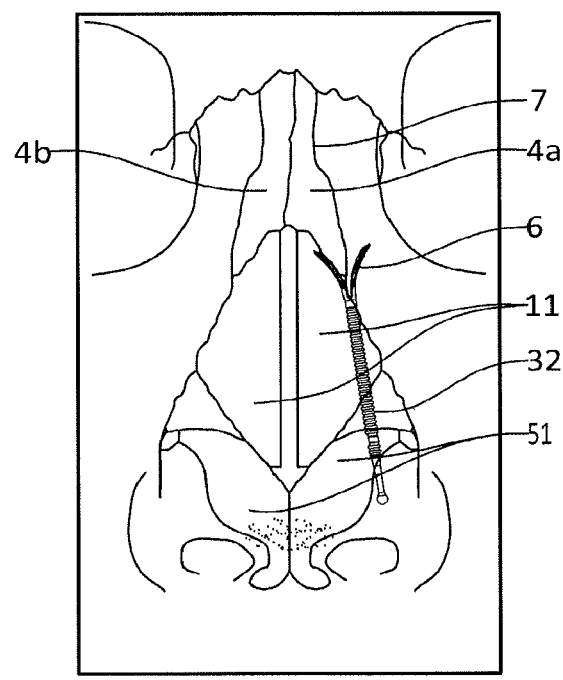

FIGS. 2A-2B show front and side views, respectively, of an exemplary implant 32 implanted in a patient's nose and supporting a tissue section of a patient's nose. The implant 32 has a body with a proximal end 34, a distal end 36, and a central body 38 between the proximal and distal ends. The distal end 36 of implant 32 is forked with first arm 40 and second arm 42 forming the tines of the fork. Each arm 40, 42 has a proximal end fixed to the central body 38 of the implant body and a distal free end not fixed to the central body 38. Further, the central body 38 may include one or more ribs 80 (also called ridges) thereon. The implant 32 can have one or more ribs 80 or other body features, such as a bevel, scallop, or wing.

The implant 32 may be useful for maintaining or improving nasal function or appearance. FIGS. 2A-2B show implant 32 in place for supporting or changing an internal nasal valve. The implant 32 can appose structures in the cartilage and bony framework layer under the skin and muscle. The central body 38 is in a position between the nasal cartilage and patient skin or muscle and apposes upper lateral cartilage 11 and lower lateral cartilage 51. As such, the central body 38 can appose the caudal end 48 of the upper lateral cartilage 11 and so overlay or acts on the internal valve wall, providing support to or changing a shape of the internal valve. The distal end 36 of implant 32 apposes structures in the upper part of the cartilage and bony framework layer. Further, in this example, the arms 40, 42 appose nasal bone 4a, frontal process 6 of the maxilla bone, and maxilla nasal bone suture line 7 (nasomaxillary suture line). The ribs 80 can help anchor an implant in place, such as by catching tissue against the rib, valley, or otherwise. In some variations, a distal end of the implant 32 may be apposed or in proximity to one of more structures in the upper layer or any of the structures or tissues in the middle or lower cartilage and bony framework layer (e.g., accessory cartilage, major alar cartilage, minor alar cartilage, septal cartilage, maxilla, etc.).

The nasal implant 32 can have a forked end that anchors and remains parallel to the nasal bone/maxilla bone construct of the nose. This geometric feature can help ensure that the nasal implant 32 remains in a known orientation after implantation. Additional features on the implant 32, such as barbs, can be used as orientation features that allow the implant features to be designed to provide support in the same plane as the deflection of the nasal valve collapse.

Because the implant 32 has features that enable exact placement and orientation of the implant, designing implant geometries with preferred stiffness in specifically selected orientations is possible. The nasal implant 32 can thus be designed to incorporate preferential stiffness or flexibility in a plane or orientation of choice by the designer. The implant 32 can be selectively created to be stiff in one orientation and less stiff or flexible in another (e.g., stiff in an orientation normal to the lower lateral or upper lateral cartilage and more flexible in the orientation parallel to these structures to provide improved support of the cartilages and nasal valve).

In some embodiments, implant features, such as a non-round cross-section, layered materials of different molecular weight, intrinsic viscosity, and different compositions of Poly(L-lactide) (PLLA), Poly(D-lactide) (PDLA), Poly(L-lactide-co-D-lactide) (PLDA), Poly(L-lactide-co-D,L-lactide) (PLDLLA), Poly(D,L-lactide) (PDLLA), Polyglycolic Acid (PGA), Polycaprolactone (PCL), Poly(dioxanone) (PDS), their copolymers and combinations thereof, can be used to impart preferential stiffness in one plane and not the other plane(s) of implant 32.

In some embodiments, grooves or scallops along the length of the implant 32 can preferentially make the implant less stiff in one plane and more stiff in another. The grooves or scallops can be spaced unevenly to provide for different stiffness at different parts of the implant 32. For example, the implant 32 can be designed to be stiff in one direction to keep the nasal valve open but allow movement of the nasal tissue. In yet another example, a separate member of the nasal implant 32 can be clipped in to give preferential stiffness. In yet another example, articulating sections can be used for the implant 32 that allow free movement until they reach a certain point and then movement stops. In another example, the nasal implant 32 can be made from a stiff core with oriented fibers and injection molding on top of the stiff core. In another example, patterns can be formed on the nasal implant 32 to modulate stiffness, e.g., through laser cutting. In another example, molding patterns can be used to mold at different thicknesses in one plane to achieve preferential stiffness for the implant 32.

In some embodiments, the implant 32 can have a first flexural rigidity or first stiffness along a plane formed by the first arm and second arm in the deployed configuration. The implant 32 can have a second flexural rigidity or second stiffness along a plane other than the plane formed by the first arm and second arm in the deployed configuration. The second flexural rigidity or second stiffness can be less than the first flexural rigidity or first stiffness. The flexural rigidities of the nasal implant 32 can be designed to vary from 0-300% or more between the plane formed by the arms to other planes of the implant. The plane other than the plane formed by the first arm and second arm in the deployed configuration can be orthogonal to the plane formed by the first arm and second arm in the deployed configuration. In some embodiments, the nasal implant 32 can have three or more different flexural rigidities in three or more different planes/sections.

In some embodiments, the flexural rigidity can vary along an axial length of the nasal implant 32. The flexural rigidity can vary gradually along the axial length of the nasal implant 32, for example, with a tapered profile or configuration.

In some embodiments, the flexural rigidity or stiffness at a specific point along the axial length of the nasal implant 32 can be omnidirectional, non-planer, or symmetrical. For nasal implants with a symmetrical cross-section, the flexural rigidity can be omnidirectional at that specific point of the nasal implant 32.

In some embodiments, the implant 32 can have a first flexural rigidity or first stiffness at a first portion of the central body. The first flexural rigidity or first stiffness at the first portion of the central body can be symmetrical or omnidirectional. In some embodiments, the implant 32 can have a second flexural rigidity or second stiffness at a second portion of the central body. The second flexural rigidity or second stiffness at the second portion of the central body can be symmetrical or omnidirectional.

In some embodiments, the nasal implant geometry of the implant 32 can form regions of flexural rigidity relative to the plane formed by the arms along with a tiered or gradual increase or decrease in flexural rigidity along the axis of the nasal implant. These geometries can include parallel elongate features that run alongside the device, which are tapered to create a gradual change in flexural rigidity. The geometries can also include inclusions such as flutes or grooves, of varying size and shape, which change the relative rigidity of the device along its axis by changing the effective cross section of the device along its axis.

Any of the flexural rigidities in the nasal implant 32 can be combined or substituted for one another. For example, the nasal implant 32 can have a flexural rigidity adjacent to the forked end in a plane defined by the arms of the fork, along with a tapered longitudinal configuration where the flexural rigidity decreases from the forked end to the proximal end.

The specific flexural rigidity profile of the nasal implant 32 can be pre-selected to match the properties to the desired clinical use. For example, the stiffness or flexural rigidity can be selected in some implant areas to support or match the properties of nasal tissue like the lateral nasal cartilage. The flexural rigidity and stiffness can also be selected to minimize the stress concentration and distributions along the length of the implant while also minimizing the maximum stress while bending.

The stiffness of the implant 32 can be selected based on matching the stiffness of native nasal cartilage. However, depending on the goals of nasal implant 32, the implant design can also be purposefully intended to be more or less flexible than the native nasal cartilage. For example, implants intended to support the lateral wall can have a flexural rigidity of about 70 $N*mm^2$ to about 150 $N*mm^2$ or 90 $N*mm^2$ to about 105 $N*mm^2$. In some embodiments, the device can have a first flexural rigidity of about 70 $N*mm^2$ to about 150 $N*mm^2$, such as about 90 $N*mm^2$ to about 105 $N*mm^2$. In some embodiments, the device can have a second flexural rigidity of about 70 $N*mm^2$ to about 150 $N*mm^2$, such as about 90 $N*mm^2$ to about 105 $N*mm^2$. The stiffness of native nasal cartilages can range from 1.5 $N*mm^2$ for lower lateral cartilage to 220 $N*mm^2$ for septal cartilage grafts. Thus, embodiments can be envisioned to have first and second flexural rigidities within this range depending on the desired goals of the implant.

In some embodiments, the flexural rigidity or stiffness profile can be pre-selected and implemented by a stiffness modification to the nasal implant 32, in particular the profile and configuration of the central body of the nasal implant. In one example, the stiffness modification can be adapted to provide the first flexural rigidity or first stiffness and the second flexural rigidity or second stiffness.

A number of different stiffness modifications are illustrated and described herein.

In one example, the stiffness modification includes one or more notches or grooves along all or a portion of a longitudinal length of the central body. Examples of grooves and notches are shown in FIGS. 3A-3B and 7A-7C.

Figure 34A:
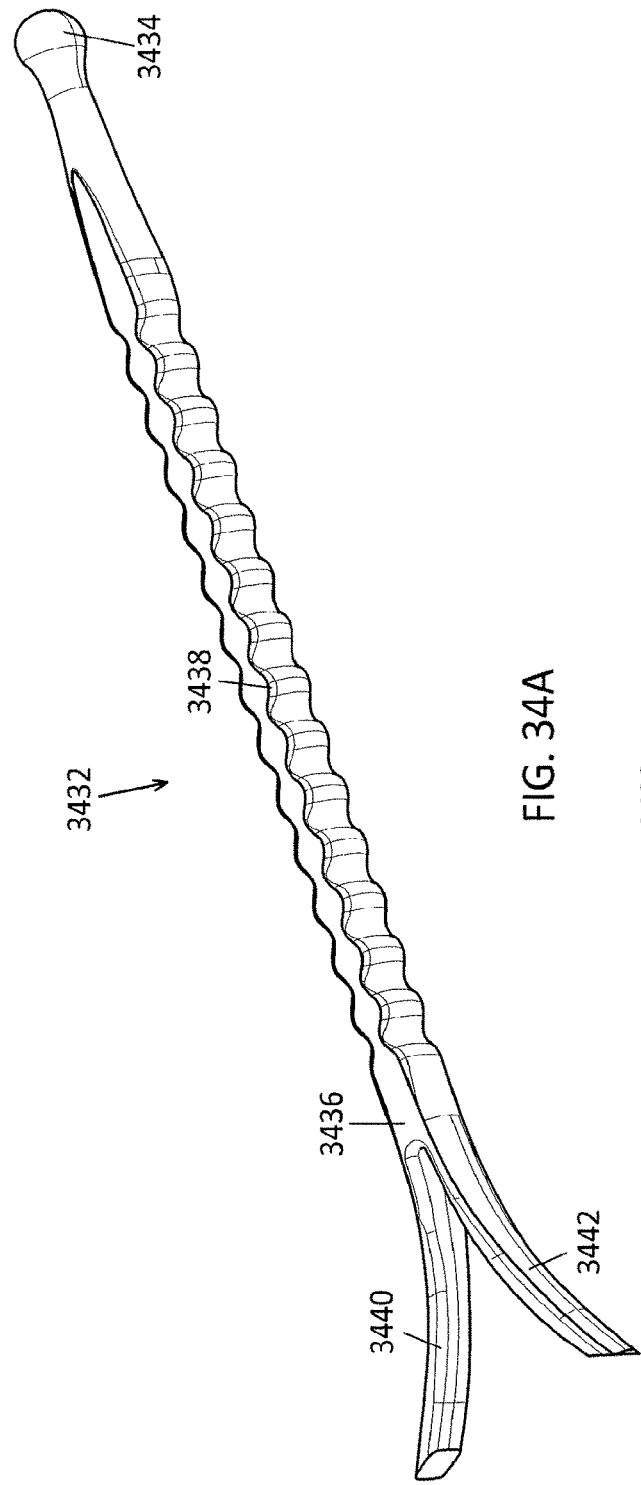
FIGS. 34A-34B show a nasal implant with flattened surfaces and scalloped or ridged surfaces therebetween for modified stiffness.
Figure 34B:
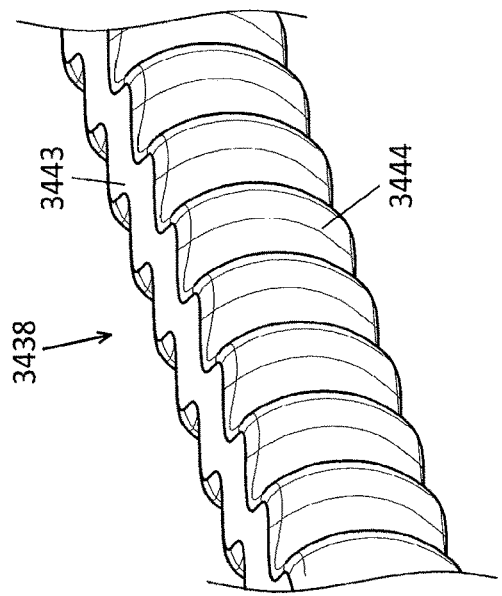

In one example, the stiffness modification includes flattened surfaces on opposing sides of the central body. An example of flattened surfaces is shown in FIGS. 34A-34B.

Figure 6:
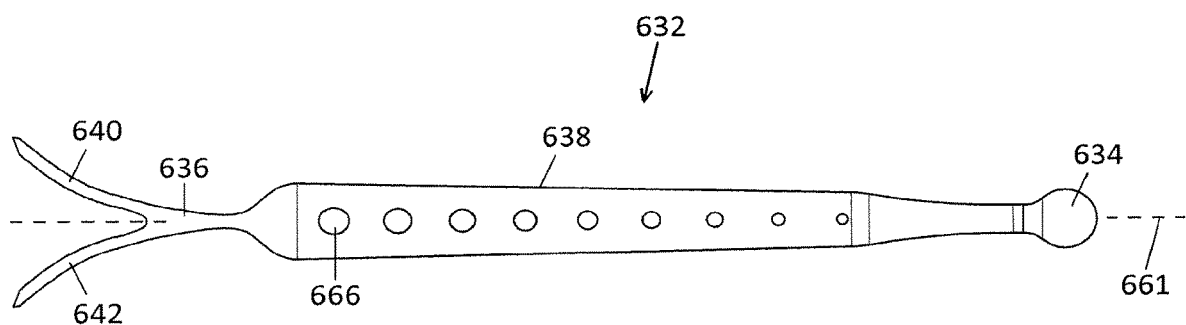
FIG. 6 shows a nasal implant with through-holes along the central body that provide modified stiffness.
Figure 15:
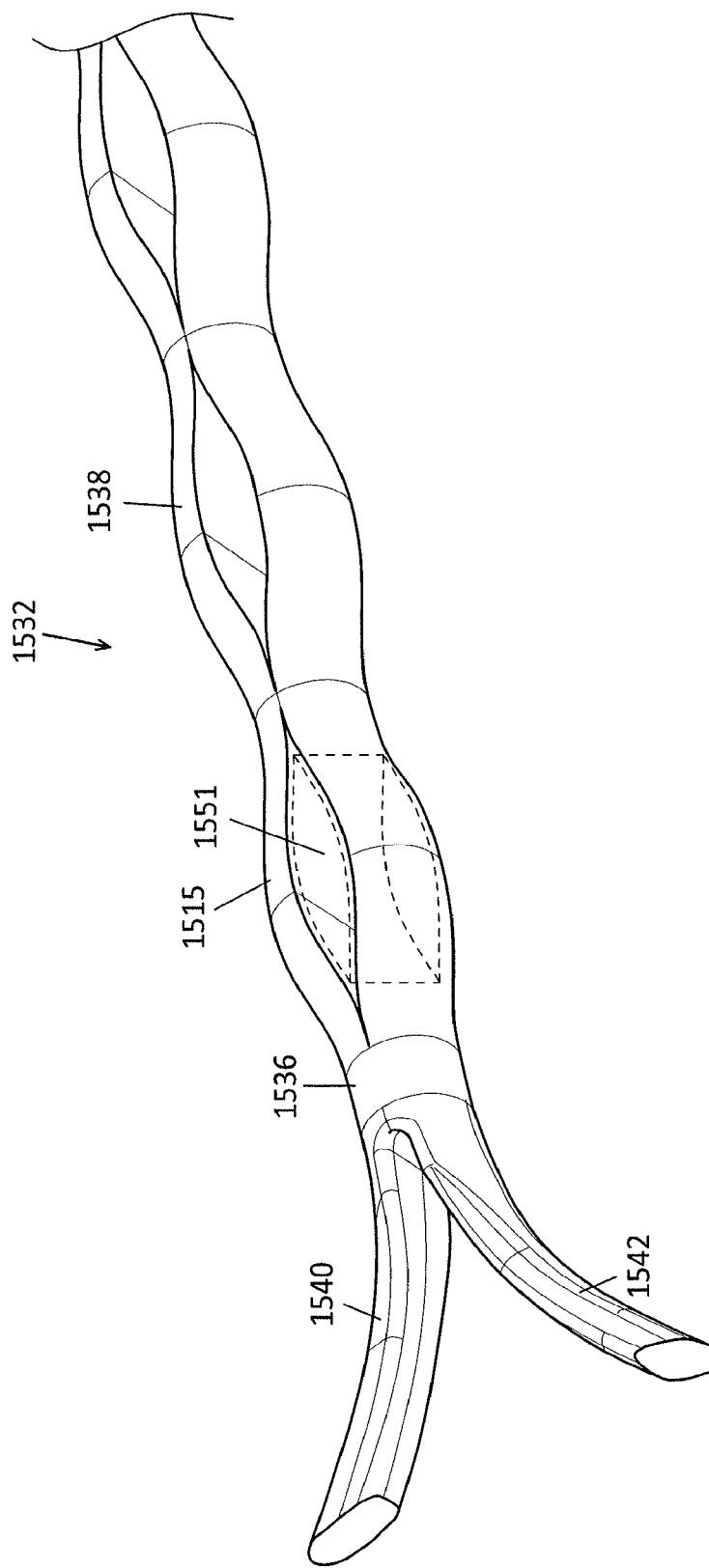
FIG. 15 shows a nasal implant with hollow sections that provide tissue ingrowth for anchoring of the implant.

In one example, the stiffness modification includes one or more openings along the central body. An example of a nasal implant with one or more openings is shown in FIGS. 6 and 15.

In one example, the stiffness modification includes a hollow core along all or a portion of the central body. In some cases, the implant can have a plurality of discontinuous hollow portions in the central body.

In one example, the stiffness modification includes a tapered cross-section along an axis of the body with a larger cross-section adjacent the distal end and a smaller cross-section size towards the proximal end. An example of a tapered nasal implant is shown in FIGS. 5A-5B and 7A-7C.

In one example, the stiffness modification can include the central body having a generally tapering outside diameter from the distal end towards the proximal end. An example of a nasal implant with a generally tapering outside diameter is shown in FIGS. 57A-57D and 58A-C.

In one example, the stiffness modification includes a stress distributing rib or ridge along a portion of the length of the central body. The stress distributing rib or ridge can be on opposing sides of the nasal implant. The stress distributing rib or ridge can be positioned on opposing flattened surfaces of the central body of the implant. An example of a nasal implant with a stress distributing rib is shown in FIGS. 57A-57D.

In some embodiments, the stiffness modification can be along a portion of the central body. For example, when the central body includes a plurality of undulations with an inner diameter and an outer diameter, the stiffness modification can include the central body having a tapered core section defined generally by the inner diameter of the undulations. The tapered core section can start at a predetermined offset distance from the outer diameter of the undulations. An example of such a nasal implant is shown in FIGS. 57A-57D.

In one example, the stiffness modification includes the central body having a plurality of different cross-section sizes, including a first cross-section adjacent the distal end of the central body, a second-cross section adjacent the first-cross-section, and a third cross-section adjacent to the second-cross-section and the proximal end of the central body. The first cross-section can be larger than the second-cross section and the second cross-section can be larger than the third cross-section. An example is shown in FIGS. 7A-D. In some embodiments, the cross-section can increase from the proximal to the distal end.

Figure 19:
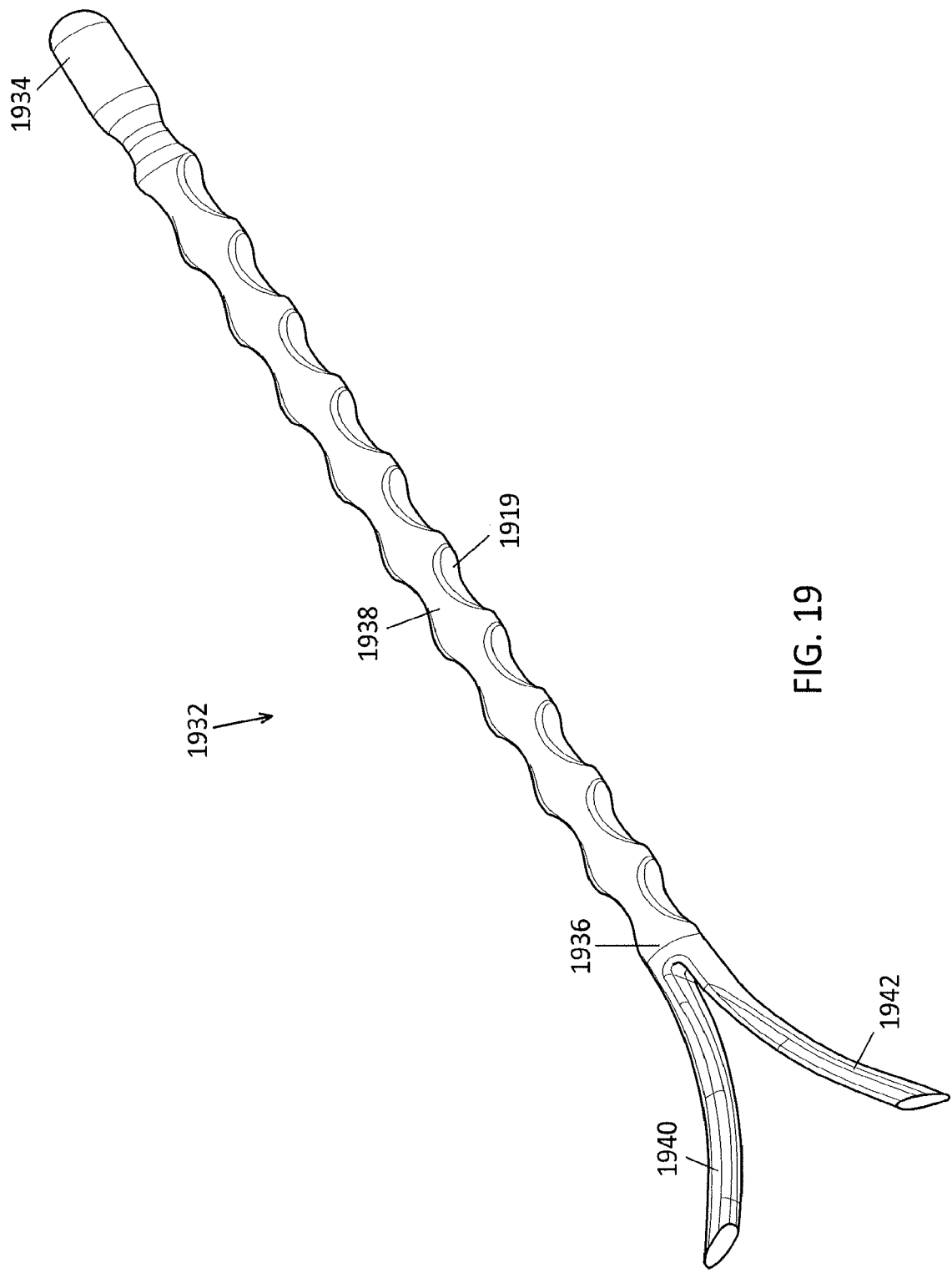
FIG. 19 shows a nasal implant including scalloped features to provide modified stiffness.
Figure 25:
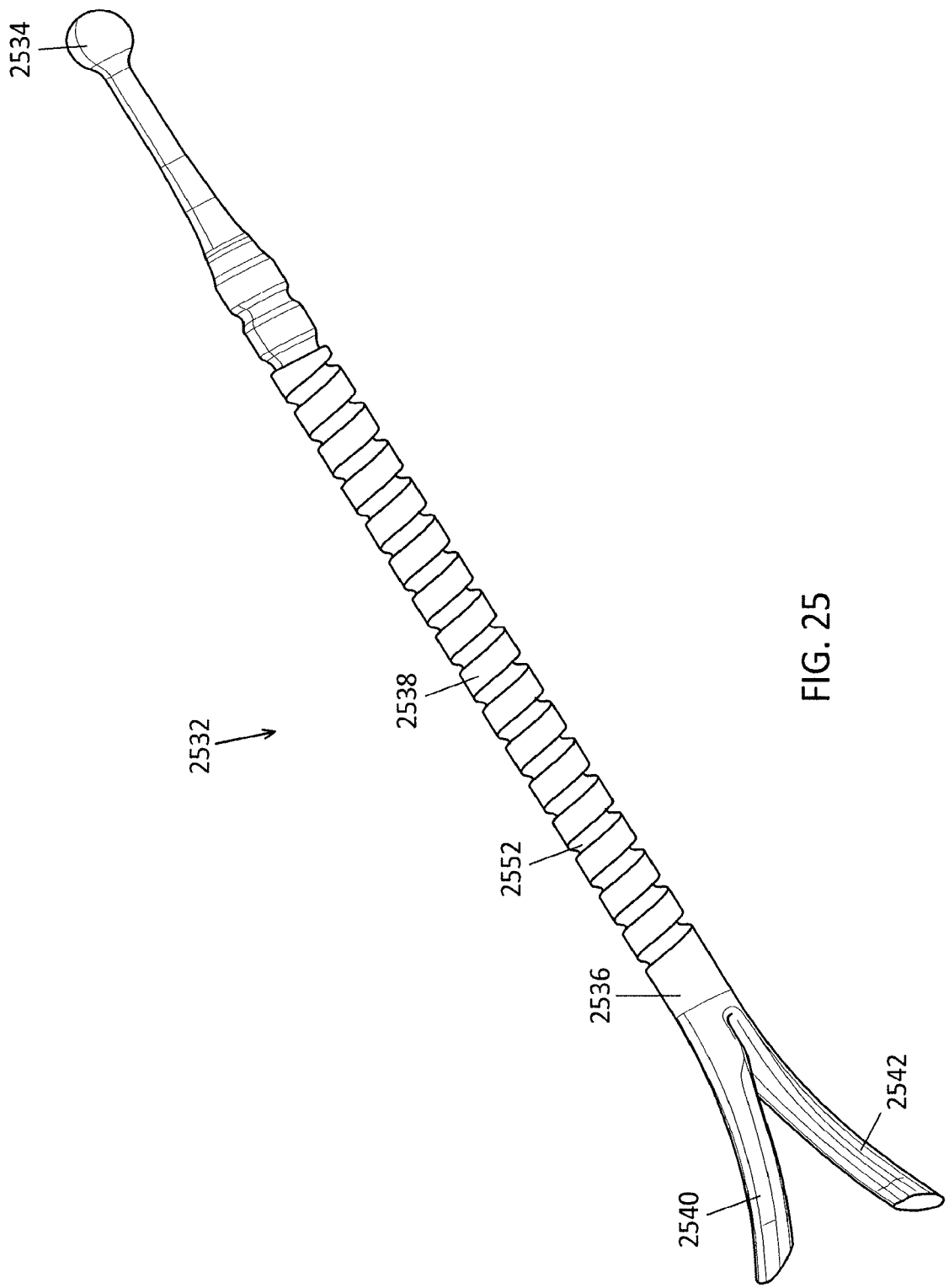
FIG. 25 shows a nasal implant with a helical grooved scallop extending therearound.

In one example, the stiffness modification includes a scalloped pattern on an outer surface of the central body. Examples are shown in FIGS. 19 and 25.

Figure 14:
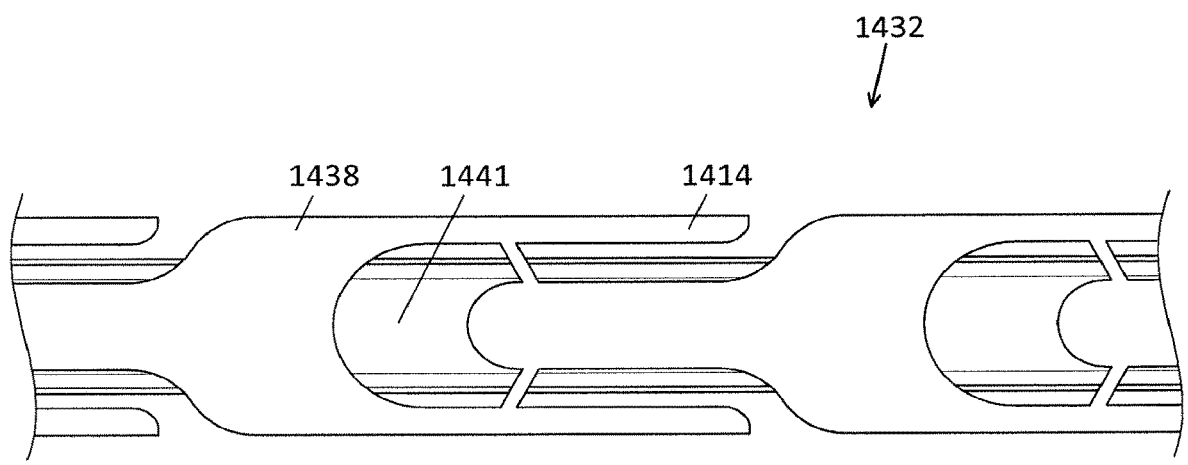
FIG. 14 shows a nasal implant with a patterned surface to provide anchoring of the implant.

In one example, the stiffness modification includes a stiff inner material and a more flexible outer material. An example is shown in FIG. 14.

In one example, the stiffness modification includes the central body having a patterned outer surface with undulations having a varying frequency. Examples are shown in FIGS. 7A-D and 26A-F.

In one example, the stiffness modification includes a plurality of directional fibers within the implant. The directional fibers can be coated by another material or can be on a portion of the outer area of the implant. An example is shown in FIGS. 10A-10B.

Figure 17:
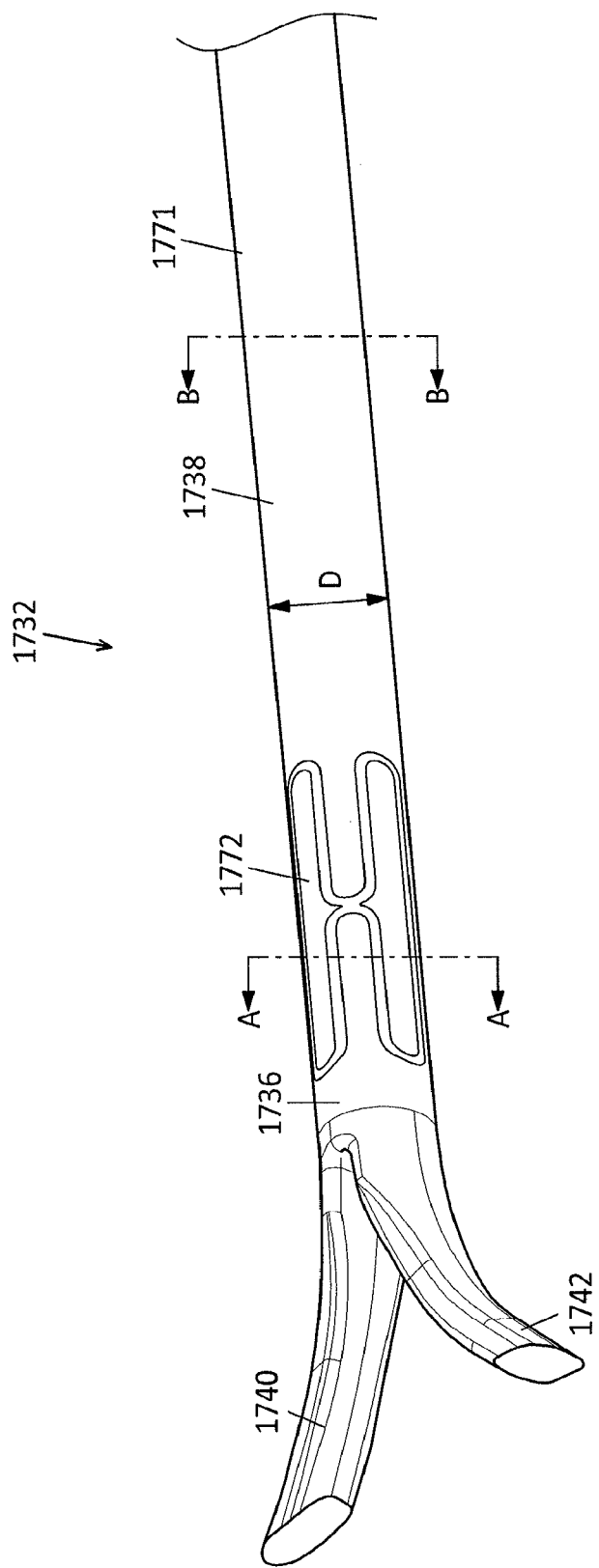
FIG. 17 shows a nasal implant with an etched pattern to provide modified stiffness.

In one example, the stiffness modification includes a patterned second material on an outer surface of the central body. The stiffness of the implant can be increased in the region with the patterned material. An example is shown in FIG. 17.

Figure 16:
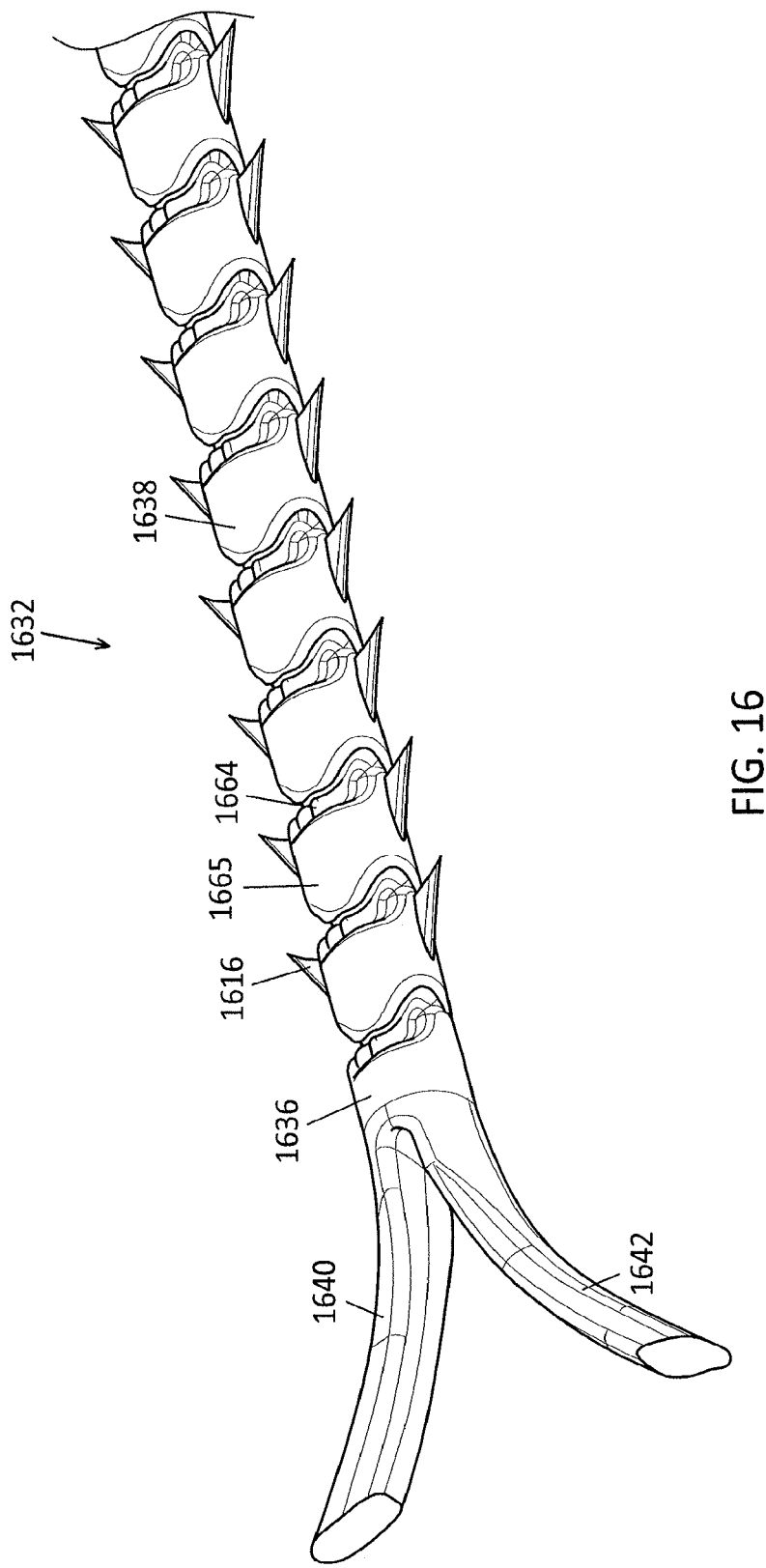
FIG. 16 shows a nasal implant with barbs configured to prevent migration of the implant.

In one example, the stiffness modification includes a repeating pattern on an outer surface of the central body with a first larger cross-section and a second smaller cross-section. An example is shown in FIG. 16.

In one example, the stiffness modification includes a plurality of articulating sections that provide flexibility along a plane orthogonal to the plane defined by the first arm and the second arm in the deployed configuration. Examples are shown in FIGS. 16, 22A-C, and 23.

A number of different implant features are illustrated and described herein.

In some embodiments, the central body includes a hollow or open structure along the central longitudinal axis of the body. The central body can include a closed pitch spiral configuration, such as the configuration illustrated in FIG. 28. The central body can include a uni-directional helix spiral configuration, such as the figuration illustrated in FIG. 29. The central body can include a bi-directional helix spiral configuration, such as the figuration illustrated in FIG. 33. The central body can include an open coil configuration, such as the figuration illustrated in FIG. 30. Combinations of any of these configurations can be used to achieve a desired stiffness profile along the axis of the central body along with a desired amount of tissue ingrowth.

In some embodiments, the central body includes a solid or closed structure along the central longitudinal axis of the body. The central body can include a solid shaft with a spiral cut outer surface, such as the figuration illustrated in FIG. 31. The central body can include a solid shaft with a dual, bi-directional spiral cut outer surface, such as the figuration illustrated in FIG. 32.

A distal end of the arms of the implant can include a sharpened or faceted tip. FIGS. 53A-55B illustrate several examples of faceted tips. The sharpened or multi-faceted distal end of the arms can include a beveled face in at least two directions. The sharpened or faceted tip with multiple edges can result in a point for piercing tissue rather than just a cutting edge if the edge has only one plane. In some embodiments, the faceted tip or sharpened tip includes a surface formed from a planar cut at an angle of 45 degrees or less. In some embodiments, the faceted tip or sharpened tip includes a surface formed from a planar cut at an angle of 35 degrees or less. In some embodiments, the faceted tip or sharpened tip includes two or more surfaces formed from planar cuts.

In some embodiments, the first arm and the second arm have an offset configuration such that, in the delivery configuration, the first arm and second arm can overlie each other along or adjacent to the central longitudinal axis of the body. For example, the two arms can have scissor-like configuration to reduce the profile of the arms in the delivery configuration, such as the configuration illustrated in FIGS. 55A-B.

The nasal implants described herein can include one or more barbs to improve tissue engagement. The barbs can be generally directed such that implant moves easily in the distal direction but not in the proximal direction. For example, the barbs can project outward and towards the proximal end of the implant to provide resistance to migration in the proximal direction. In general, when the implant is pulled in the proximal direction, the forks can move apart and make withdrawal more difficult. When the implant is pulled proximally, the barbs can also expand to provide resistance to proximal movement. For example, when barbs are positioned on the interior of forks, the barbs can further engage the tissue as the implant is pulled in the proximal direction, making withdrawal even more difficult.

In some embodiments, the barbs have a notch or tooth configuration. The barbs can be adapted to facilitate tissue in-growth when the implant is engaged with a portion of a nasal tissue of a patient.

In one example, the implants with the barbs can be made by molding the implant with a protrusion and can then cutting the protrusion after molding to form the hinge. In another example, the barbs can be formed by skiving. In one example, the barbs can be formed by a living hinge designed to fold out after deployment, such as the configuration of FIG. 36. In another example, barbs can be formed with a small cut or slit in the exterior of the implant.

In some embodiments, the barbs extend from the central body of the implant. The barbs can each have a complementary shape to a plurality of openings on the central body such that, when the nasal implant is in the delivery configuration, the barbs are engaged with the openings on the central body and thus flush with the central body. The barbs can extend from opposing surfaces of the central body portion. In some embodiments, the barbs on the opposing surfaces of the central body portion have a staggered configuration along the central body portion.

In some embodiments, the barbs extend from the distal end of the body of the implant. For example, barbs can extend from the first arm and second arm. The barbs can extend from an outer surface of the first arm and an outer surface of the second arm away from the central longitudinal axis of the body or the plurality of barbs can extend from an inner surface of the first arm and an inner surface of the second arm towards the central longitudinal axis of the body. In some embodiments, the barbs can be staggered on the interior of the arms so that they do not add to the diameter of the implant in the delivery configuration. For example, the barbs can be offset like scissors to allow for use with a smaller cannula or delivery device.

In some embodiments, the plurality of barbs extend in line or parallel with a plane formed by the first arm and the second arm in the deployed configuration. In some embodiments, the plurality of barbs extend transversely to a plane formed by the first arm and the second arm in the deployed configuration. Barbs can also extend in other orientations relative to the implant as well.

In some embodiments, the nasal implants described herein can include a plurality of openings to facilitate tissue ingrowth after the implant is deployed in the patient. The openings can be, for example, in the central body portion or the arms.

A number of different examples and modifications of implants are described herein. Features of any embodiment can be combined or substituted with features of any other embodiment.

The implants described herein can have modified stiffness and/or flexibility to provide the desired characteristics along various planes, axes, and/or locations.

Figure 4A:
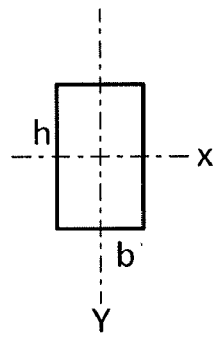
FIGS. 4A-4C illustrate the relationship between the cross-sectional profile of a material and the moment of inertia.
Figure 4B:
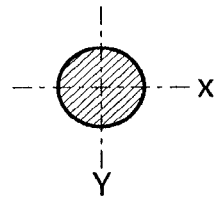
Figure 4C:
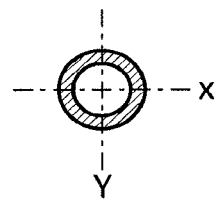

FIGS. 3A-3B shows an implant 332 with modified stiffness having a central body 338, an atraumatic proximal end 334, and a distal end 336 with two forked arms 340, 342. Longitudinal grooves 333 extend along the length of the central body 338 to preferentially make the nasal implant less stiff in one plane and more stiff in another. As used herein, stiffness, k, can be defined as the extent to which the implant resists deformation in response to an applied force, k=F/δ where F is the force applied on the body and δ is the displacement produced by the force. FIGS. 4A-4C illustrate the relationship between the cross-sectional profile of a material and the moment of inertia. For a rectangular material the moment of inertia (Ix) can be represented as: $I_x=(bh^3)/12$. For oval cross-sections, the moment of inertia can be represented by $I_x=\pi r^4/4$. For an annular material, the moment of inertia can be represented as $I_x=\pi(r_o^4-r_i^4)/4$. With the moment of inertia correlating to multiple powers of the cross-sectional dimensions, small changes in the cross-sectional dimensions, such as the use of grooves 333, can have a large effect on the moment of inertia and therefore the stiffness.

Figure 5A:
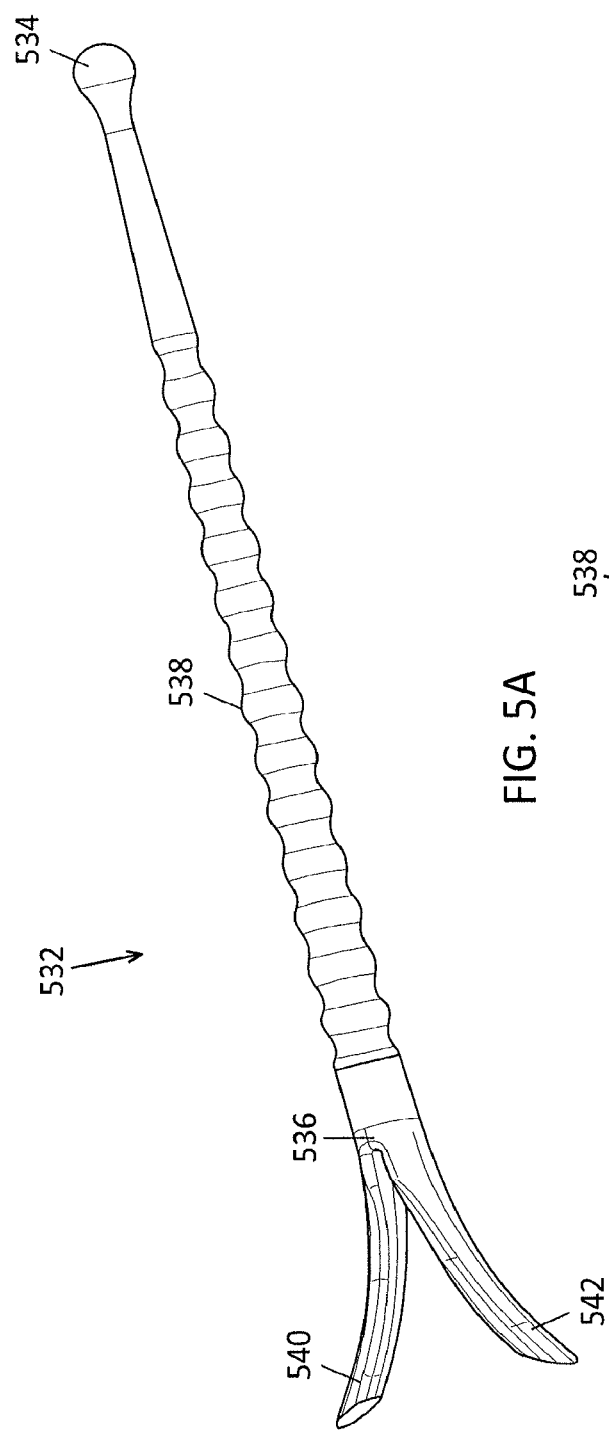
FIGS. 5A-5B show a nasal implant with a tapered cross-section that provides modified stiffness.
Figure 5B:
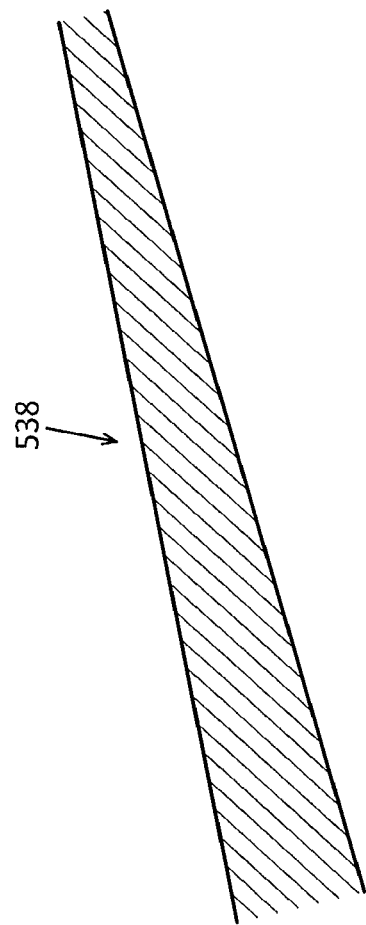

FIGS. 5A-5B illustrate a nasal implant 532 having a central body 538, an atraumatic proximal end 534, and a distal end 536 with two forked arms 540, 542. The central body 538 includes a tapered cross-section (as shown in FIG. 5B) with a diameter that decreases from the distal end 536 to the proximal end 534, providing increased stiffness at the distal end 536 relative to the proximal end 534.

FIG. 6 illustrates a nasal implant 632 having a central body 638, an atraumatic proximal end 634, and a distal end 636 with two forked arms 640, 642. Multiple through-holes 666 extend along the longitudinal axis 661 of the central body 638. In some embodiments, the holes 666 can decrease in diameter from the distal end 636 towards the proximal end 634. The through-holes 666 can reduce the stiffness of the implant 632 in certain directions and improve tissue ingrowth.

Figure 7A:
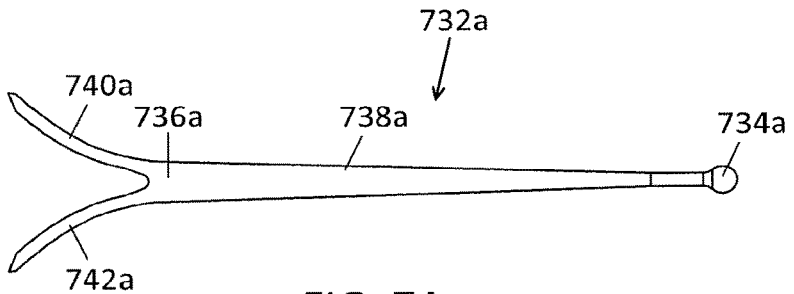
FIGS. 7A-7D show various embodiments of nasal implants with different surface modifications and cross-sectional shapes to provide modified stiffness.
Figure 7B:
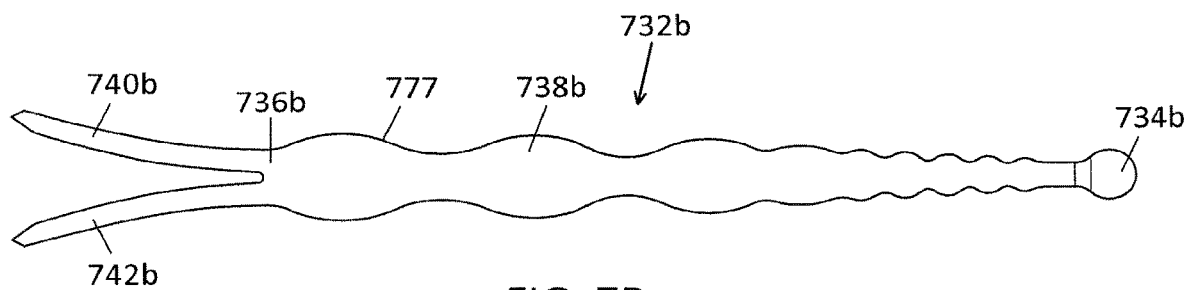
Figure 7C:
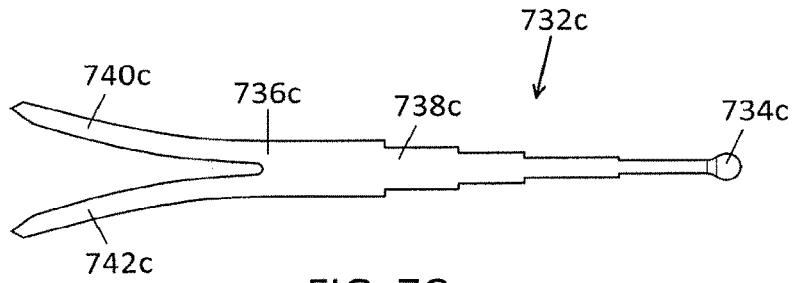
Figure 7D:
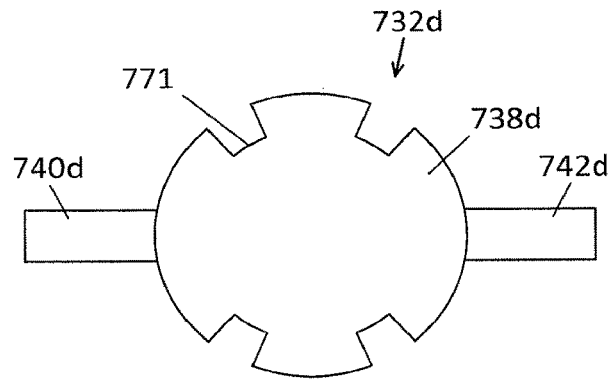

FIGS. 7A-7D illustrate embodiments of nasal implants with different surface modifications and cross-sectional shapes. As shown in FIG. 7A, nasal implant 732a can have a central body 738a, an atraumatic proximal end 734a, and a distal end 736a with two forked arms 740a, 742a. The central body 738a can have a smooth tapered cross-section that decreases from the distal end 736a to the proximal end 734a. As shown in FIG. 7B, a nasal implant 732b can have a central body 738b, an atraumatic proximal end 734b, and a distal end 736b with two forked arms 740b, 742a. The central body 738b can have a plurality of undulations 777, such as ribs or scallops, extending circumferentially around the central body 738b. The frequency of the undulations 777 can increase from the distal end 736b to the proximal end 734b. The higher frequency of the undulations 777 can increase the flexibility of the nasal implant closer to the proximal end 734b. As shown in FIG. 7C, nasal implant 732c can have a central body 738c, an atraumatic proximal end 734c, and a distal end 736c with two forked arms 740c, 742c. The central body 738c can have step changes in cross-sectional area such that the area decreases from the distal end 736c to the proximal end 734c, thereby reducing the stiffness at the proximal end 734c. As shown in FIG. 7D, a nasal implant 732d with a central body 738d and two arms 740d, 742d can have a series of splines 771, grooves, or notches in the central body 738d to vary and/or reduce stiffness.

Figure 8A:
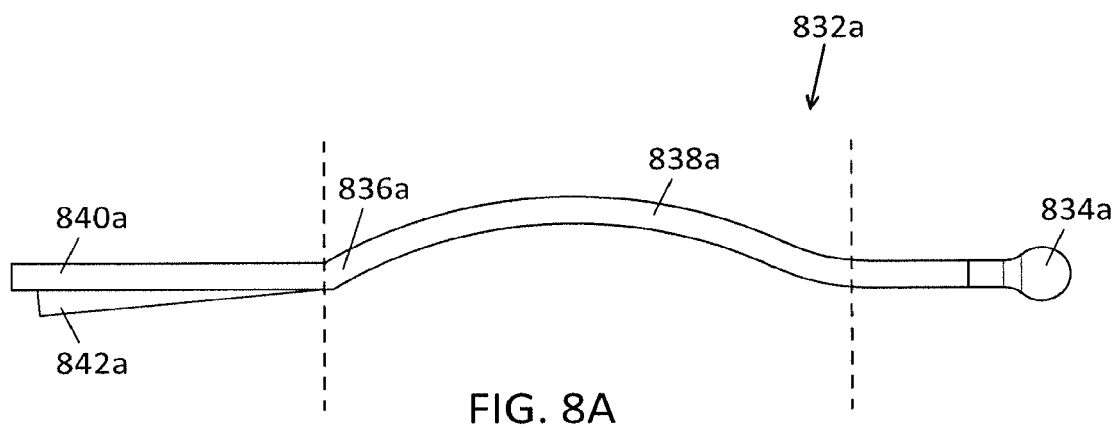
FIGS. 8A-8B show additional embodiments of nasal implants that can have modified stiffness.
Figure 8B:
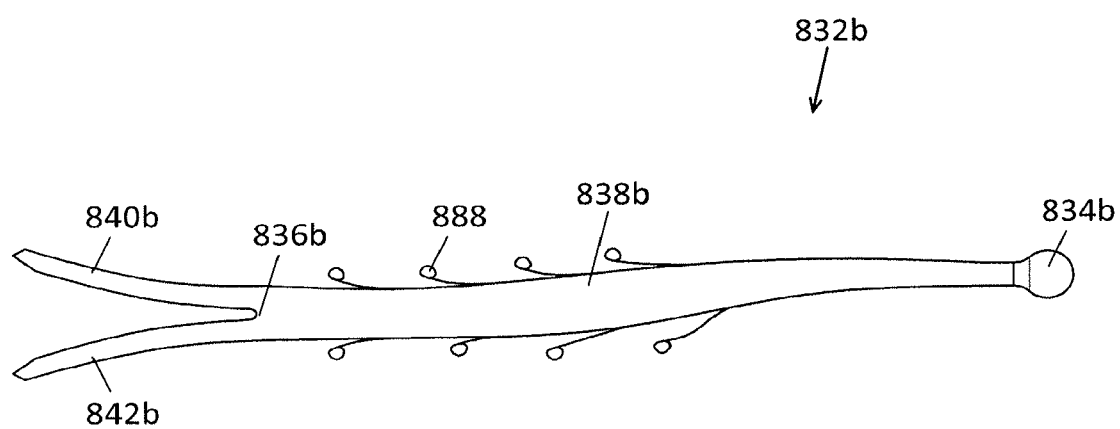

FIGS. 8A-8B illustrate additional embodiments of nasal implants. As shown in FIG. 8A, a nasal implant 832a can have a central body 838a, an atraumatic proximal end 834a, and a distal end 836a with two forked arms 840a, 842a. The central body 838a can have a curve along the longitudinal axis thereof. Thus, the forked distal end 836a can be adapted to overlie the nasal bone, the curved central body 838a can be adapted to overlie the upper lateral cartilage (ULC), and the proximal end 834a can be adapted to engage with the lower lateral cartilage (LLC) to stent open or add support to the nasal valve. As shown in FIG. 8B, a nasal implant 832b can have a central body 838b, an atraumatic proximal end 834b, and a distal end 836b with two forked arms 840b, 842b. The central body 838b can have tissue ingrowth features 888, such as webs or flaps. In some embodiments, the tips of the features 888 can be annular and/or hollow. The ingrowth features 888 can allow rapid tissue ingrowth when the implant 832b is implanted into the body. Further, the stiffness of the implants 832a,b can be tailored by removing material form certain locations of the implant.

Figure 9A:
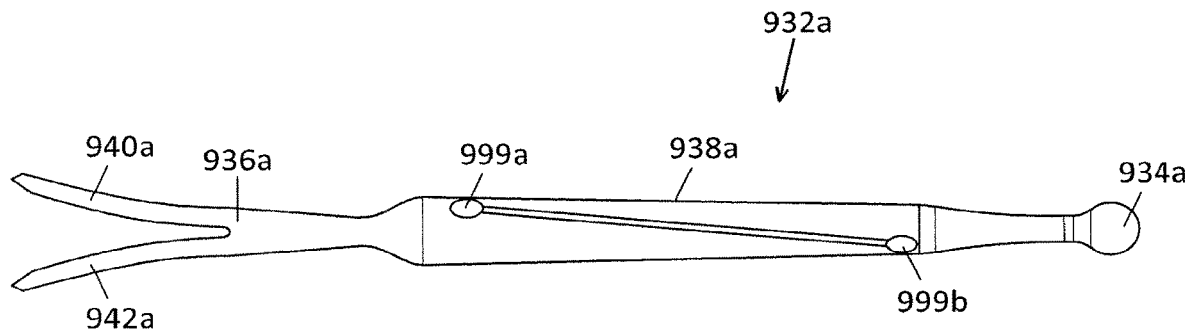
FIGS. 9A-9C show additional embodiments of nasal implants that can have modified stiffness.
Figure 9B:
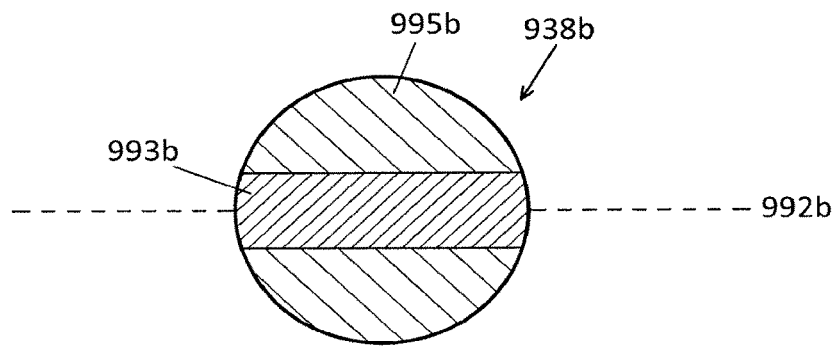
Figure 9C:
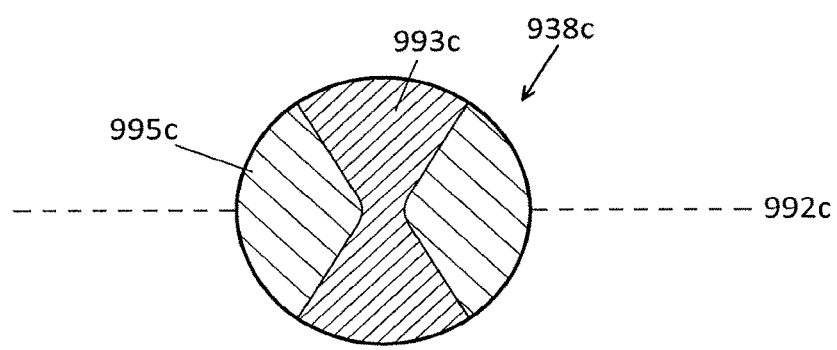

FIGS. 9A-9C illustrate additional embodiments of nasal implants. As shown in FIG. 9A, a nasal implant 932a can have a central body 938a, an atraumatic proximal end 934a, and a distal end 936a with two forked arms 940a, 942a. The central body 938 can have a first through-hole 999a therein near the distal end 936a and a second through-hole 999b therein near the proximal end. In some embodiments, an open slit or hole can extend between the holes 999a,b. In other embodiments, the holes 999a,b can be used to create tension with sutures. In some embodiments, a different material can be overmolded through the holes 999a,b and between the holes 999a,b. Referring to FIGS. 9B and 9C, in some embodiments, the nasal implants can have a composite structure. As shown in FIG. 9B, the central body 938b can have a first material 993b can be layered between a second material 995b. The first material 993b can be stiffer than the second material 995b. As shown in FIG. 9B, the layer of first material 993b can be rectangular or flat and can extend in the same plane 992b as the two arms of the implant. As shown in FIG. 9C, in some embodiments, the first material 993c (e.g., the stiffer material) can be in an hourglass-shape between the second material 995c. In some embodiments, the second material 995b,c can be configured to degrade more quickly than the first material 993b,c.

FIGS. 10A-10B illustrate embodiments of nasal implants made of a composite structure. As shown in FIG. 10A, a nasal implant 1032a can have a central body 1038a, an atraumatic proximal end 1034a, and a distal end 1036a with two forked arms 1040a, 1042a. The implant 1032a can further include a central core 1010a extending the length of the implant (e.g., along the longitudinal axis) that is filled with or made of a different material than the rest of implant 1032a. For example, the central core 1010a can be a core pin material that includes directionally oriented fibers or a stiffer material inserted therethrough. The stiffness of the implant 1032a can be varied by selecting a desired core material with the desired stiffness. As shown in FIG. 10B, in some embodiments, the core 1010b can wrap around and/or through the central portion 1038b at an angle. The position and angle of the core 1010b can vary the stiffness of the nasal implant 1032b.

FIG. 17 illustrates a nasal implant with a stiffness that varies along the central longitudinal portion of the implant. The implant 1732 can have a central body 1738, an atraumatic proximal end (not shown), and a distal end 1736 with two forked arms 1740, 1742. The central body 1738 can have a proximal portion 1771 and a distal portion 1772 of differing stiffnesses. The proximal portion 1771 can be solid while the distal portion 1772 can have a pattern thereon. The patterned distal portion 1772 can include material removed from the central body 1738. If the patterned section consists of material that is removed or etched from the central body 1738, then the stiffness of distal portion 1772 would be decreased relative to the stiffness of proximal portion 1771. In some cases, the patterned section can have material molded along the patterned area to create a thickness that is greater than the thickness D at other portions of the implant. The overmolded or increased thickness of the pattern can increase the stiffness of portion 1772 as compared to the stiffness of portion 1771. In some cases, the overmolded material can be a different material than the bulk of the nasal implant 1732. Thus, a composite implant could be used having two or more different materials. The material for the patterned portion of the nasal implant 1732 can be selected to achieve a desired stiffness and/or degradation rate of the implant 1732.

Figure 18:
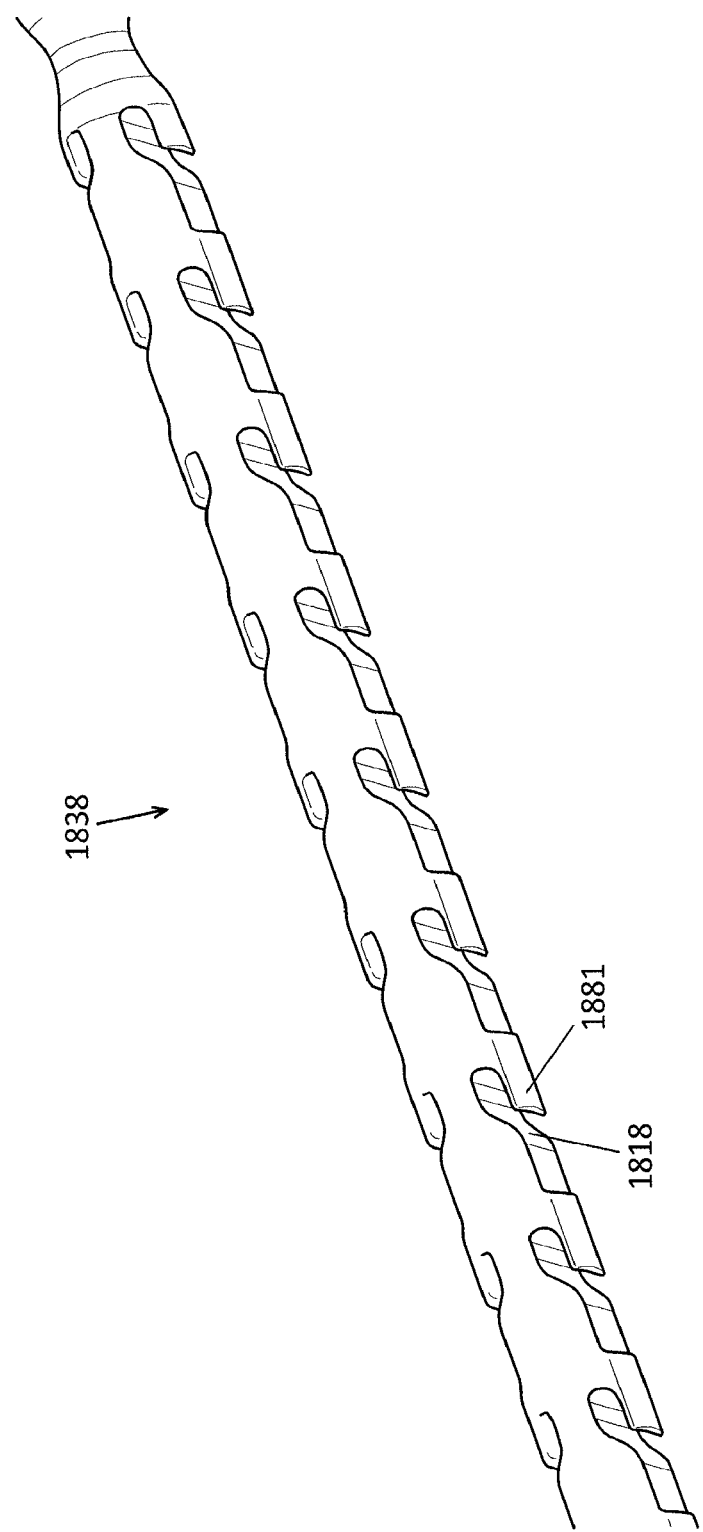
FIG. 18 shows the central body of a nasal implant that includes a combination of grooves and barbs.

FIG. 18 illustrates the central body of a nasal implant with preferential stiffness having a combination of grooves and barb like features. The central body 1838 has a flattened shape with diagonal grooves 1818 extending through. The angle of the diagonal grooves 1818 can form sharp barbs 1881 on the edge of the elongate body 1838. The illustrated central body 1838 can have maximum stiffness in the plane parallel to the forks/arms of the nasal implant while increasing the flexibility in the plane perpendicular to the forks/arms. The grooves 1818 and barbs 1881 can also reduce the likelihood of migration of the nasal implant and improve tissue ingrowth.

FIG. 19 illustrates a nasal implant with modified stiffness along at least one axis. The implant 1932 can have a central body 1938, an atraumatic proximal end 1934, and a distal end 1936 with two forked arms 1940, 1942. The central body 1938 has a flattened shape with a series of scalloped features 1919 along the edges. The scalloped features 1919 can reduce stiffness of the implant along one axis, such as the axis parallel to the plane of the arms 1940, 1942. The scalloped features 1919 can also reduce the likelihood of migration of the nasal implant.

Figure 21:
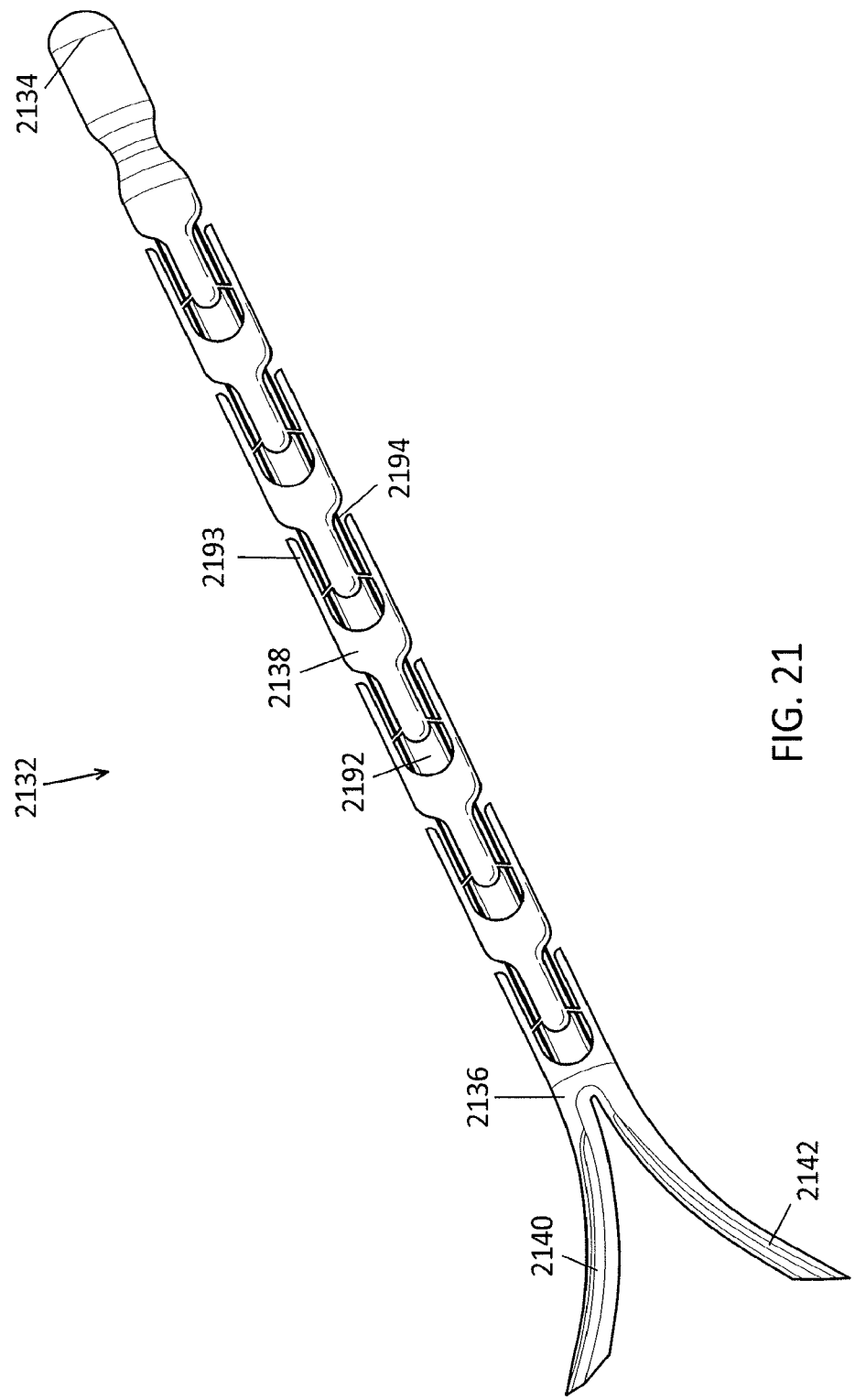
FIG. 21 shows a nasal implant with an overmolded pattern that provides modified stiffness.

FIG. 21 illustrates a nasal implant with modified stiffness. The implant 2132 can have a central body 2138, an atraumatic proximal end 2134, and a distal end 2136 with two forked arms 2140, 2142. Further the central body 2138 can have a central core 2192, for example a poly-L-lactide (PLLA) core, with an overmolded pattern thereover. The pattern can include barbs 2193 and grooves 2194 therebetween. The barbs 2193 can be compressible relative to the core 2192. The central body 2138 can articulate or bend at the grooves 2194 until the gaps between adjacent barbs (i.e., the grooves) are closed and adjacent barbs 2193 are in contact with one another. When the adjacent barbs 2193 are in contact with one another, then the stiffness of the nasal implant 2132 greatly increases. The overmolded design of the implant 2132 allows for multiple materials to be used with different physical properties and degradation rates.

Figure 22A:
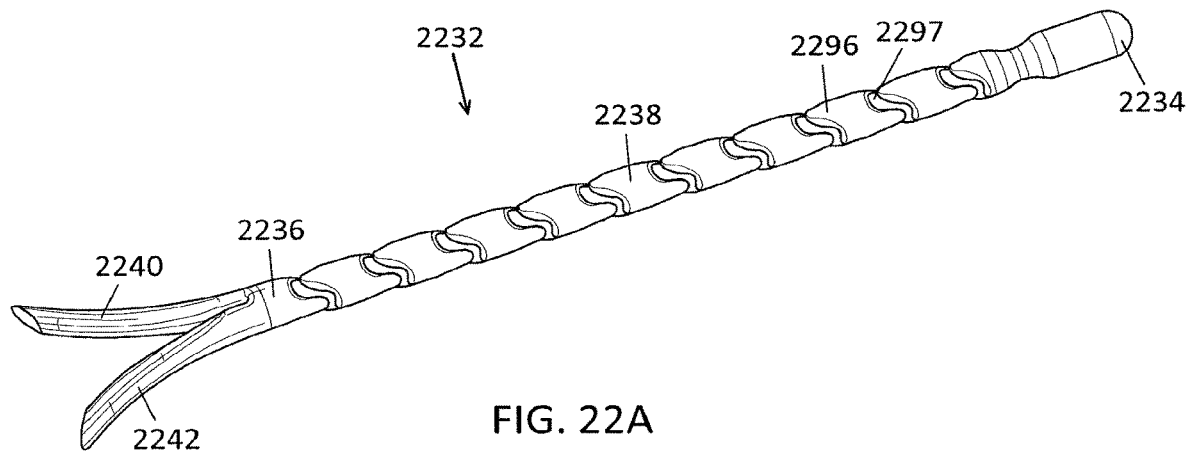
FIGS. 22A-22C show a nasal implant that includes articulating sections.
Figure 22B:
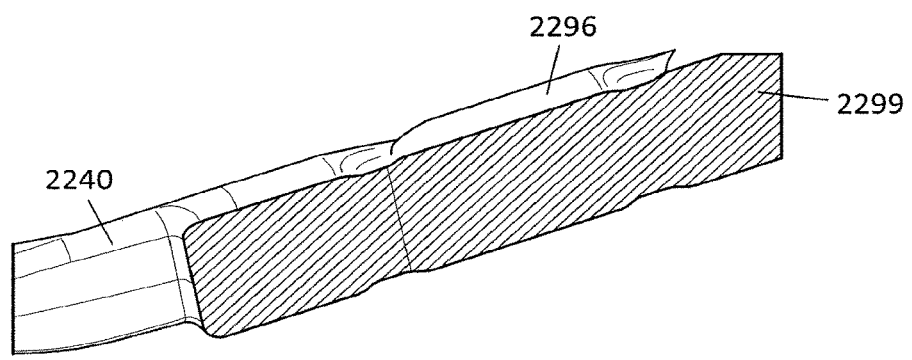
Figure 22C:
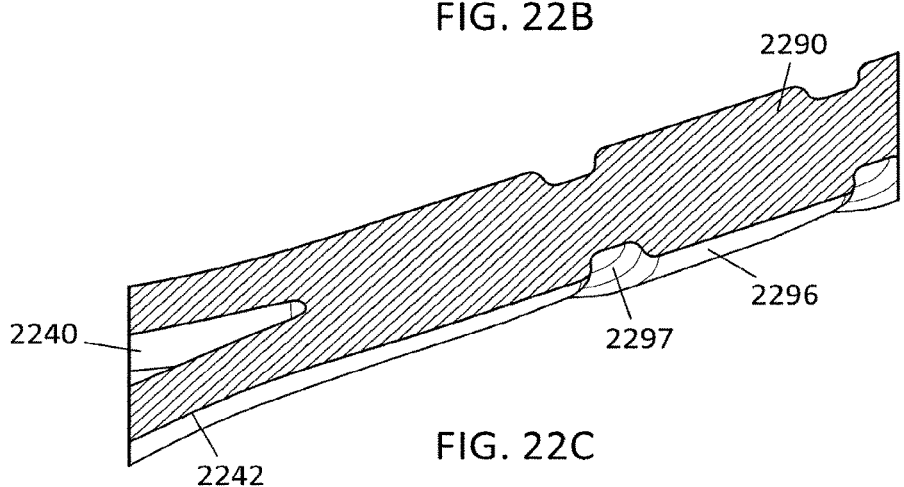

FIGS. 22A-22C illustrate another nasal implant with modified stiffness. The nasal implant 2232 can have a central body 2238, an atraumatic proximal end 2234, and a distal end 2236 with two forked arms 2240, 2242. The central body 2238 has non-uniform axial thickness including a core 2299 and a plurality of segments 2296 extending thereover.

The segments 2296 can have grooves 2297 or gaps therebetween. The central body 2238 can flex until the gaps between adjacent segments 2296 closes. The grooves 2297 thus allow for some articulation or reduced stiffness in some directions. The implant 2232 can remain in an elastic deformation region where the effective diameter is more slender when a large deflection forces the implant to bend to close the gap between adjacent segments 2296. Once the gap closes, the stiffness can increase significantly to prevent or reduce further bending.

Figure 23:
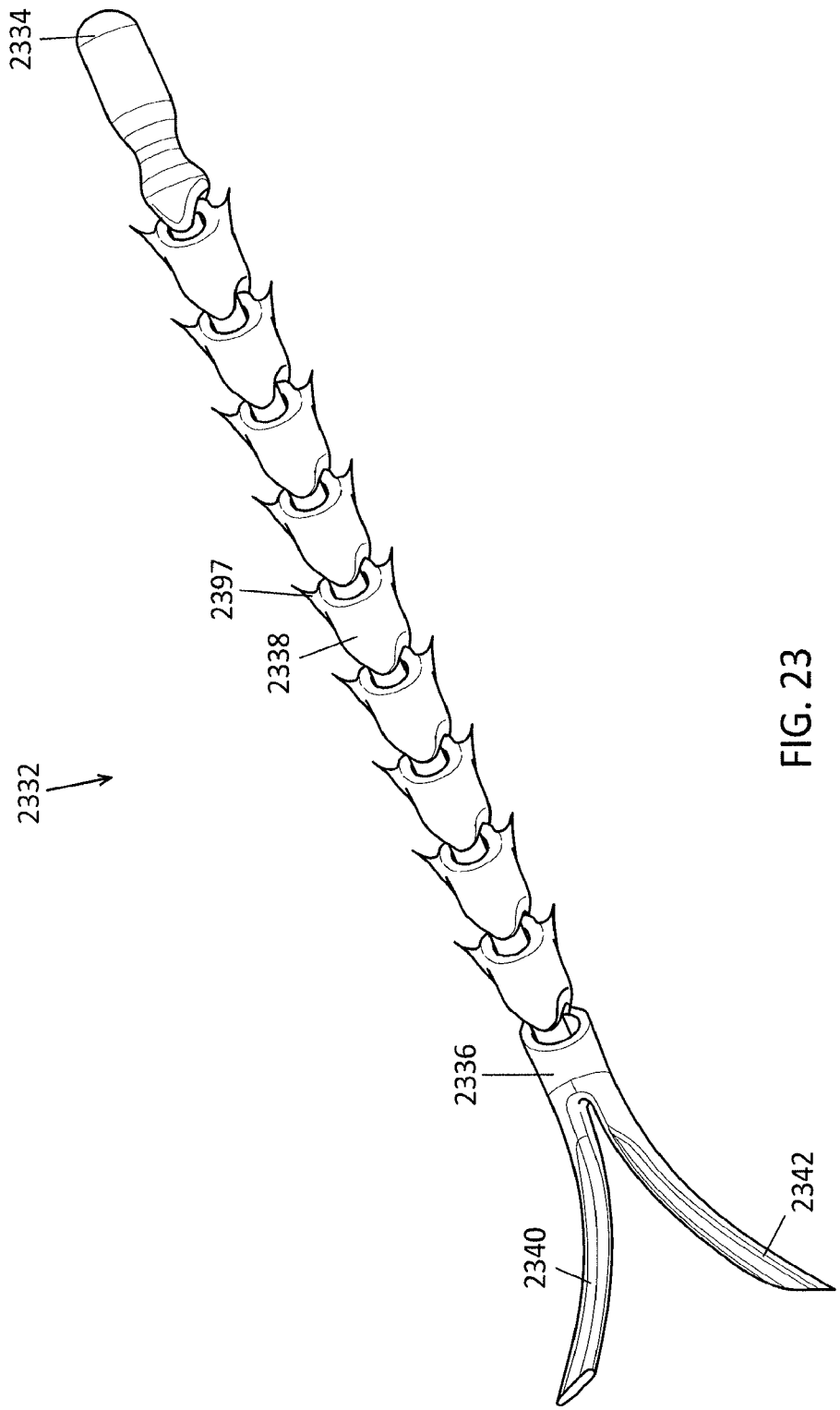
FIG. 23 shows a nasal implant including barbed segments.

FIG. 23 illustrates another nasal implant with modified stiffness. The nasal implant 2332 can have a central body 2338, an atraumatic proximal end 2334, and a distal end 2336 with two forked arms 2340, 2342. The central body 2338 includes linked conical-shaped segments 2397 that can aid in flexibility of the body 2338. Further, the proximal ends of the segments 2397 can have barbs extending therefrom to improve tissue engagement and reduce migration of the implant.

FIGS. 24A-24B illustrate another nasal implant with modified stiffness. The nasal implant 2432 can have a central body 2438, an atraumatic proximal end 2434, and a distal end 2436 with two forked arms 2440, 2442. The central body 2438 can have a laser cut cylindrical pattern thereon. Laser cutting can facilitate the formation of unique geometries for the nasal implant 2432 with tailored physical properties, such as axial compression and stiffness. The illustrated pattern allows for axial compression without losing the bending ability of the cylindrical central body 2238 of the nasal implant 2432.

FIG. 25 illustrates another nasal implant with modified stiffness. The nasal implant 2532 can have a central body 2538, an atraumatic proximal end 2534, and a distal end 2536 with two forked arms 2540, 2542. The central body 2538 is cylindrical with a helical grooved scallop 2552 running therearound that can increase the flexibility of the central body 2538.

FIGS. 26A-26F illustrate additional nasal implants having central bodies with different patterns and different textures for modified stiffness. For example, the implant 2632a of FIGS. 26A-26B has a central body 2638a, an atraumatic proximal end 2634a, and a distal end 2636a with two forked arms 2640a, 2642a. The central body 2638a is smooth without any ribs except for a transitional area 2662a near the proximal end 2634a. The transitional area 2662a includes a stepped tapered section and a series of grooves that contribute to the flexibility of the proximal portion of the implant 2632a. The implant 2632b of FIGS. 26C-26D has a central body 2638b, an atraumatic proximal end 2634b, and a distal end 2636b with two forked arms 2640b, 2642b. The central body 2638b has a series of scallops 2666b thereon that are configured as smooth waves. The scallops 2666b can provide increased flexibility to the implant 2632. The implant 2632c of FIGS. 26E-26F has a central body 2638c, an atraumatic proximal end 2634c, and a distal end 2636c with two forked arms 2640c, 2642c. The central body 2638c has a series of scallops 2666c thereon. The scallops 2666c are at a steeper angle than the scallops 2666b and can provide flexibility to the central body 2638c.

FIGS. 27A-F illustrate additional embodiments of nasal implants having central bodies with different patterns and different textures for modified stiffness. For example, the implant 2732a of FIGS. 27A-27B has a central body 2738a, an atraumatic proximal end 2734a, and a distal end 2736a with two forked arms 2740a, 2742a. The central body 2738a has two scalloped regions 2772a,b separated by a central region 2773 with a smooth outer surface. The scalloped regions 2772a,b can provide flexibility towards the proximal and distal ends 2734a, 2736a while maintaining a stiffer central region 2773. The implant 2732b of FIGS. 27C-27D has a central body 2738b, an atraumatic proximal end 2734b, and a distal end 2736b with two forked arms 2740b, 2742b. The implant 2732b is similar to implant 2732a except that implant 2732b includes three scalloped sections 2774a,b,c separated by two regions 2775a,c with smooth outer surfaces. The three scalloped sections 2774a,b,c can provide for increased flexibility relative to the two regions 2775a,c. The implant 2732c of FIGS. 27E-27F has a central body 2738c, an atraumatic proximal end 2734c, and a distal end 2736c with two forked arms 2740c, 2742c. The central body 2738c includes a scalloped region while the transition from the central body 2738c to the proximal end 2734c is of smooth and of substantially constant diameter (rather than tapered as with many of the implant designs described herein), resulting in a stiffer proximal portion of the implant 2732c.

FIGS. 34A-34B illustrate another nasal implant with modified stiffness. The nasal implant 3432 can have a central body 3438, an atraumatic proximal end 3434, and a distal end 3436 with two forked arms 3440, 3442. The central body 3438 has flattened surfaces 3443 on two (opposite) sides and scalloped or ridged surfaces 3444 therebetween. The flattened surfaces 3443 effectively reduce the thickness of the implant 3432 along that dimension/axis, which can provide greater flexibility for the nasal implant about that axis. The nasal implant 3432 has a constant thickness along the axis for flexing that can result in distributing the stress more uniformly when the implant flexes. In some embodiments, other configurations can be used, such as one flattened surface, more than two flattened surfaces, or flattened surfaces on adjacent sides.

Figure 28:
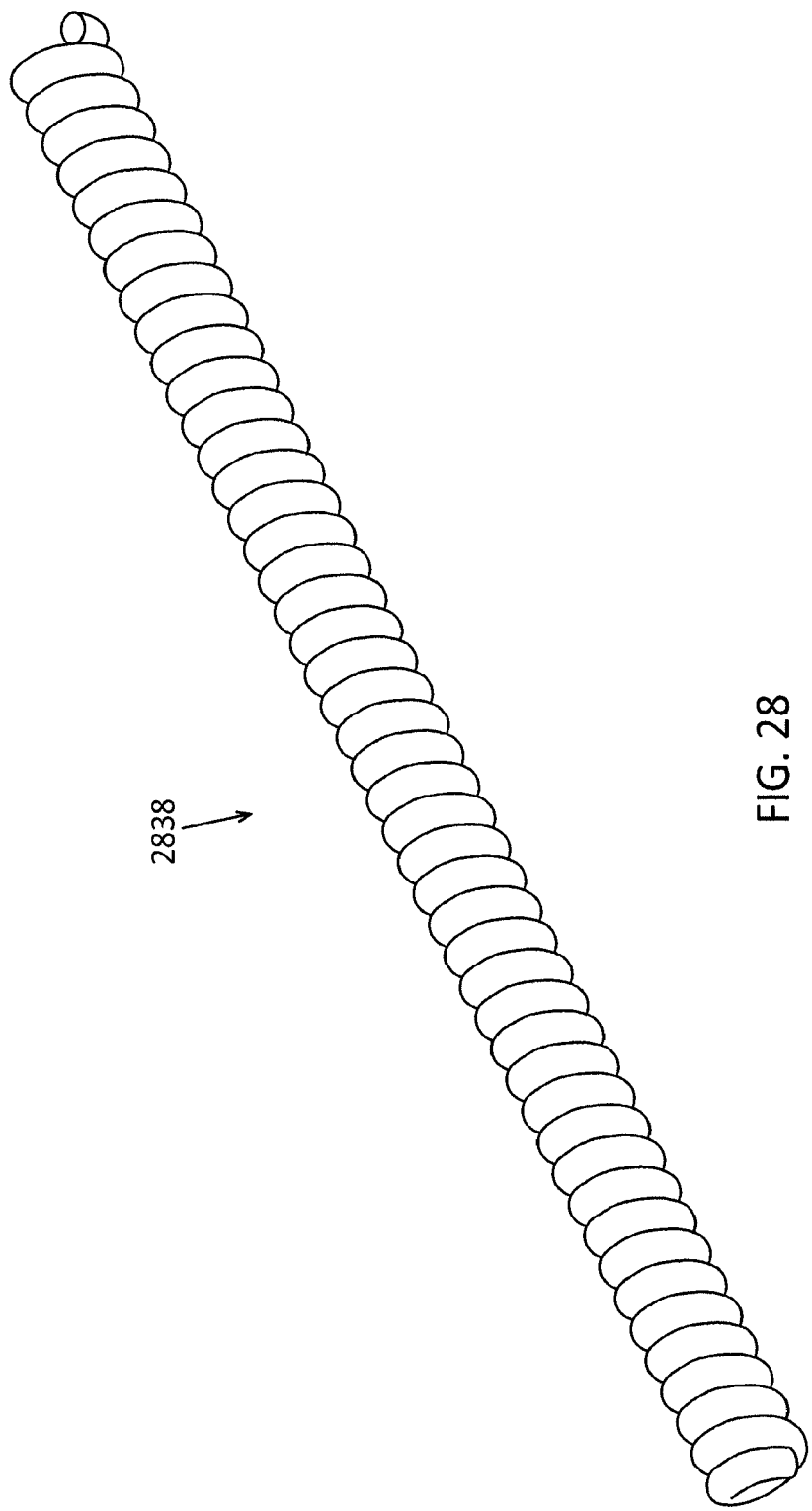
FIG. 28 illustrates a central body of nasal implant that includes a closed pitch spiral shaft.
Figure 29:
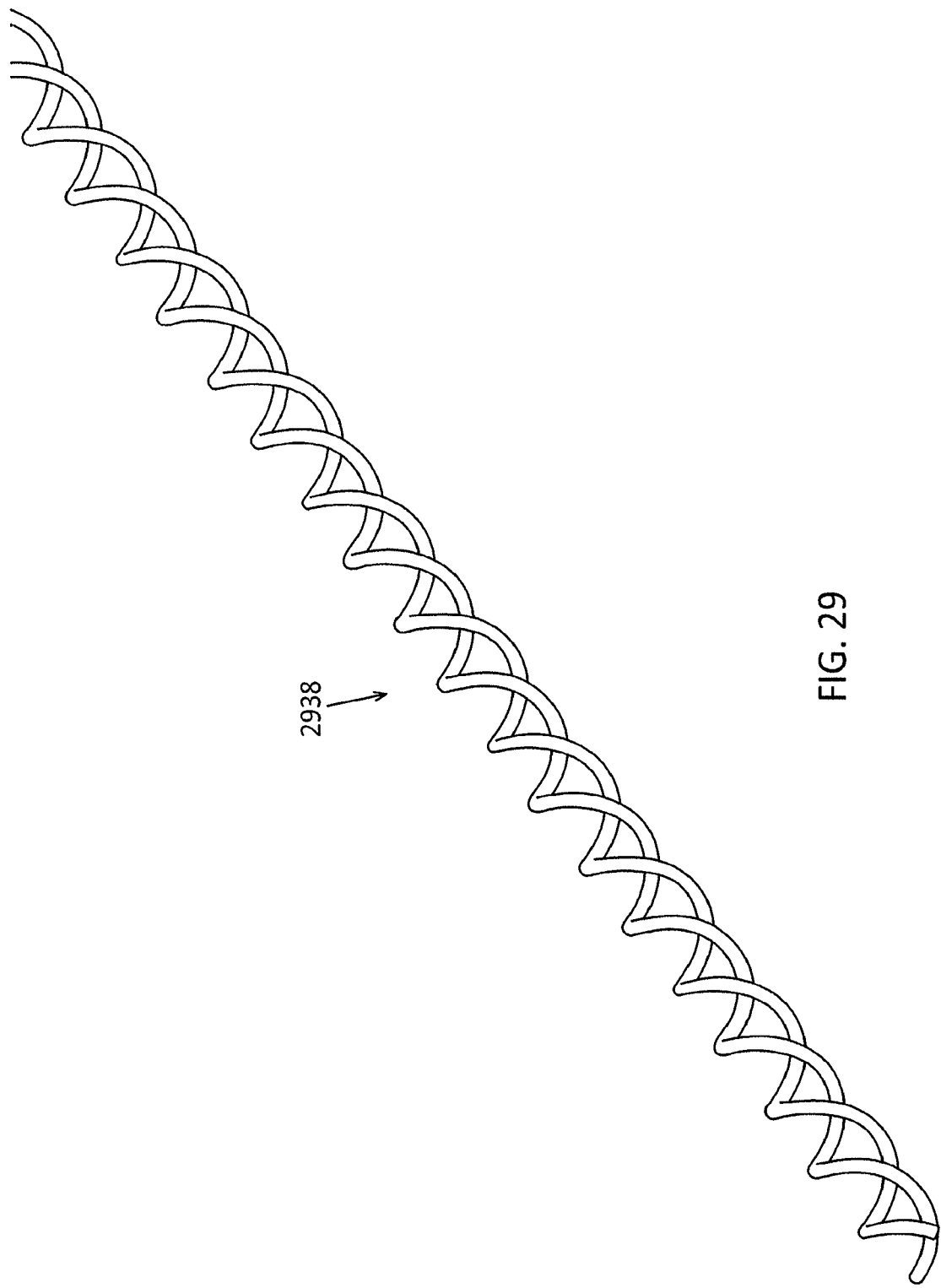
FIG. 29 illustrates a central body of a nasal implant with a uni-directional helix spiral shaft.
Figure 30:
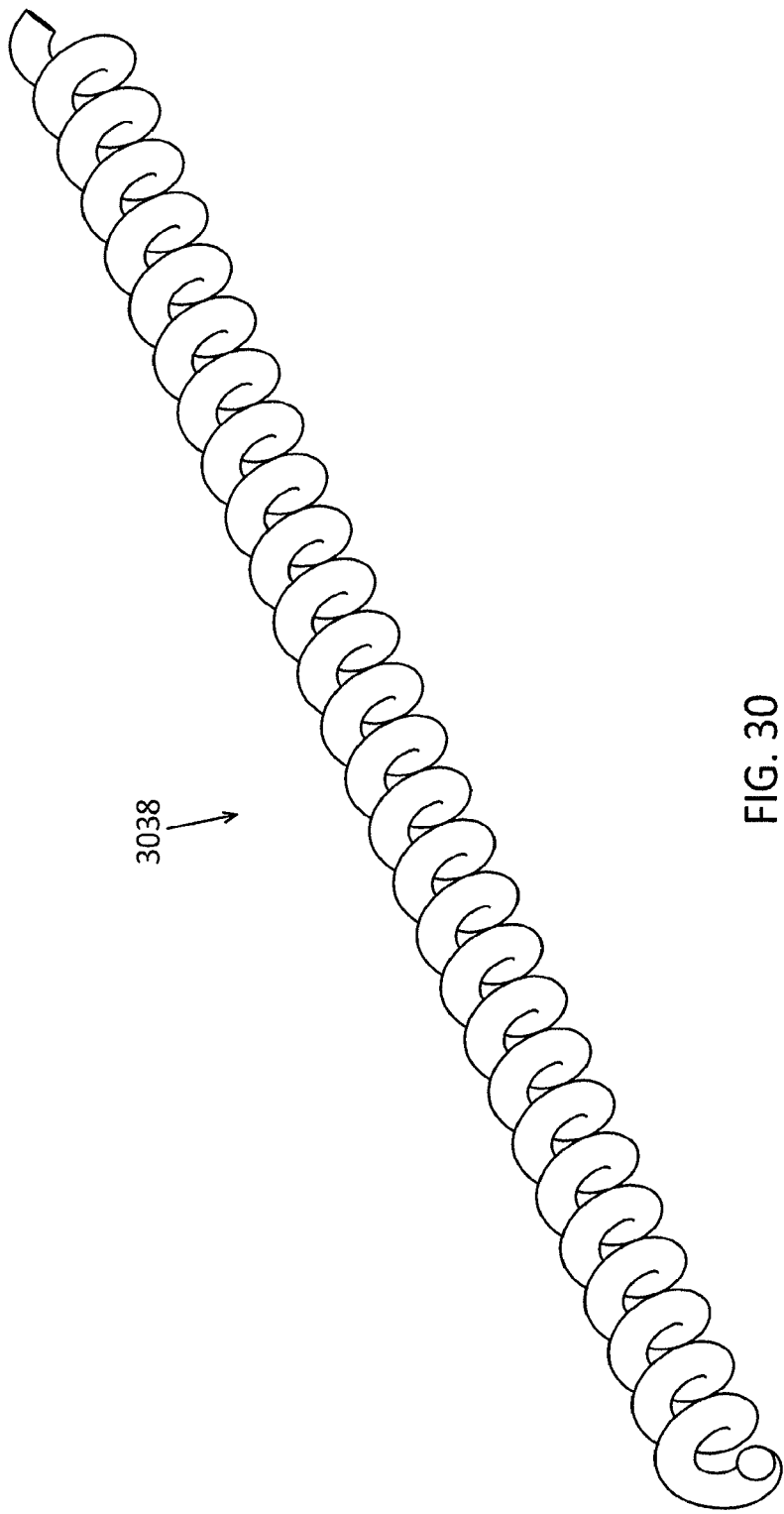
FIG. 30 illustrates a central body of a nasal implant with an open coil shaft.
Figure 31:
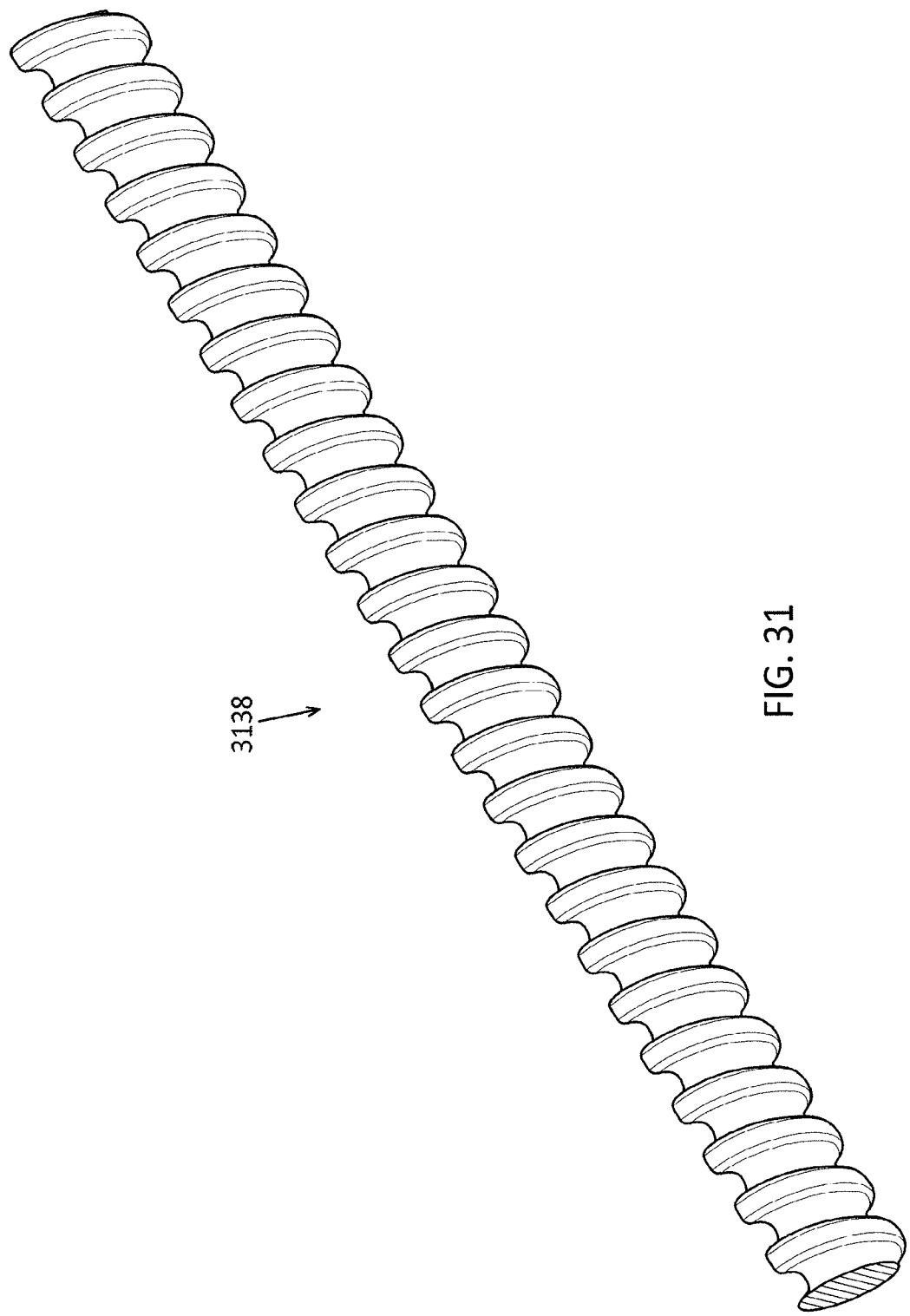
FIG. 31 illustrates a central body of a nasal implant with a solid shaft and a spiral outer cut in the surface.
Figure 32:
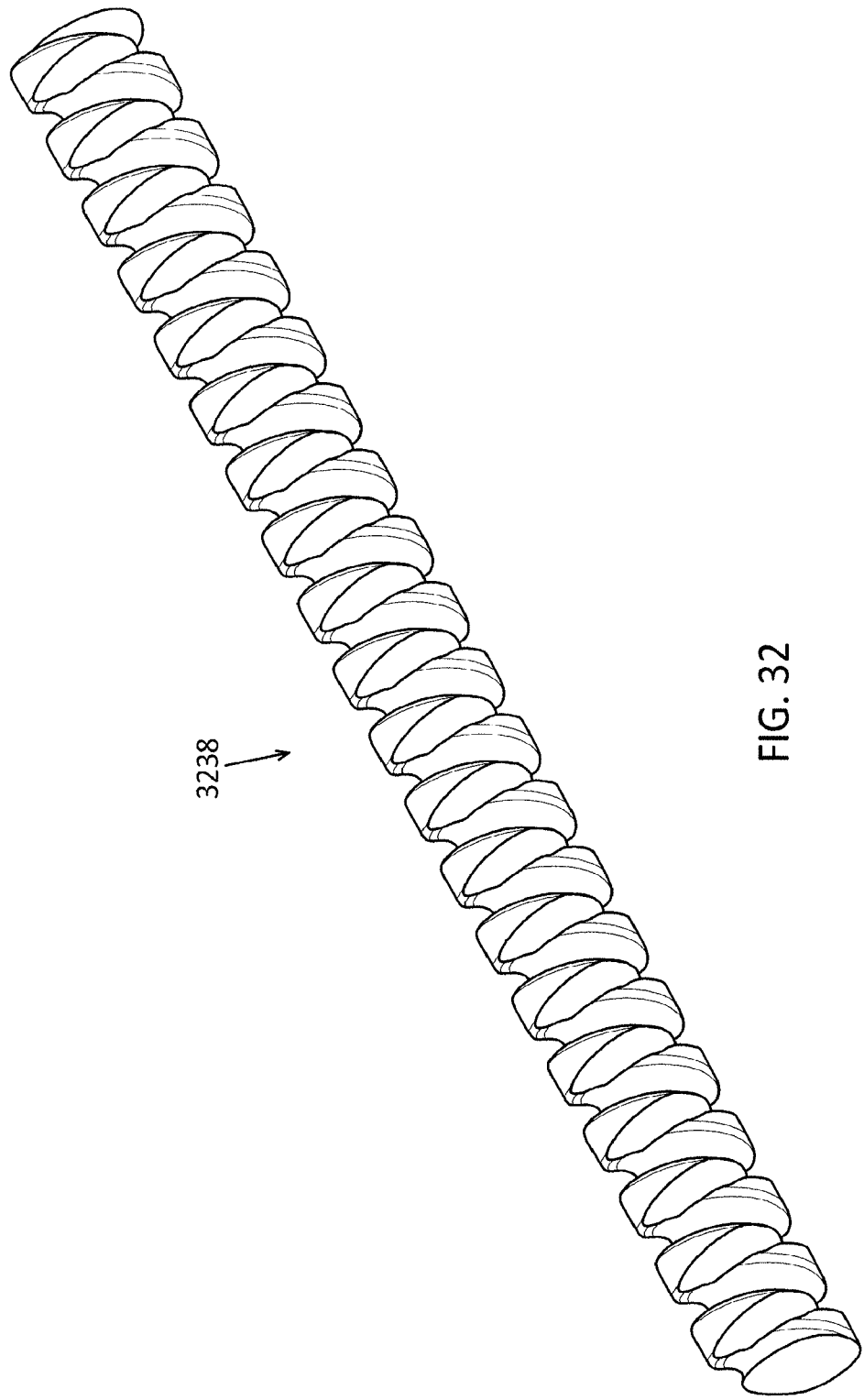
FIG. 32 illustrates a central body of a nasal implant that includes a solid shaft having a dual, bi-directional spiral cut.
Figure 33:
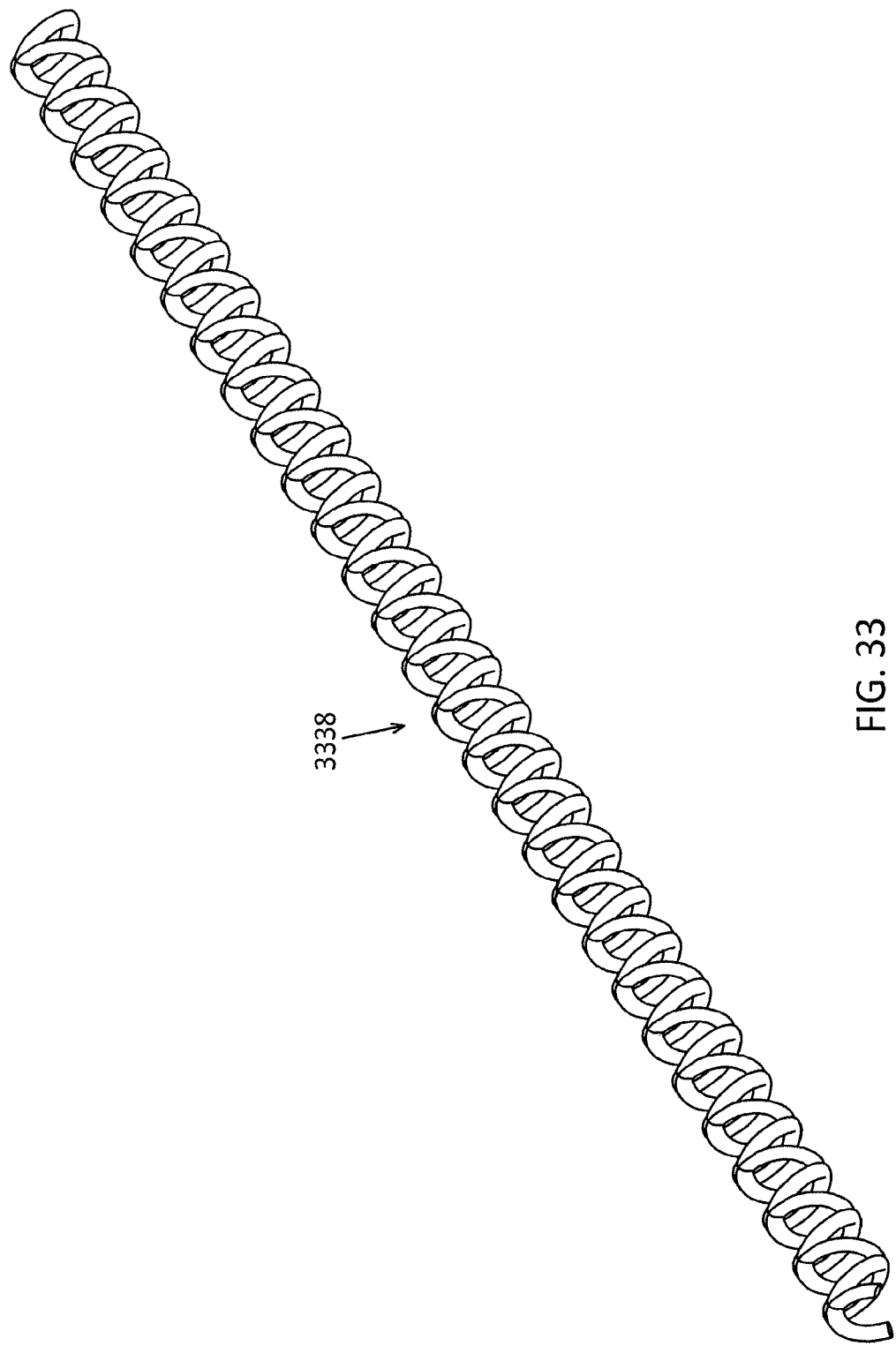
FIG. 33 illustrates a central body of a nasal implant that includes a bi-directional helix spiral shaft.

FIGS. 28-33 illustrate various structures that can be used as the central body of the nasal implants described herein to provide the desired stiffness and flexibility for that portion of the nasal implant. FIG. 28 illustrates a central body 2838 of a nasal implant with a closed pitch spiral shaft. FIG. 29 illustrates a central body 2938 of a nasal implant with a uni-directional helix spiral shaft. FIG. 30 illustrates a central body 3038 of a nasal implant with an open coil shaft, which can not only increase flexibility, but also facilitate tissue ingrowth within the central body. FIG. 31 illustrates a central body 3138 of the nasal implant with a solid shaft and a spiral outer cut in the outer surface of the central body 3138. FIG. 32 illustrates a central body 3238 of a nasal implant that includes a solid shaft having a dual, bi-directional spiral cut. FIG. 33 illustrates a central body 3338 of a nasal implant that includes a bi-directional helix spiral shaft, which can not only increase flexibility, but also facilitate tissue ingrowth within the central body. In some embodiments, the chosen central body configuration can also tailor the degradation profile of the implant.

Figure 56A:
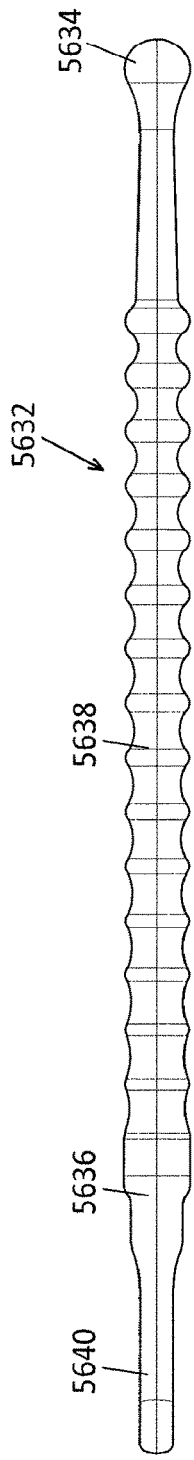
FIGS. 56A-56C show a nasal implant with an outer undulating pattern for modified stiffness.
Figure 56B:
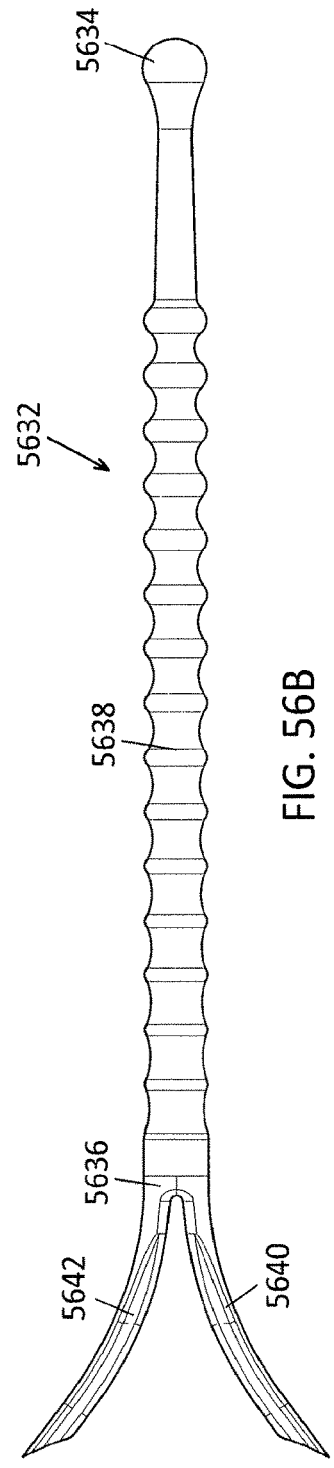
Figure 56C:
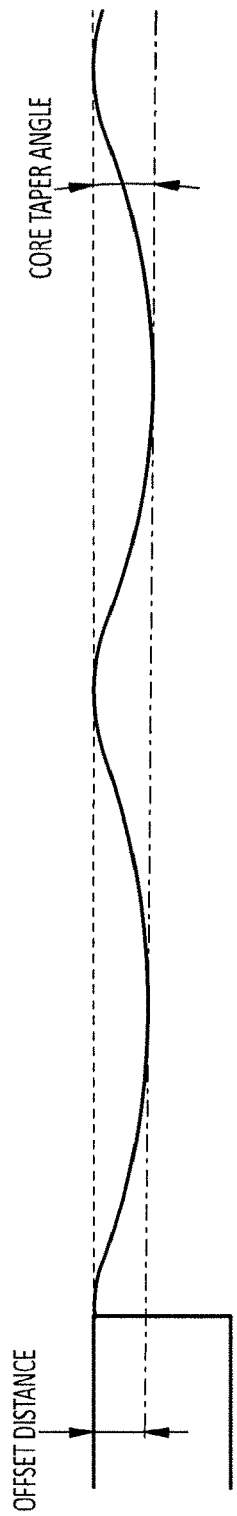

FIGS. 56A-56C illustrate a nasal implant with another embodiment of a central body. The nasal implant 5632 can have a central body 5638, an atraumatic proximal end 5634, and a distal end 5636 with two forked arms 5640, 5642. The central body 5638 can have a substantially constant repeating and undulating pattern in an outer material over an inner core that is tapered along the length of the core. Various taper angles can be used with the inner core material to optimize the stiffness of the implant and minimize stress during implant bending. Further, the taper can start at different positions to minimize stress during implant bending. The taper angle, inner core configuration, and offsets can be selected to achieve a desired stiffness profile and stress profile during implant bending.

Figure 57C:
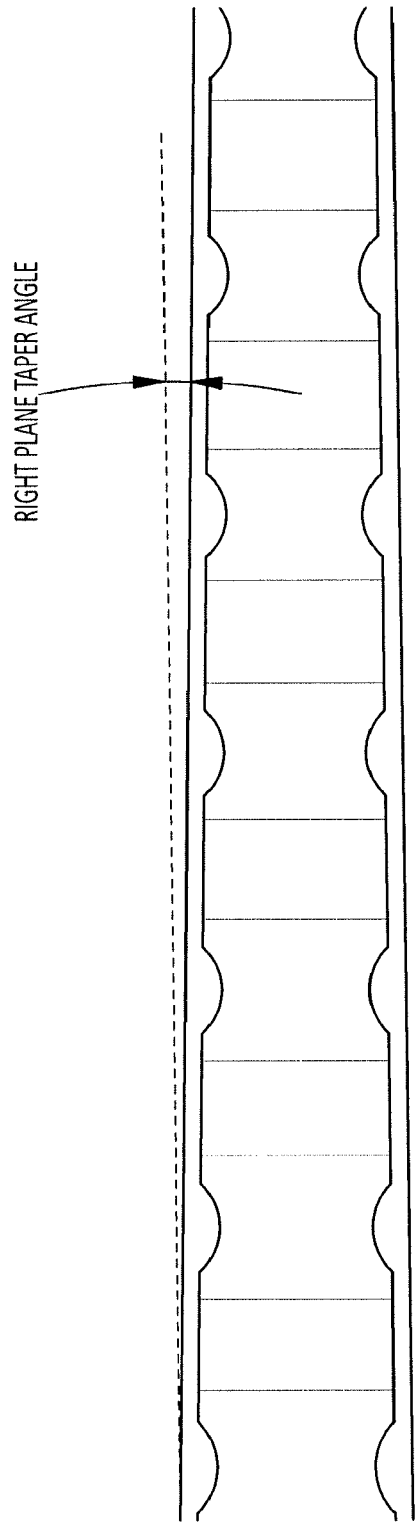
Figure 57D:
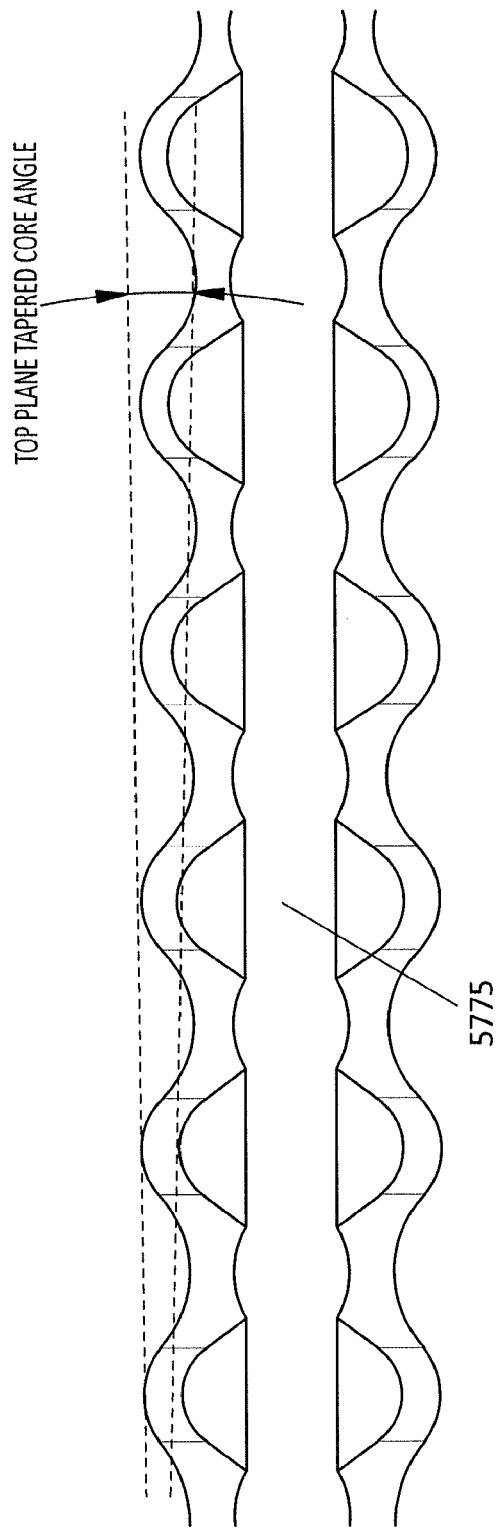

FIGS. 57A-57D illustrate an embodiment of a nasal implant with a multiplane tapered configuration. The nasal implant 5732 includes a central body 5738, an atraumatic proximal end 5734, and a distal end 5736 with two forked arms 5740, 5742. The central body 5738 includes a flat taper in one plane, a tapered core in a second plane, and stress distribution rib 5757 along a length of the implant in the first plane top and bottom of the implant. Additionally, a stress distribution rib 5757 can be used along the flat taper to improve the stress distribution along the length of the implant. The stress distribution rib 5757 can be along multiple portions of the implant. In some cases, the stress distribution rib 5757 can be used on opposing surfaces of the length of the implant. The stress distribution rib 5757 can have a discontinuous configuration. The illustrated stress distribution rib 5757 can have one or more bearing feature 5775 therebetween. The bearing feature 5775 can facilitate delivery tool interactions, such as delivery and deployment. A multitude of taper angles, starting taper offsets, and rib geometries can be used to achieve a desired or pre-selected stiffness of the implant while also minimizing the stress during bending. FIG. 57C is a side-profile view showing the right plane taper angle, and FIG. 57D is a top-down view showing the top plane tapered core angle.

FIGS. 58A-C illustrate an embodiment of a nasal implant with a generally tapered outer diameter. The nasal implant 5832 includes a central body 5838, an atraumatic proximal end 5834, and a distal end 5836 with two forked arms 5840, 5842. The central body 5838 has a taper along the length thereof and a tapered inner core. The inner core and outer material can have a matching taper angle or different taper angles. A variety of different taper angles can be used to achieve the desired stiffness and bending properties of the implant. A multitude of taper angles and starting taper offsets can be used to achieve a desired or pre-selected stiffness of the implant while also minimizing the stress during bending. The bearing features 5875 can facilitate delivery tool interactions such as delivery and deployment. FIG. 58C shows the outer diameter taper angle of the implant 5832.

In some embodiments, a treatment can be used to modify the properties of the exterior of the nasal implants described herein. For example, a plasma treatment on the surface of the nasal implant can impart hydrophilic properties to the implant. Plasma treatments can also be used to attach or adsorb functional groups to change the water ingress and therefore the degradation profile of the nasal implant. Further, plasma treatments can be used to crosslink polymers on the surface of the implant to preferentially change one or more of the degradation profile, tissue response, tissue adhesion, and hydrophobicity of the nasal implant. The plasma treatment can also be used to modify the surface of the nasal implant to act as a protective layer to the bulk bioresorbable material. As another example, plasma polymerization can be used to deposit a higher molecular weight layer on a nasal. Plasma can be used to attach functional polymers or end groups onto plasma activated surfaces of the implant. In some embodiments, the plasma treatment can be used to prepare a surface of the nasal implant for a coating, such as a parylene coating, to enhance adhesion between an interior bioresorbable polymer and the parylene coating.

Figure 11:
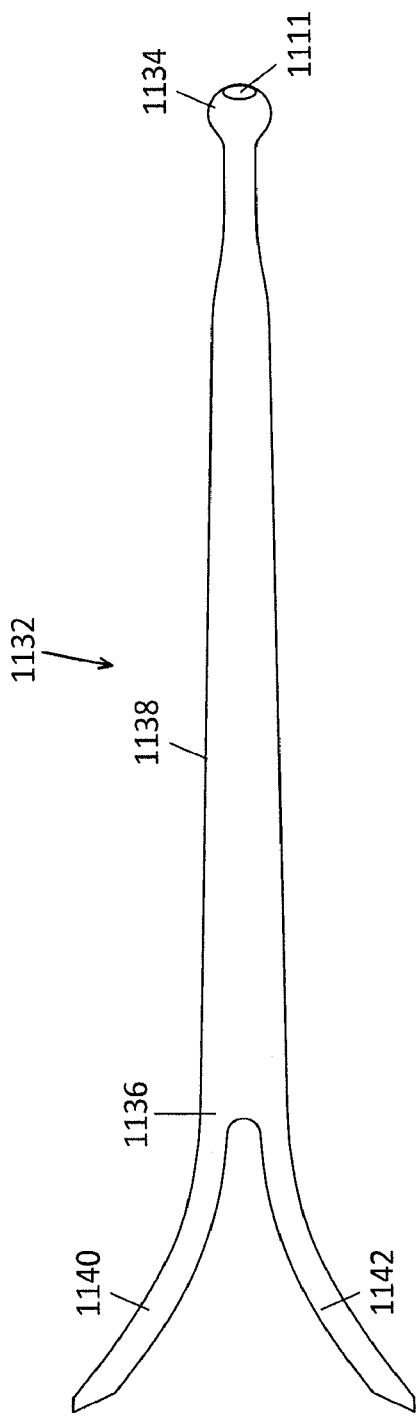
FIG. 11 shows a nasal implant having a non-contiguous coating that can be used to tune the degradation profile of the implant.
Figure 12:
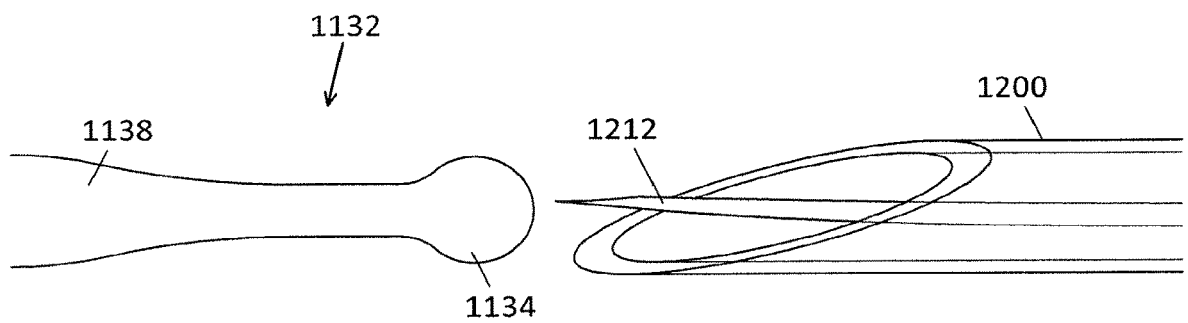
FIG. 12 shows an exemplary method of creating the coating on the implant of FIG. 11.

FIG. 11 illustrates a nasal implant 1132 having a central body 1138, an atraumatic proximal end 1134, and a distal end 1136 with two forked arms 1140, 1142. The implant 1132 can have a non-contiguous coating, such as a coating of parylene, on the exterior thereof that can be used to tune the degradation profile of the implant 1132. In some embodiments, the coating can cover all of the implant 1132 except an opening 1111 at the proximal end 1134. The opening can allow fluid ingress to facilitate the degradation of the implant 1132. FIG. 12 illustrates an exemplary method of creating the opening 1111. As shown, a delivery tool 1200 can include a needle 1212 therein. The needle 1212 can be used to puncture the proximal end 1134, thereby puncturing the exterior coating and thereby tuning the degradation of the implant 1132.

In some embodiments, the nasal implants described herein can be modified to reduce the likelihood of implant ejection, migration, and motion in the first few weeks after implantation by promoting tissue ingrowth. For example, a treatment, such as a plasma treatment, can be applied to the outer surface of the implant to reduce the likelihood of implant ejection, migration, and motion during the implantation of the nasal implant. As another example, the implant can have hollow sections configured to provide for tissue ingrowth. As another example, barbs or wings that unfold can be used to dig into tissue and/or promote tissue ingrowth.

If barbs are used, the barbs can have varying geometries and configurations, such as any of the barbs disclosed herein. The barbs can improve the nasal implant's engagement with the tissue after implantation as well as improve tissue ingrowth. The barbs can have varying sizes. In some embodiments, the barbs can be tiny and can improve tissue engagement to prevent withdrawal of the nasal implant after implantation. The nasal implants can be configured to be inserted through a portion of the upper lateral cartilage, inserted lateral to or on top of the upper lateral cartilage or to be inserted underneath the upper lateral cartilage. Features of the nasal implants in the expanded configuration post implantation can hold the rotational alignment of the nasal implant so that the stiffness and flexibility along different planes of the implant are somewhat fixed relative to the nasal anatomy and that the desired level of support is applied to the nasal valve.

The barbs can be configured to engage with soft tissue overlaying bony tissue proximal to the upper lateral cartilage. In some embodiments, a portion of the implant can be configured to engage with the upper lateral cartilage of the patient when the plurality of barbs are engaged with the soft tissue overlying the bony tissue proximal to the upper lateral cartilage.

Any barbs on the nasal implant can be designed such that the barbs can have a compressed delivery configuration within a cannula of the delivery tool and then fold out or expand after the nasal implant is delivered to the tissue to engage a portion of the targeted anatomy. The barbs can generally extend away from the forked end of the implant towards the proximal end or atraumatic end of the implant to prevent tissue migration.

The barbs can have different sizes and configurations. In some cases, the length of the barb can be expressed relative to a diameter of a portion of the implant. For example, the diameter of the portion of the implant can correspond to the diameter of the central longitudinal portion of the implant. For embodiments of the nasal implants with varying diameter along an axial length of the central longitudinal portion, the largest diameter of the central longitudinal portion can be used. In some cases, the diameter can correspond to the diameter of the implant in the compressed delivery configuration, such as when the nasal implant is within the cannula of the delivery device. In some embodiments, the barb has a length such that it extends from the surface of the nasal implant by a distance that is less than about 90% of the diameter of the portion of the implant. In some embodiments, the barb has a length such that it extends from the surface of the nasal implant by a distance that is less than about 80% of the diameter of the portion of the implant. In some embodiments, the barb has a length such that it extends from the surface of the nasal implant by a distance that is less than about 70% of the diameter of the portion of the implant. In some embodiments, the barb has a length such that it extends from the surface of the nasal implant by a distance that is less than about 60% of the diameter of the portion of the implant. In some embodiments, the barb has a length such that it extends from the surface of the nasal implant by a distance that is less than about 50% of the diameter of the portion of the implant. In some embodiments, the barb has a length such that it extends from the surface of the nasal implant by a distance that is less than about 40% of the diameter of the portion of the implant. In some embodiments, the barb has a length such that it extends from the surface of the nasal implant by a distance that is less than about 30% of the diameter of the portion of the implant. In some embodiments, the barb has a length such that it extends from the surface of the nasal implant by a distance that is less than about 25% of the diameter of the portion of the implant. In some embodiments, the barb has a length such that it extends from the surface of the nasal implant by a distance that is less than about 20% of the diameter of the portion of the implant. In some embodiments, the barb has a length such that it extends from the surface of the nasal implant by a distance that is from about 5% of the diameter of the portion of the implant to about 90% of the diameter of the portion of the implant. In some embodiments, the barb has a length such that it extends from the surface of the nasal implant by a distance that is from about 25% of the diameter of the portion of the implant to about 40% of the diameter of the portion of the implant. In some embodiments, the barb has a length such that it extends from the surface of the nasal implant by a distance that is from about 5% of the diameter of the portion of the implant to about 10% of the diameter of the portion of the implant.

Figure 13:
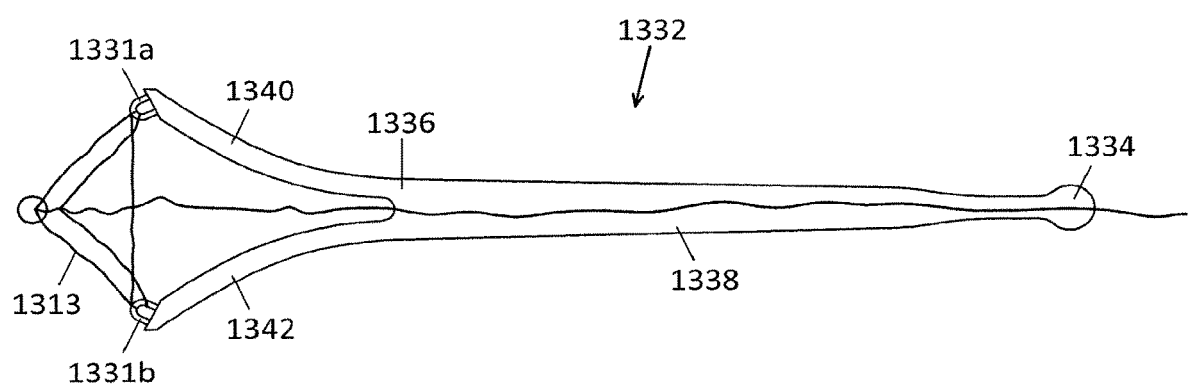
FIG. 13 shows a nasal implant with anchoring features that are deployed by a suture.

An exemplary implant with anchoring features is shown in FIG. 13. The implant 1332 includes a central body 1338, an atraumatic proximal end 1334, and a distal end 1336 with two forked arms 1340, 1342. The implant 1332 further includes a suture 1313 extending from the arms 1340, 1342 (e.g., attached to the arms 1340, 1342 with eyelets 1331a,b). The suture 1313 can be pulled proximally to force the forked arms 1340 into engagement with the tissue. In some embodiments, the implant 1332 can have living hinges that are deployed by pulling on the suture 1313 to aid in anchoring.

Another exemplary implant with anchoring features is shown in FIG. 14. The implant 1432 includes a central body 1438 having a patterned surface 1414 thereon. The patterned surface 1414 includes some open spaces that can allow for tissue ingrowth or engagement with the tissue. Additionally, the patterned surface 1414 can be used to modify the stiffness and mechanical properties of the nasal implant 1432. The outer patterned surface 1414 can be connected to an inner core 1441 of the nasal implant 1432. The inner core 1441 configuration and material can be selected to provide the desired stiffness and flexibility of the implant 1432 along different planes.

Another exemplary implant with anchoring features is shown in FIG. 15. The implant 1532 includes a central body 1538 and a distal end 1536 with two forked arms 1540, 1542, and an atraumatic proximal end (not shown in FIG. 15). The central body 1538 can include a series of undulations 1515 with hollow sections 1551 therein. The undulations 1515 and hollow sections 1551 can extend along the length of the nasal implant 1532. The hollow sections 1551 allow tissue ingrowth along the length of the implant 1538. Further, the undulations 1515 can extend on opposite sides of the implant with flattened or substantially smooth surfaces therebetween. The undulations 1515 can thus provide a higher stiffness in some planes compared to other planes. The nasal implant 1532 can provide improved support of the nasal valve tissue by providing a higher stiffness to support the nasal valve tissue while providing lower stiffness/more flexibility along other planes.

Another exemplary implant with anchoring features is shown in FIG. 16. The implant 1632 includes central body 1638, a distal end 1636 with two forked arms 1640, 1642, and an atraumatic proximal end (not shown). The central body 1638 includes a repeating exterior surface pattern with sections 1665 having a larger cross-section and barbs 1616 projecting therefrom (e.g., on opposing sides of the central body 1638) and sections 1664 having a smaller cross-section than sections 1665 (e.g., creating divots in the surface). The barbs 1616 within sections 1665 can improve tissue engagement and reduce or prevent migration of the nasal implant. Further, sections 1664 can improve the flexibility of the nasal implant due to their smaller cross-section.

Figure 35A:
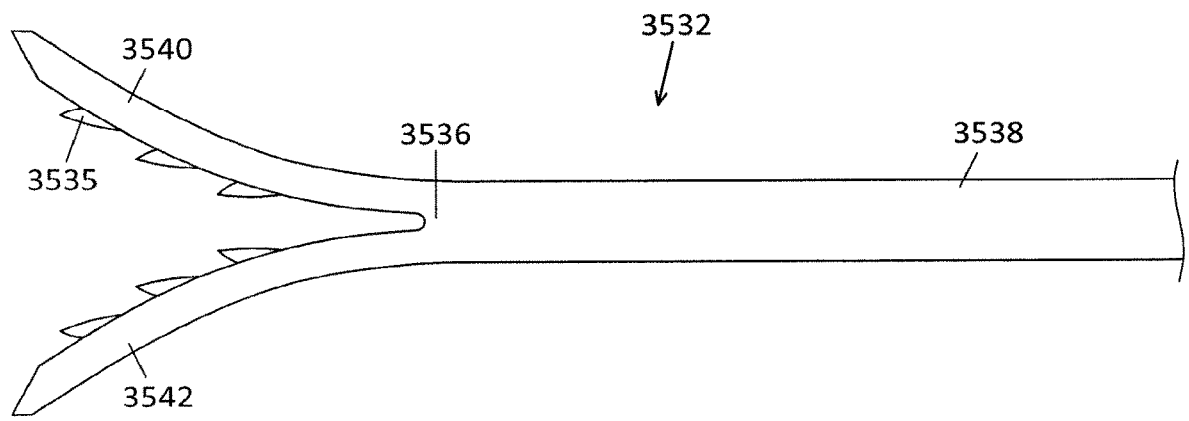
FIGS. 35A-35C show a nasal implant with barbs on the inner portions of the arms of the implant.
Figures 35B, 35C:
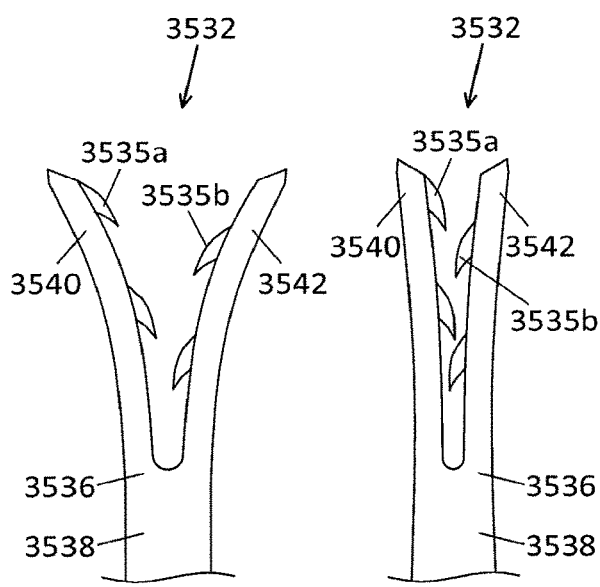

FIGS. 35A-35C illustrates a nasal implant with barbs configured to help with anchoring of the implant. The implant 3532 includes a central body 3538, a distal end 3536 with two forked arms 3540, 3542, and an atraumatic proximal end (not shown). The arms 3540, 3542 can both have barbs 3535a,b thereon. Further, the barbs 3535a,b can extend on the inner portions of the arms 3540, 3542 such that the barbs 3535a on one arm 3540 point towards the barbs 3535b on another arm 3542. The barbs 3535a can be staggered relative to the barbs 3535b such that, upon collapsing of the implant 3532 (e.g., during delivery), as shown in FIGS. 35B and 35C, the barbs 3535a,b do not overlap to allow for a low delivery profile.

Figure 36:
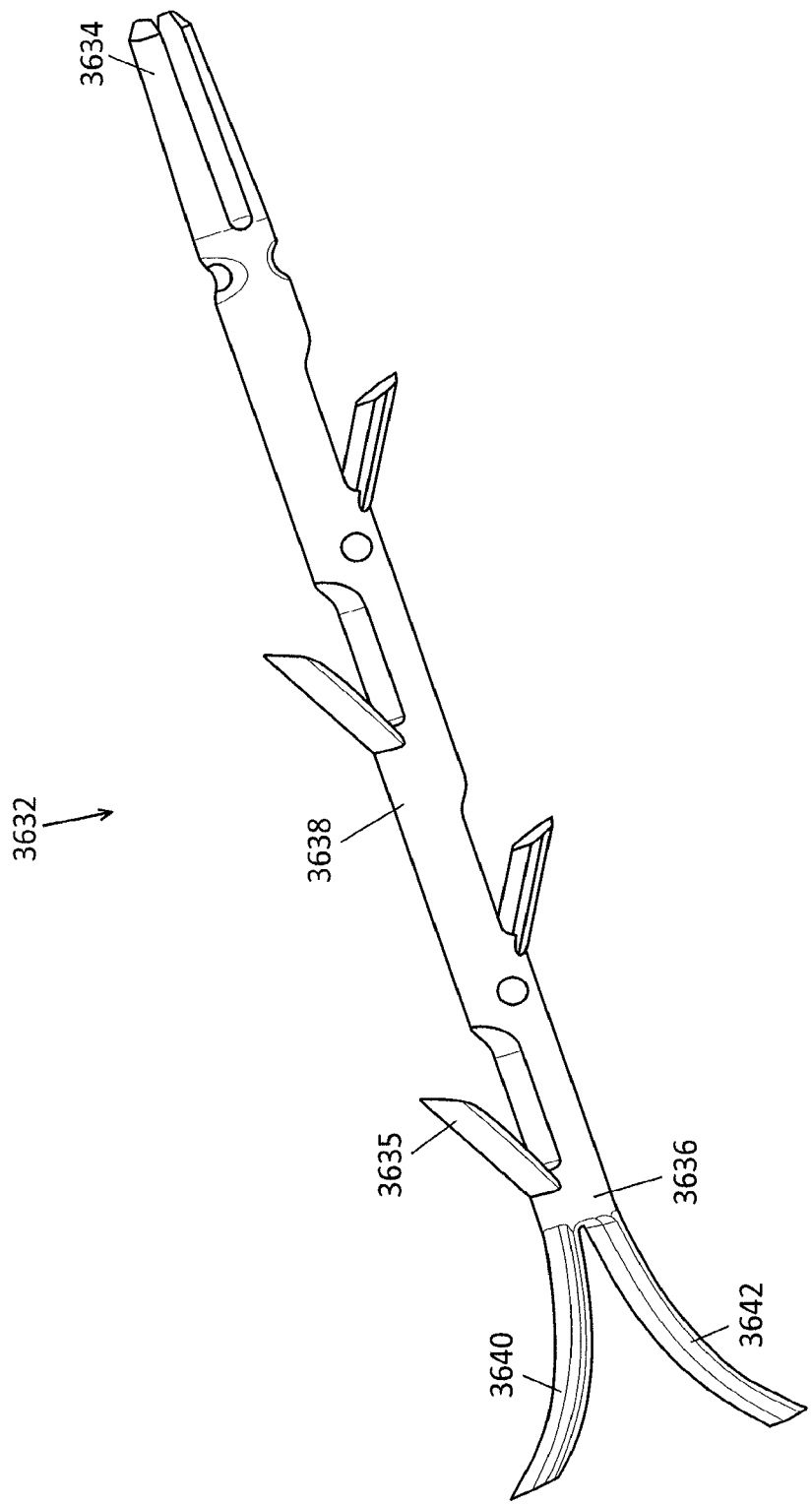
FIG. 36 shows a nasal implant with barbs that are designed to fold out from the central body.

FIG. 36 illustrates another nasal implant with a plurality of barbs for anchoring. The nasal implant 3632 includes a central body 3638, a distal end 3636 with two forked arms 3640, 3642, and an atraumatic proximal end 3634. The central body 3638 includes barbs 3635 thereon that are designed to fold out from the central body 3638 to prevent migration of the nasal implant 3632 after implantation. The foldable barbs 3635 can also promote tissue ingrowth and spread the load for supporting the nasal valve tissue. The barbs 3635 illustrated in FIG. 36 are cut from a portion of the central body 3638 of the nasal implant such that the barbs 3635 have a complementary structure to the corresponding recesses along the body of the central body 3638. Additionally, the atraumatic proximal end 3634 includes two parallel features with atraumatic ends. The space between the features can advantageously allow for tissue ingrowth.

Figure 37:
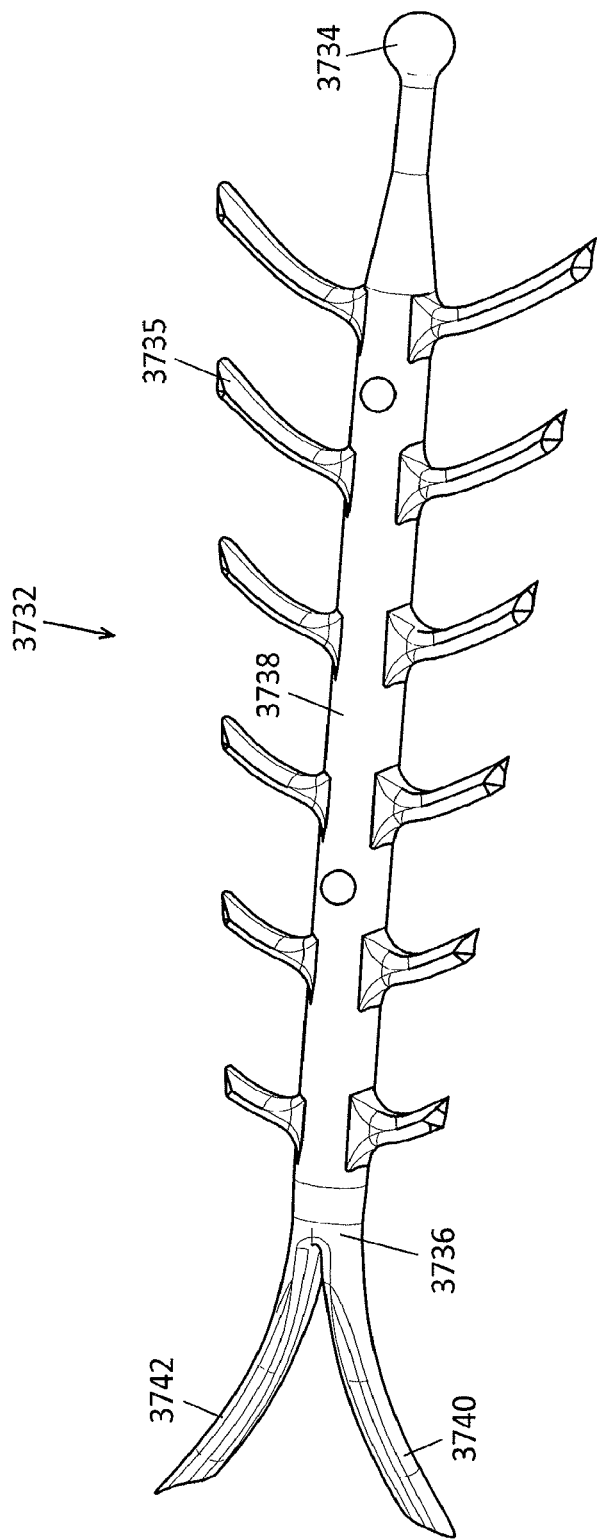
FIG. 37 shows a nasal implant with barbs projecting from opposing sides of the central body.

FIG. 37 illustrates another nasal implant with a plurality of barbs for anchoring. The implant 3732 includes a central body 3738, a distal end 3736 with two forked arms 3740, 3742, and an atraumatic proximal end 3734. The nasal implant 3732 includes a plurality of barbs 3735 projecting from opposing sides of the central body 3738 of the nasal implant. The illustrated barbs 3735 have different sizes along the axis of the central body 3738. The lengths of the barbs 3735 increase with distance from the forked end of the nasal implant. The barbs 3735 can also project at varying angles with respect to the axis of the central body 3738. The barb configuration illustrated in FIG. 37 provides additional surface area to support the tissue along with a larger footprint to spread out the support for the nasal valve. The illustrated configuration also provides additional torsional resistance to twisting of the implant 3732 in the tissue.

Figure 38:
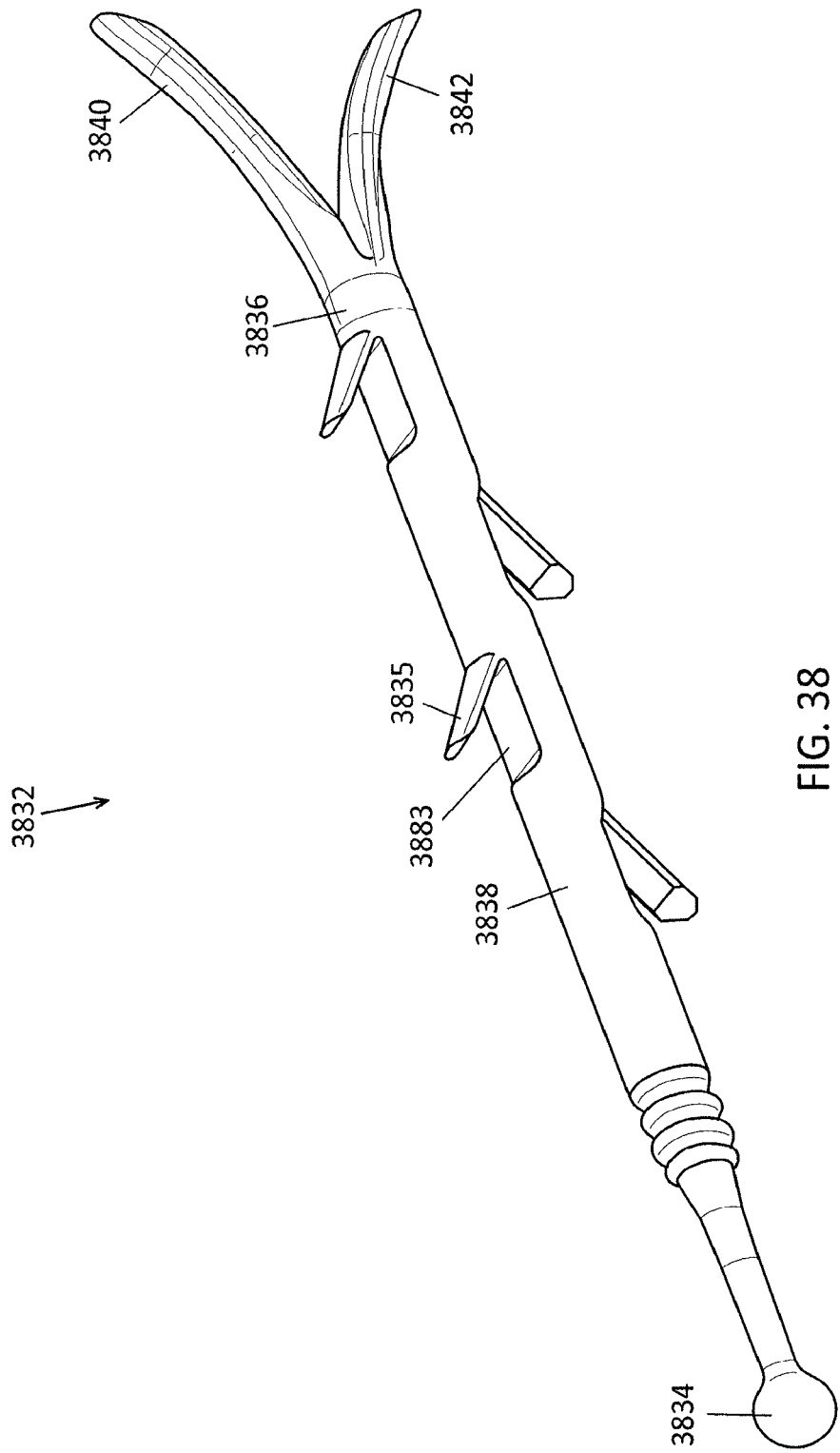
FIG. 38 shows a nasal implant with barbs projecting from opposing sides of the central body.

FIG. 38 illustrated another nasal implant with a plurality of barbs for anchoring. The implant 3832 includes a central body 3838, a distal end 3836 with two forked arms 3840, 3842, and an atraumatic proximal end 3834. The central body 3838 includes a plurality of barbs 3835 along the length thereof. The illustrated configuration has two barbs 3835 projecting from each of two opposing sides of the nasal implant. The barbs 3835 are staggered along the length of the central body 3838. Further, the central body has a plurality of recesses 3883 adjacent to, and having a shape correspond to, each of the barbs 3835 so that the barbs 3835 can have a compressed configuration for when the nasal implant 3832 advances through the cannula for delivery to the targeted tissue.

FIGS. 39A-39D show two more embodiments of implants with barbed anchoring features. Referring to FIGS. 39A-39B, the implant 3932*a* includes a central body 3938*a*, a distal end 3936*a* with two forked arms 3940*a*, 3942*a*, and an atraumatic proximal end 3934*a*. The barbs 3935*a* can be configured as small nubs that extend outwards from each of the arms 3942*a,b*. Referring to FIGS. 39C-39D, the implant 3932*b* includes a central body 3938*b*, a distal end 3936*b* with two forked arms 3940*b*, 3942*b*, and an atraumatic proximal end 3934*b*. The arms 3940*b*, 3942*b* include large barbs 3935*b* extending therefrom. Each barb 3935*b* can include a corresponding recess 3983*b* configured to hold the barb 3935*b* therein when the implant 3932*b* is compressed.

Figure 40A:
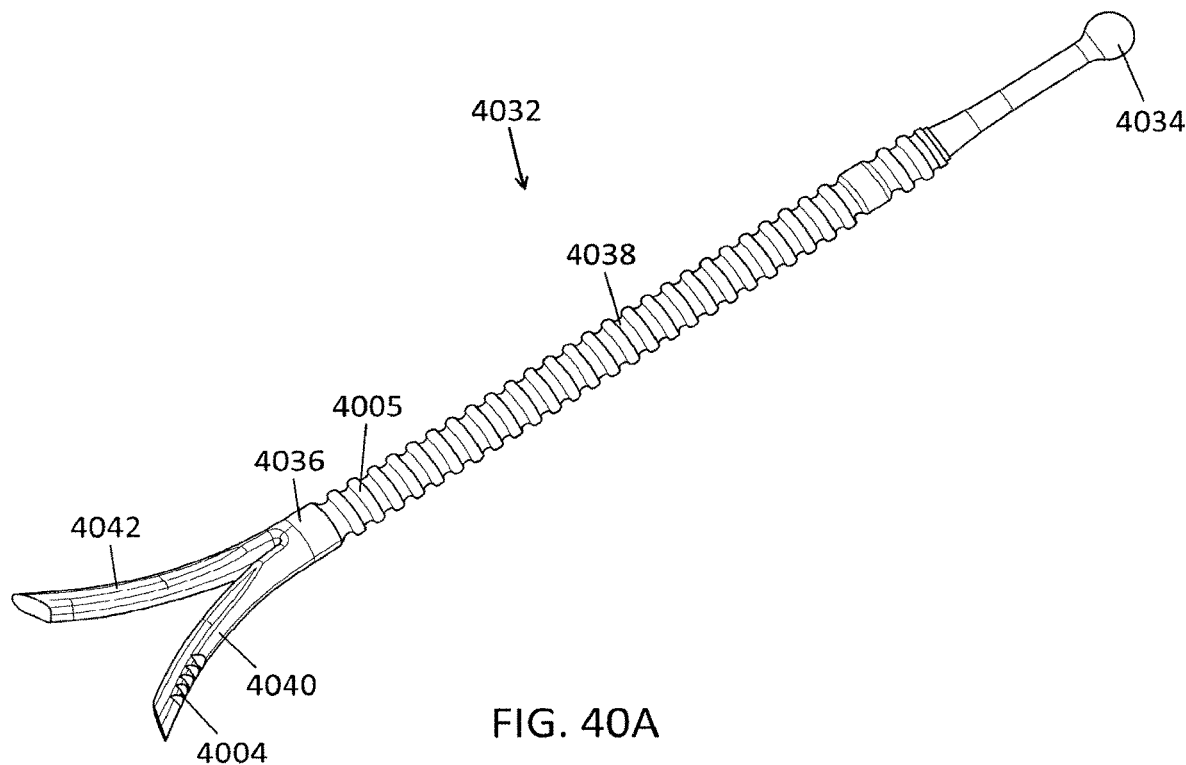
FIGS. 40A-40B show a nasal implant with notches thereon.
Figure 40B:
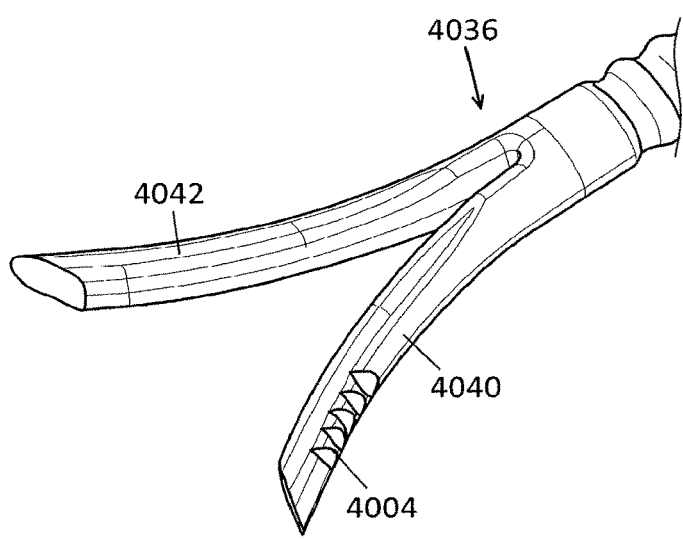

FIGS. 40A-40B illustrate another implant with anchoring features. The implant 4032 includes a central body 4038, a distal end 4036 with two forked arms 4040, 4042, and an atraumatic proximal end 4034. One or both of the arms 4040, 4042 can include small notches 4004 on the outer surface thereof that can act as anchoring features. The notches 4004 can be molded or skived. Further, the central body 4038 can include a series of raised rings 4005 therearound that can act as anchoring features.

Figure 41A:
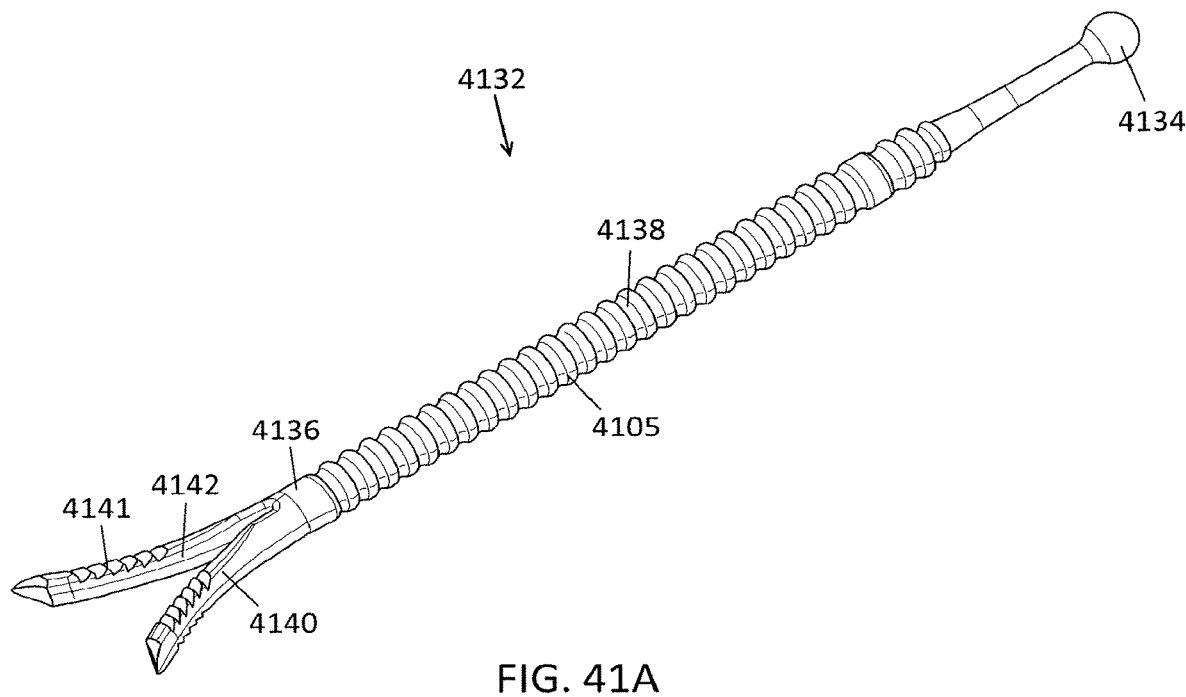
FIGS. 41A-41B show a nasal implant with a plurality of transverse notched projections on the arms.
Figure 41B:
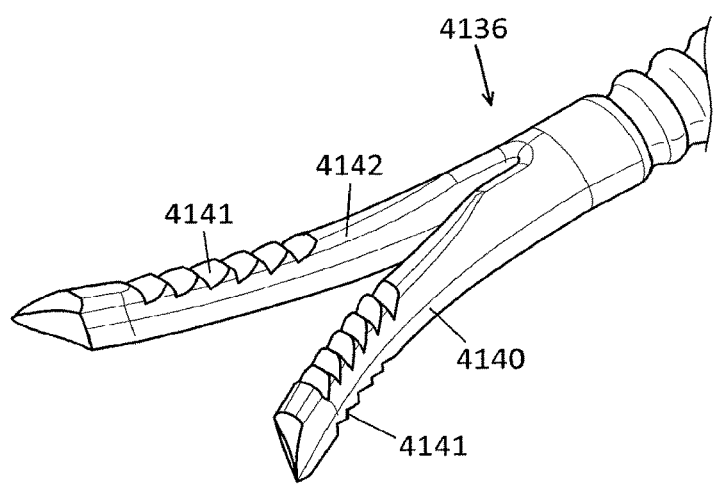

FIGS. 41A-41B illustrate another implant with anchoring features. The implant 4132 includes a central body 4138, a distal end 4136 with two forked arms 4140, 4142, and an atraumatic proximal end 4134. The arms 4142, 4140 can include a plurality of transverse notched projections 4141 thereon, e.g., configured as teeth. The projections 4141 can extend on both the top and bottom surfaces of each of the arms 4142. Further, the transverse projections can be molded or skived. Additionally, the central body 4138 can include a series of raised rings 4105 therearound that can act as anchoring features.

Figure 42A:
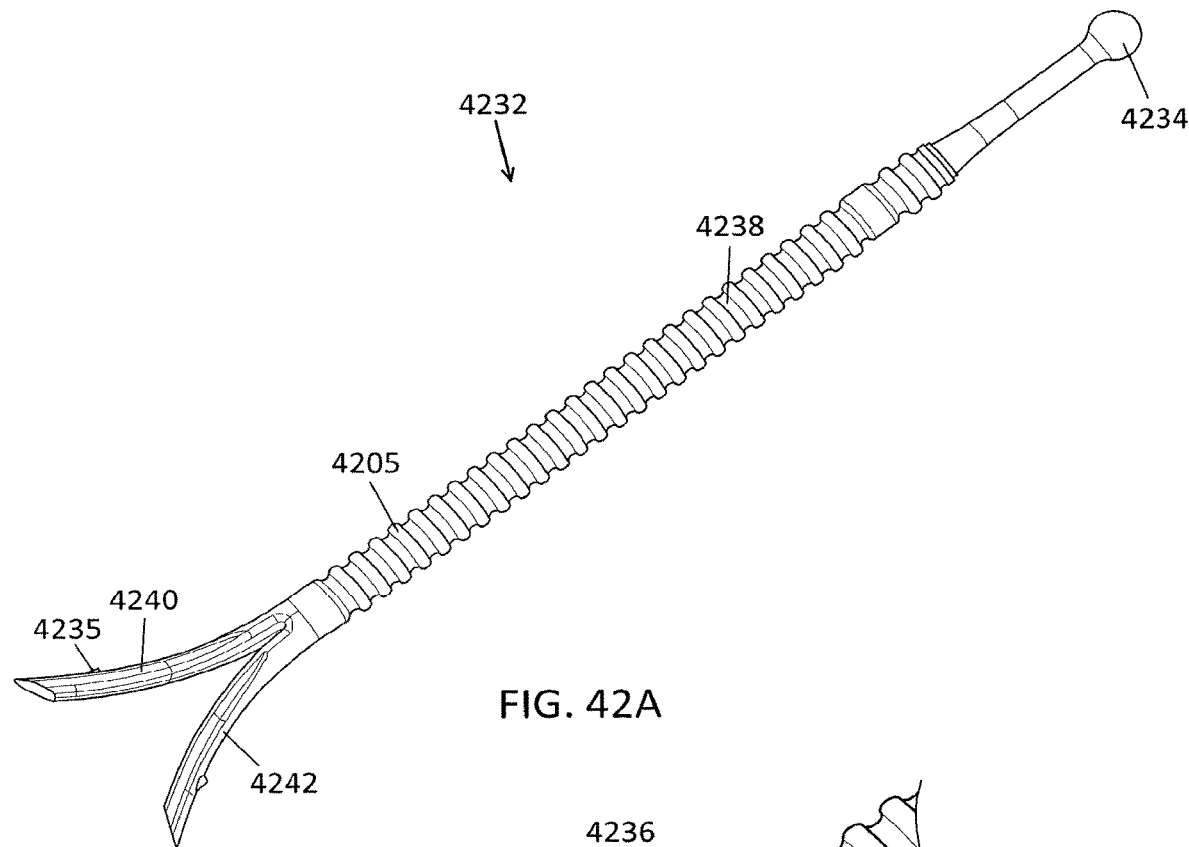
FIGS. 42A-42B show a nasal implant with barbs extending outwards from the arms.
Figure 42B:
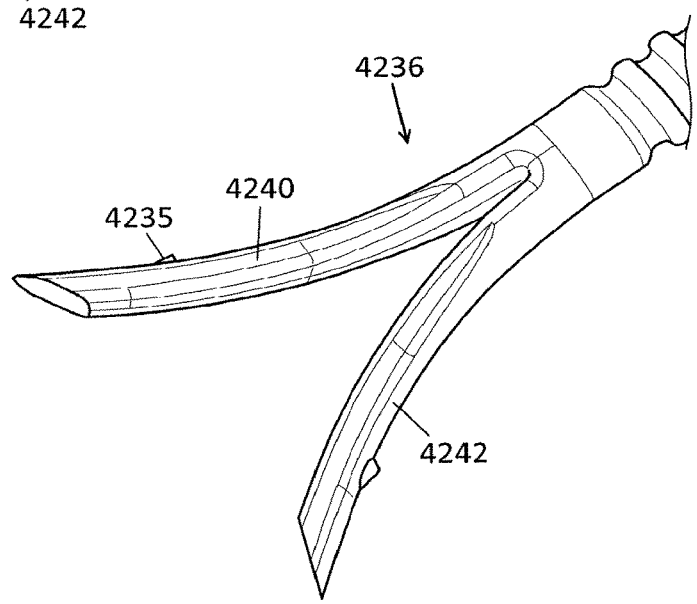

FIGS. 42A-42B illustrate another implant with anchoring features. The implant 4232 includes a central body 4238, a distal end 4236 with two forked arms 4240, 4242, and an atraumatic proximal end 4234. The implant 4232 includes a barb 4235 extending outwards from each of the external surfaces of the arms 4240, 4242. Additionally, the central body 4238 can include a series of raised rings 4205 therearound that can act as anchoring features.

Figure 43A:
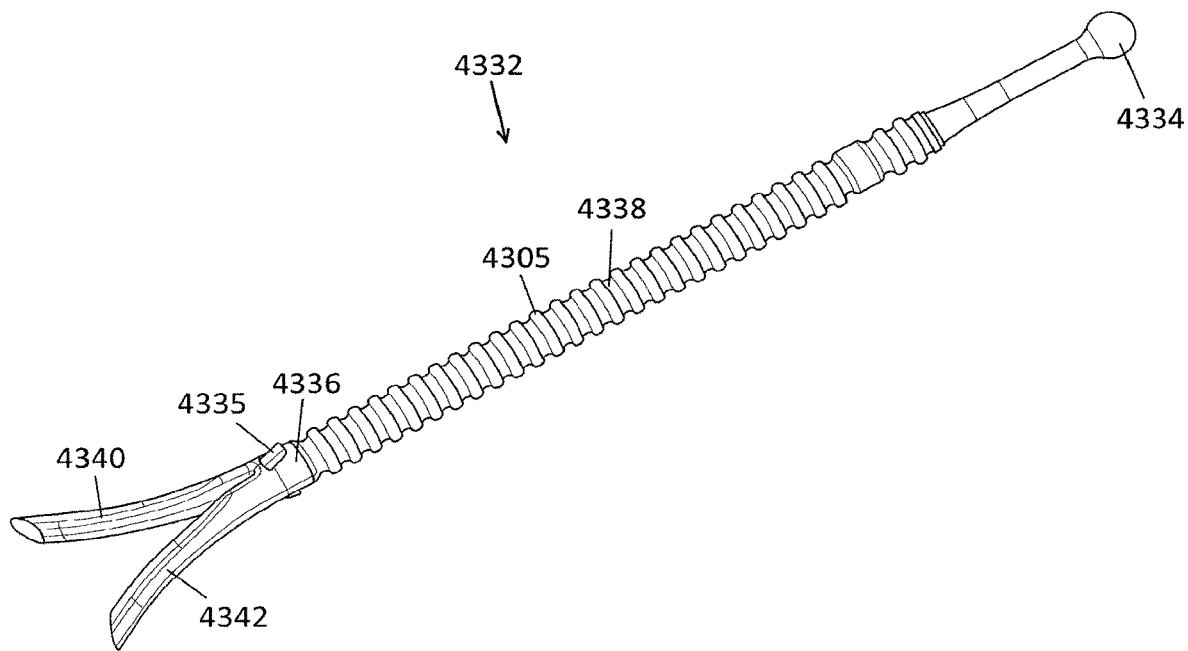
FIGS. 43A-43B show a nasal implant with two barbs at the necked region of the implant.
Figure 43B:
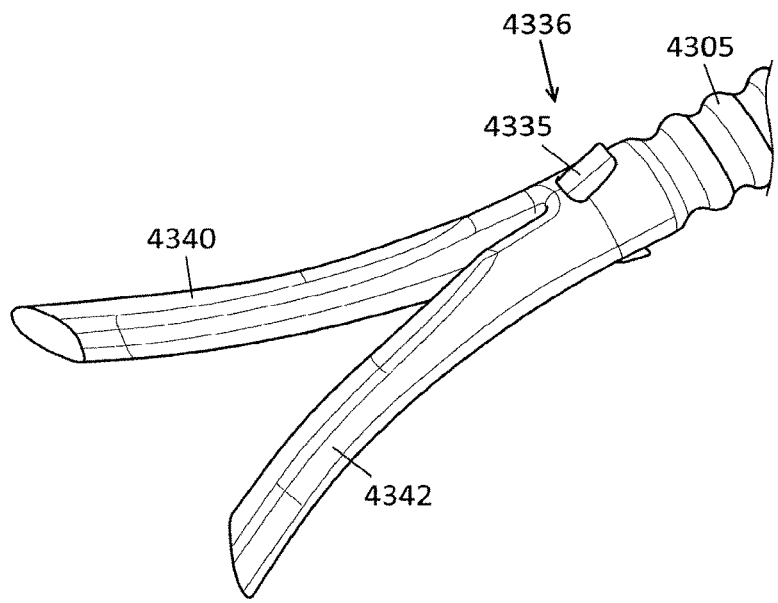

FIGS. 43A-43B illustrate a nasal implant with anchoring features. The implant 4332 includes a central body 4338, a distal end 4336 with two forked arms 4340, 4342, and an atraumatic proximal end 4334. The implant 4332 includes two barbs 4335 at the portion of the implant where the arms 4340, 4342 meet the central body 4338. The barbs 4335 extend transversely to the plane defined by the forked arms 4342, 4340. The barbs 4335 extend from two opposing sides of the implant and can be molded or skived. Additionally, the central body 4338 can include a series of raised rings 4305 therearound that can act as anchoring features.

Figure 44A:
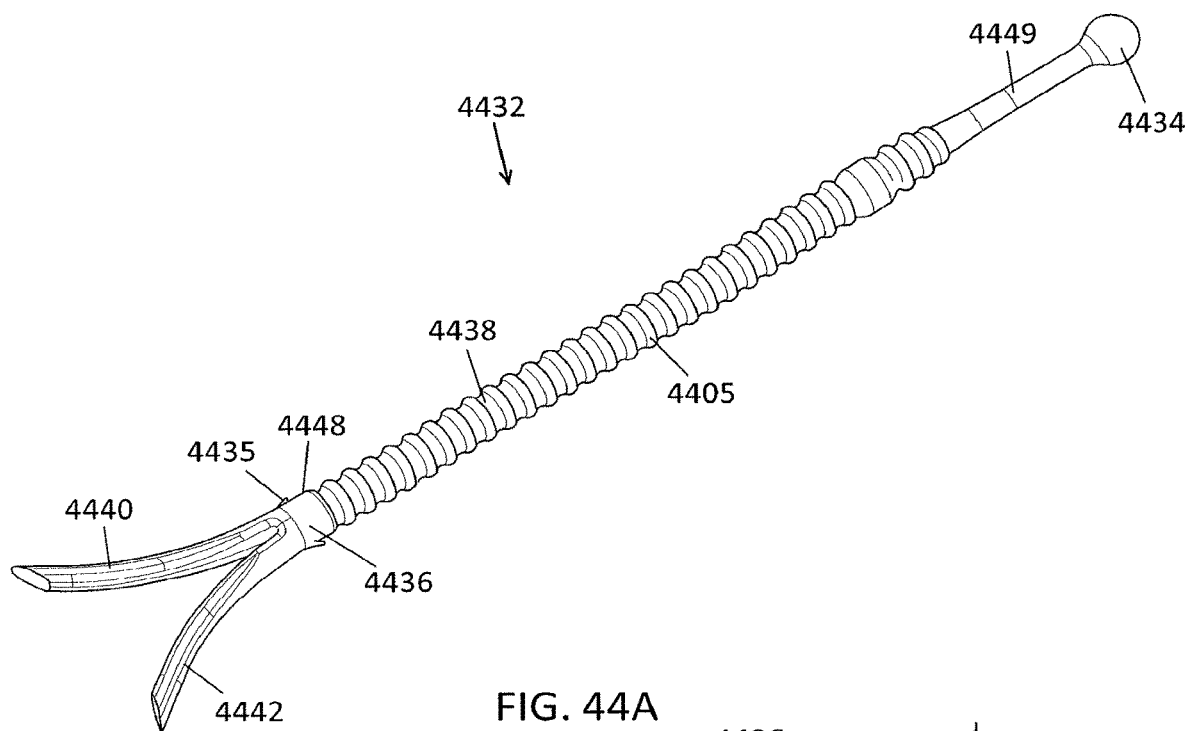
FIGS. 44A-44B show another nasal implant with two barbs at the necked region of the implant.
Figure 44B:
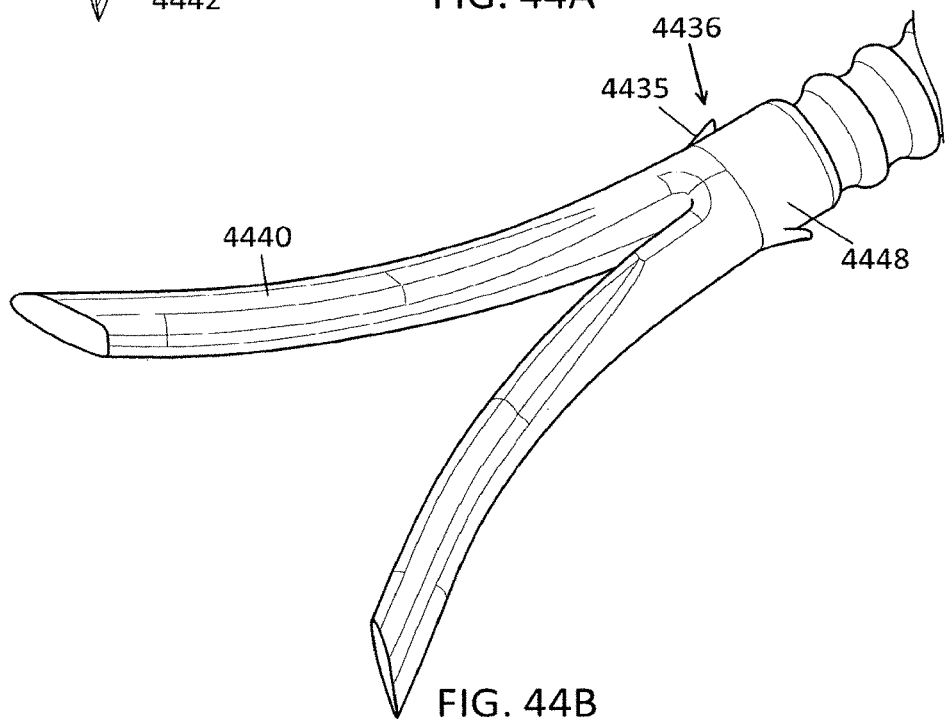

FIGS. 44A-44B illustrate another nasal implant with anchoring features. The implant 4432 includes a central body 4438, a distal end 4436 with two forked arms 4440, 4442, and an atraumatic proximal end 4434. The implant 4432 includes two barbs 4435 at the portion of the implant where the arms 4440, 4442 meet the central body 4438. The barbs 4435 extend in line with a plane defined by the forked arms 4442, 4440. The barbs 4435 extend from two opposing sides of the implant and are molded. Additionally, the central body 4438 can include a series of raised rings 4405 therearound that can act as anchoring features. There can be, for example, 28-32 rings 4405, such as 30-31 rings, such as 30.5 rings. Each ring 4405 can create a valley that is approximately 0.004 inches deep. Further, the central body 4438 with the rings 4405 can be 0.5"-0.6" long, such as 0.55" long. A diameter of the central body 4438 can be approximately 1 mm. Further, the implant 4432 can include a smooth neck 4448 at the distal end 4436 that is, for example, 0.020 to 0.025 inches long, such as approximately 0.24 inches long. Finally, the implant 4432 can include a smooth tail 4449 at the proximal end 4434 that does not include rings 4405 and is approximately 0.18"-0.20", such as 0.19 inches long. The tail can include a bulbous atraumatic end.

Figure 60A:
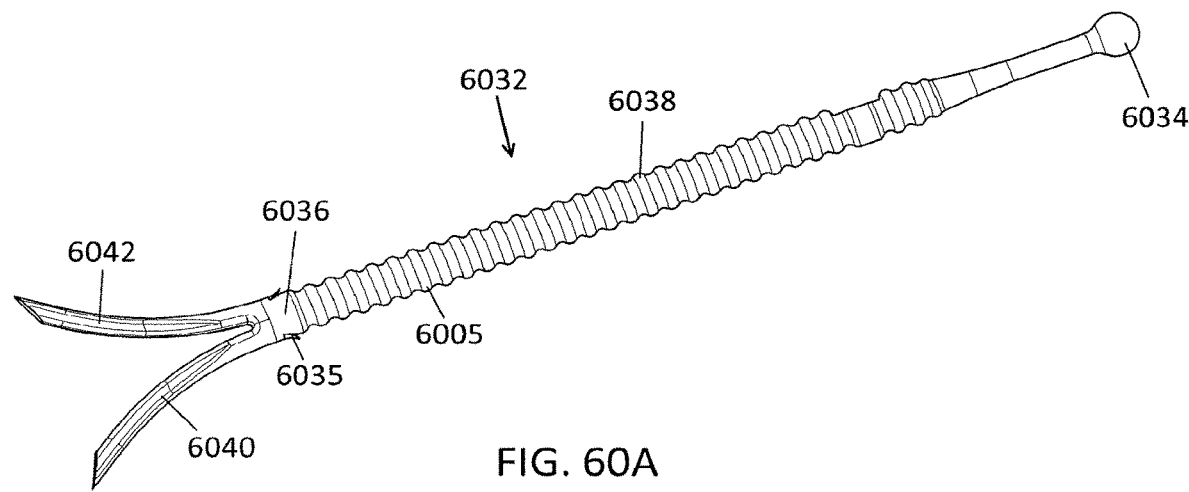
FIGS. 60A-60B show another nasal implant with two barbs at the necked region of the implant.
Figure 60B:
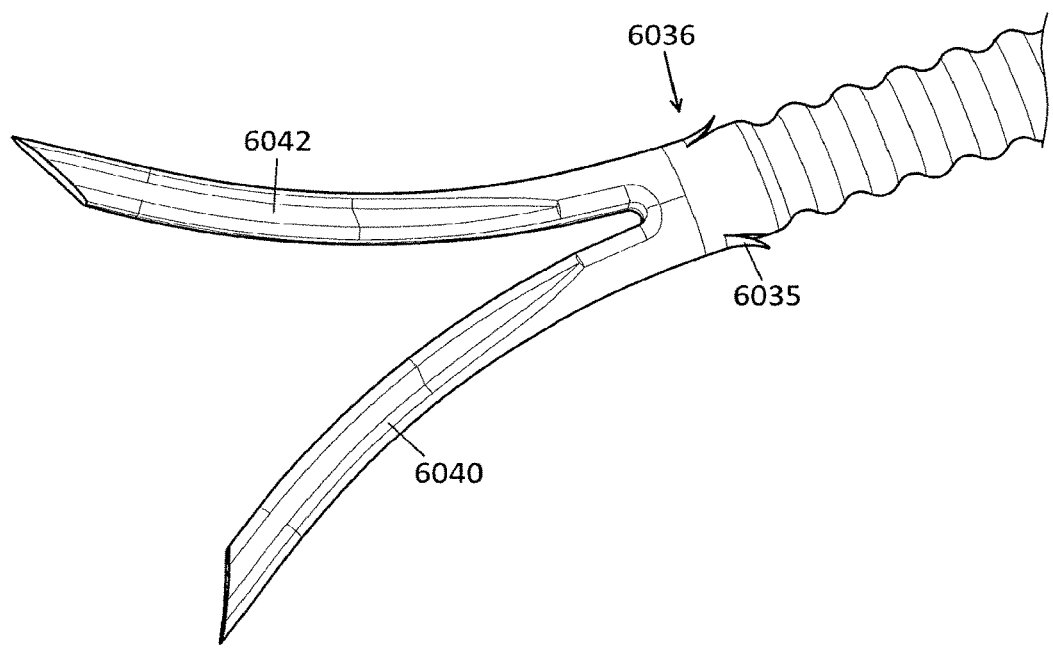

FIGS. 60A-60B illustrate a nasal implant 6032 that is similar to implant 4432 except that the barbs 6035, in contrast to the barbs 4435, are skived. The implant 6032 thus includes a central body 6038, a distal end 6036 with two forked arms 6040, 6042, and an atraumatic proximal end 6034. The implant 6032 includes two barbs 6035 at the portion of the implant where the arms 6040, 6042 meet the central body 6038.

Figure 45A:
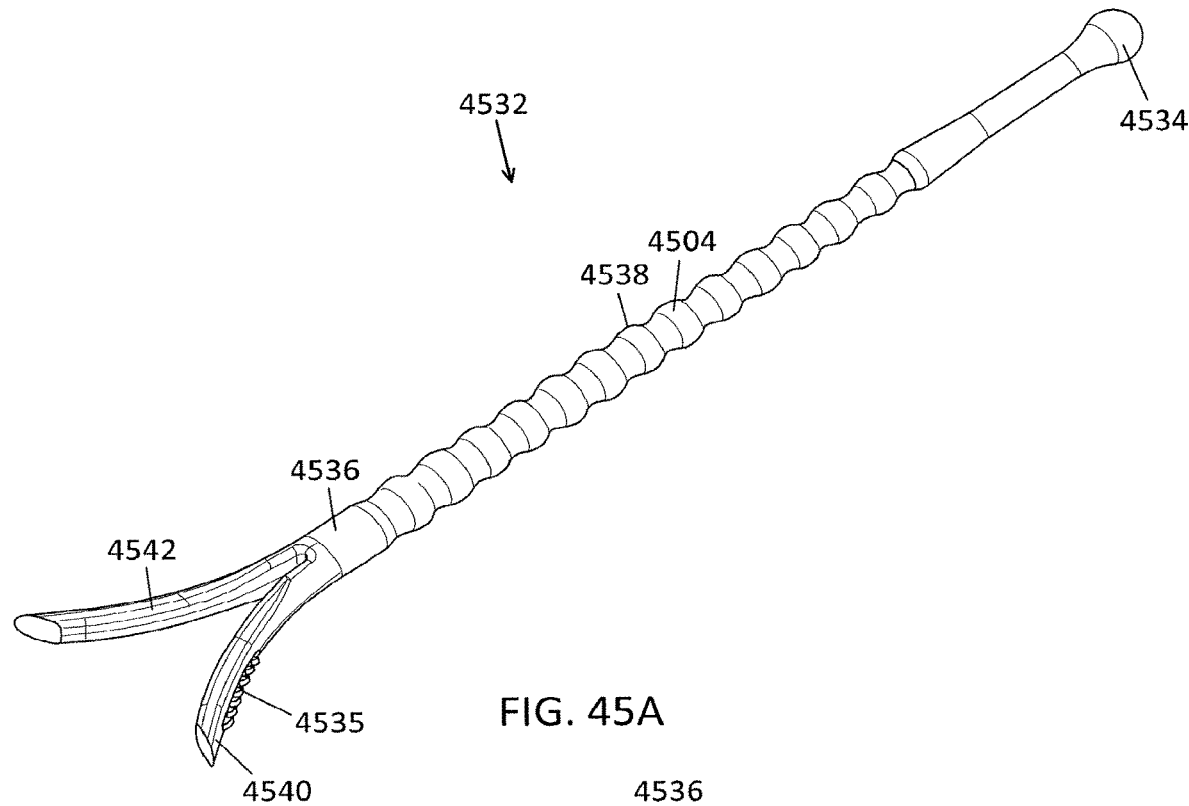
FIGS. 45A-45B show a nasal implant with a plurality of barbs extending outwards from the arms.
Figure 45B:
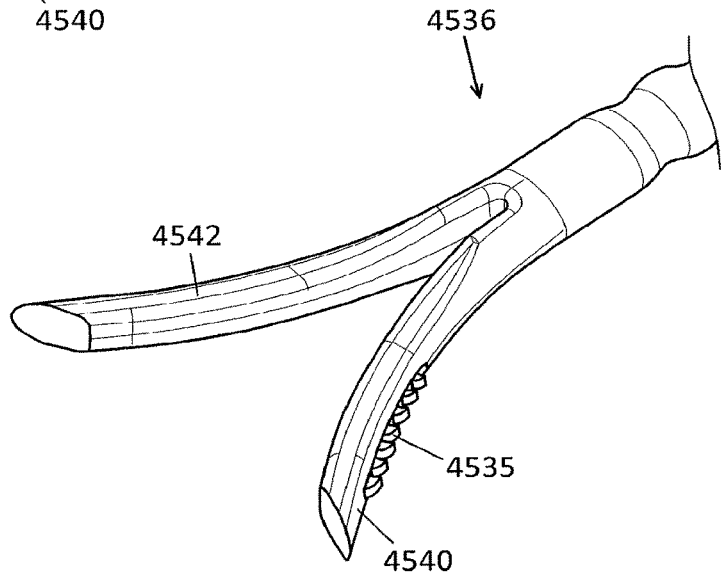

FIGS. 45A-45B illustrate another nasal implant with anchoring features. The implant 4532 includes a central body 4538, a distal end 4536 with two forked arms 4540, 4542, and an atraumatic proximal end 4534. The implant 4532 includes a plurality of barbs 4535 extending on the outer side of each arm 4542, 4540. The barbs 4535 can be projections formed as jagged pointed teeth and can be molded or skived. Additionally, the central body 4538 can include a series of raised rings 4505 therearound that can act as anchoring features.

Figure 46A:
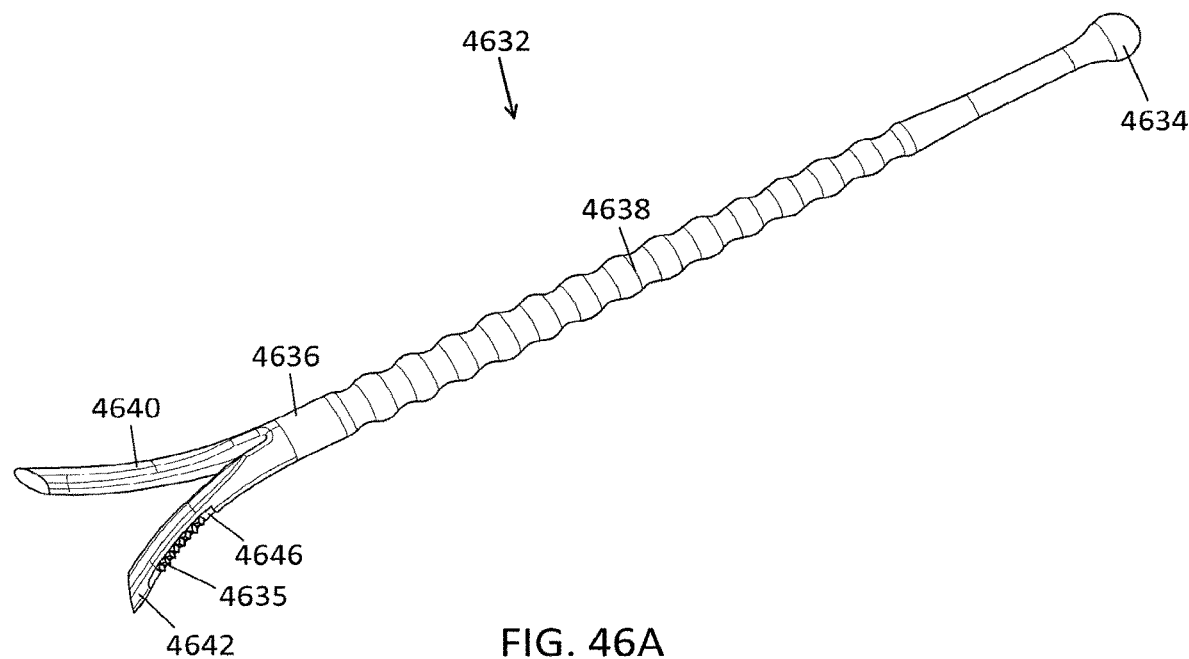
FIGS. 46A-46B show another nasal implant with a plurality of barbs extending outwards from the arms.
Figure 46B:
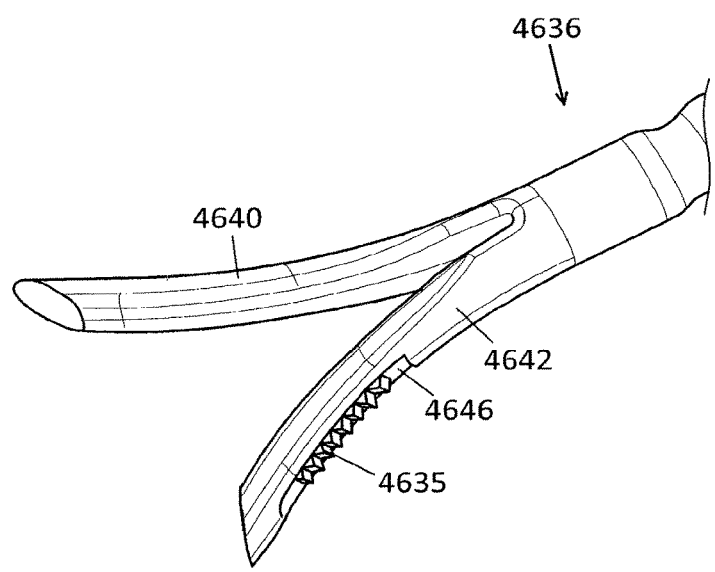

FIGS. 46A-46B illustrate a nasal implant that is similar to implant 4532. The implant 4632 thus includes a central body 4638, a distal end 4636 with two forked arms 4640, 4642, an atraumatic proximal end 4634, and a plurality of barbs 4635 configured similarly to the barbs in implant 4532 except that the barbs sit in a grooved window 4646 or opening in the outer surface to both improve the compactness of the implant when compressed and to help improve tissue ingrowth.

Figure 47A:
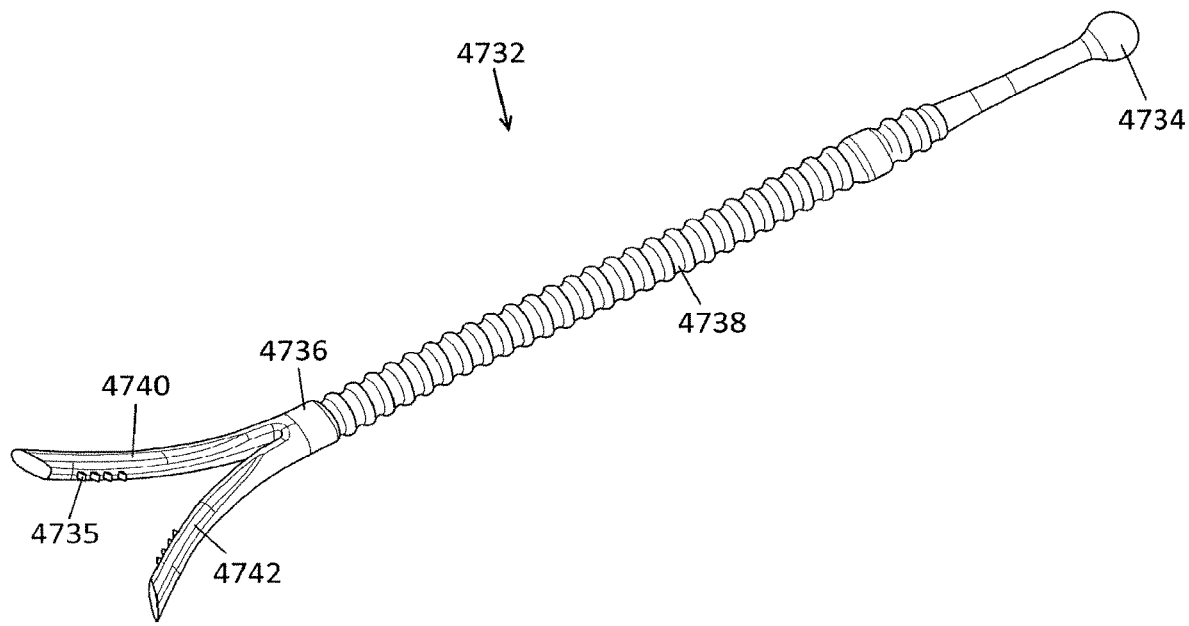
Figure 47B:
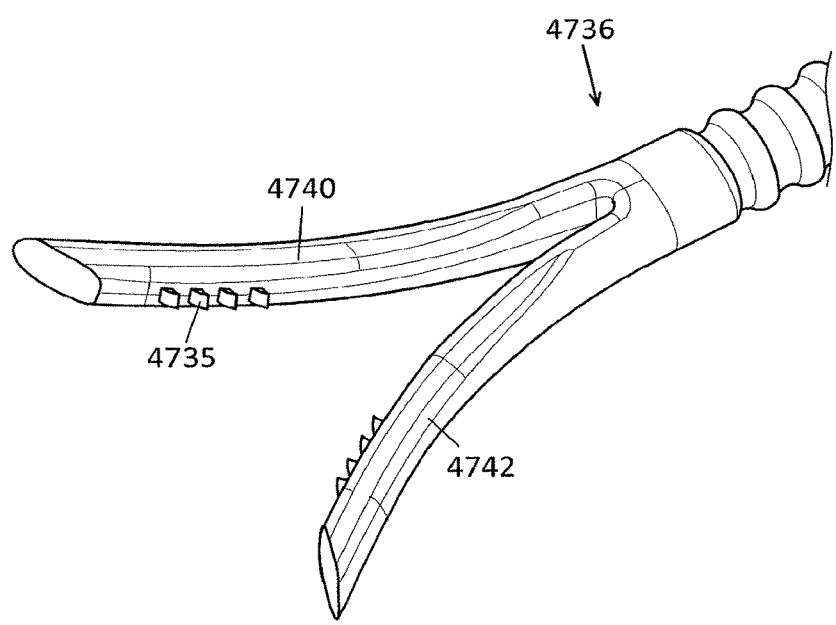

FIGS. 47A-47B illustrate another implant with anchoring features. The implant 4732 includes a central body 4738, a distal end 4736 with two forked arms 4740, 4742, and an atraumatic proximal end 4734. The implant 4732 includes a plurality of smaller barbs 4735 extending from an inside surface of each of the arms 4740, 4742. The smaller notch type barbs 4735 extend from each of the arms 4740, 4742 towards the opposite arm. The smaller barbs 4735 are illustrated as jagged shark teeth type projections. The barbs 4735 can be molded or skived.

Figure 48A:
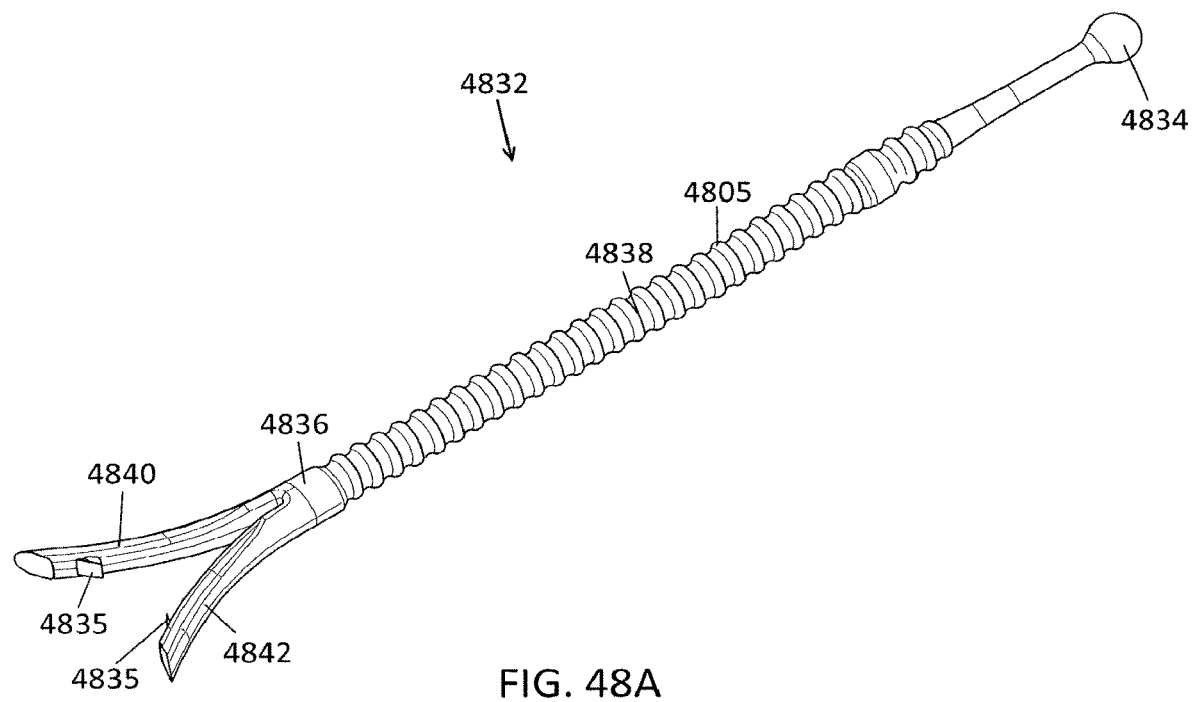
Figure 48B:
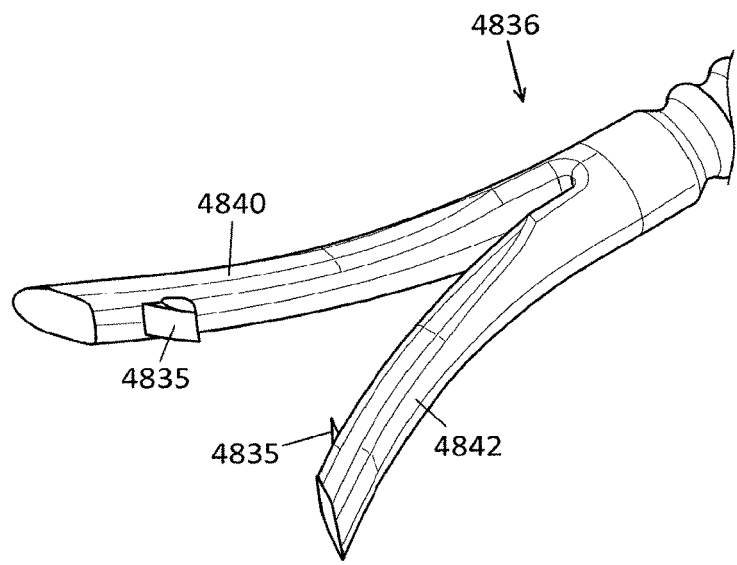

FIGS. 48A-48B illustrate another implant with anchoring features. The implant 4832 includes a central body 4838, a distal end 4836 with two forked arms 4840, 4842, and an atraumatic proximal end 4834. The implant 4832 includes a smaller barb 4835 extending from an inside surface of each of the arms 4840, 4842 towards the opposite arm 4840, 4842. The barbs 4835 are skived. Additionally, the central body 4838 can include a series of raised rings 4805 therearound that can act as anchoring features.

Figure 49A:
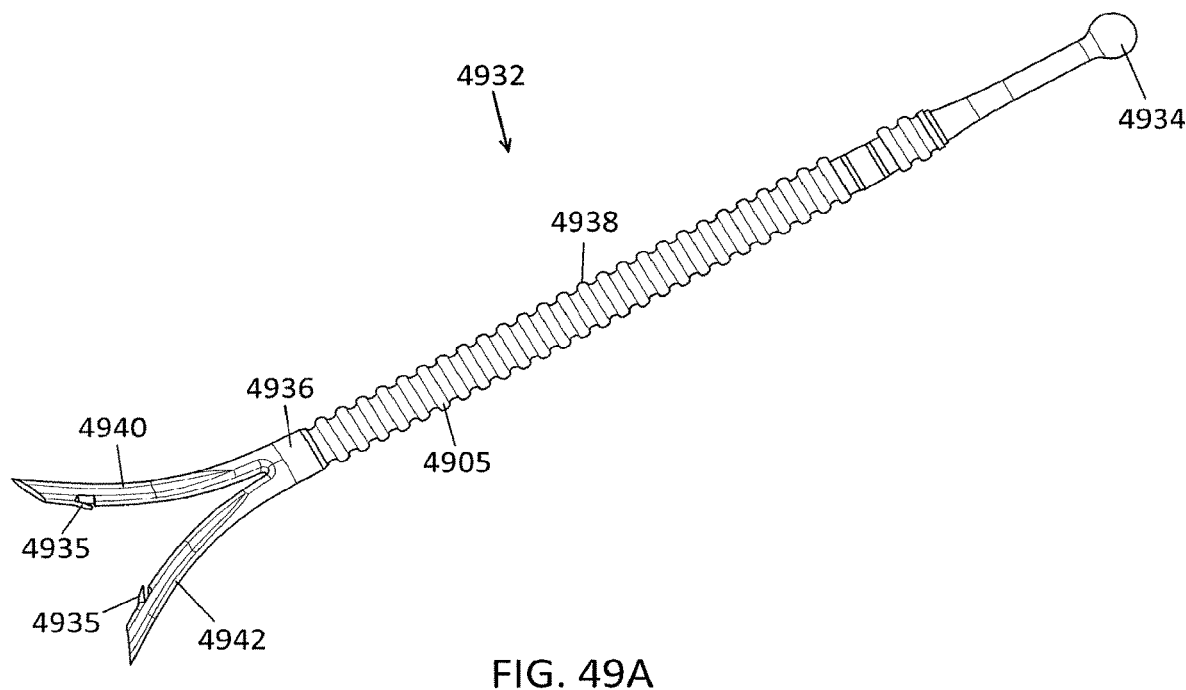
FIGS. 49A-49B show another nasal implant with a plurality of small barbs extending from the inside surface of each of the arms.
Figure 49B:
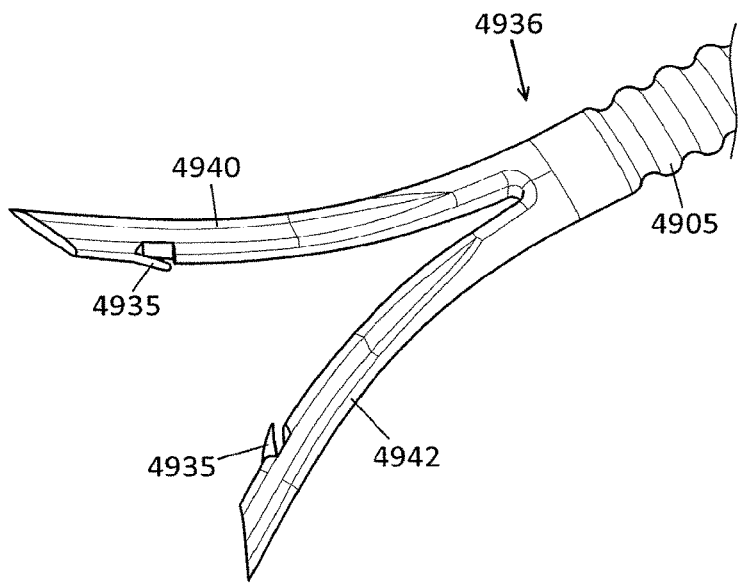

FIGS. 49A-49B illustrate another implant with anchoring features. The implant 4932 includes a central body 4938, a distal end 4936 with two forked arms 4940, 4942, and an atraumatic proximal end 4934. The implant 4932 includes smaller barbs 4935 extending from an inside surface of each of the arms 4940, 4942. The smaller barbs 4935 extend from each of the arms 4942, 4940 towards the other arm. The illustrated barbs 4935 are molded with the body of the implant and then undercut. Additionally, the central body 4938 can include a series of raised rings 4905 therearound that can act as anchoring features.

Figure 50A:
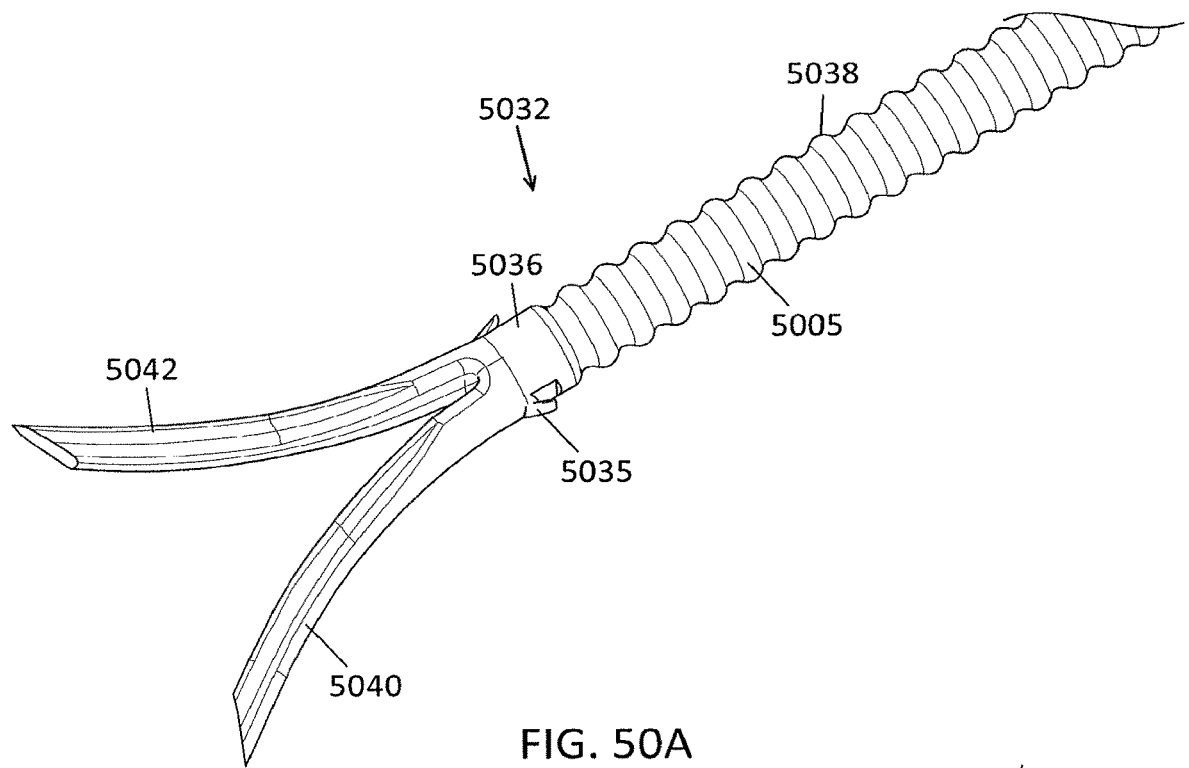
FIGS. 50A-50B show another nasal implant with two barbs at the necked region of the implant.
Figure 50B:
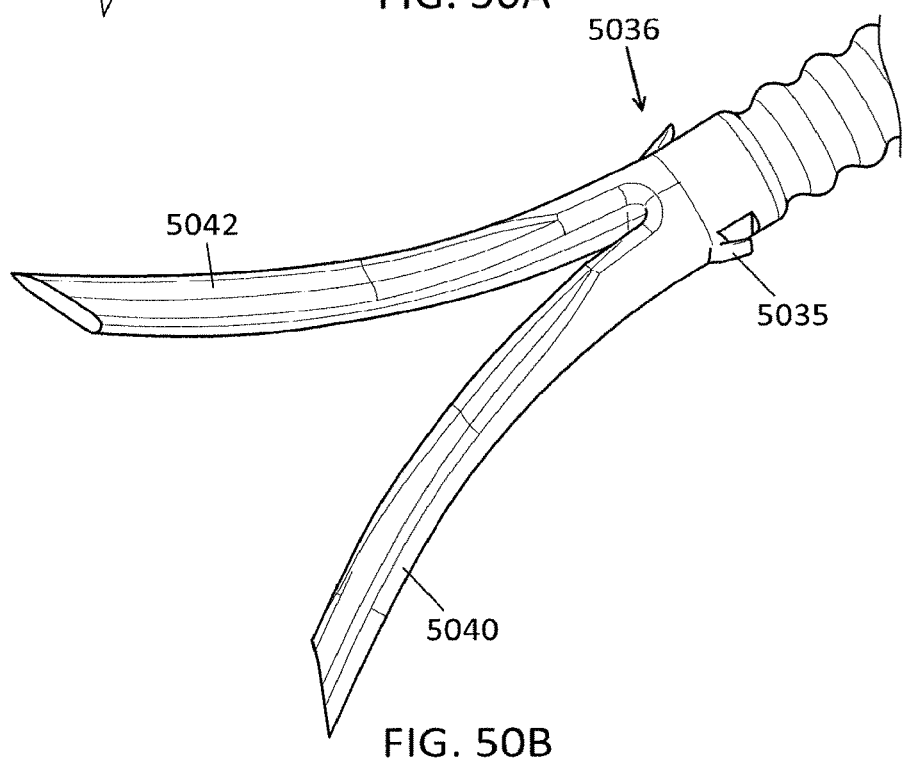

FIGS. 50A-50B illustrate another implant with anchoring features. The implant 5032 includes a central body 5038, a distal end 5036 with two forked arms 5040, 5042, and an atraumatic proximal end (not shown). The implant 5032 includes two barbs 5035 at the portion of the implant where the forked end meets the central body of the implant. The barbs 5035 extend in line with the plane defined by the arms 5042, 5040 of the implant. The barbs 5035 extend from two opposing sides of the implant 5032. The illustrated barbs 5035 are molded with the body of the implant 5032 and then undercut. Additionally, the central body 5038 can include a series of raised rings 5005 therearound that can act as anchoring features.

Figure 51A:
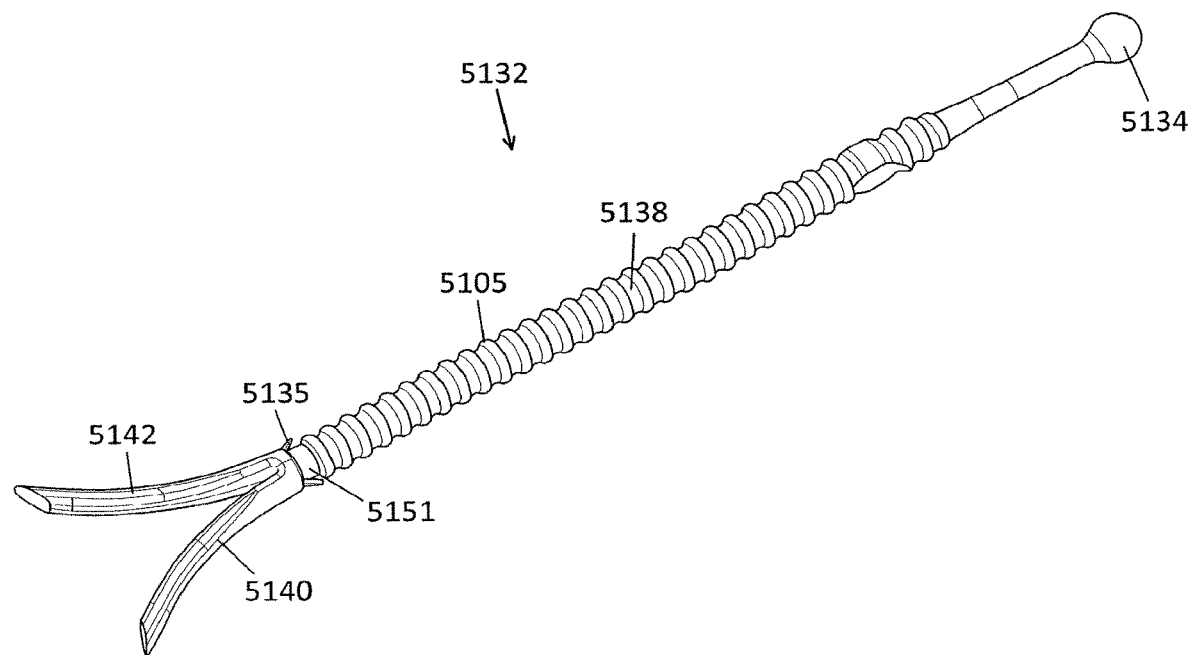
FIGS. 51A-51B show another nasal implant with two barbs at the necked region of the implant.
Figure 51B:
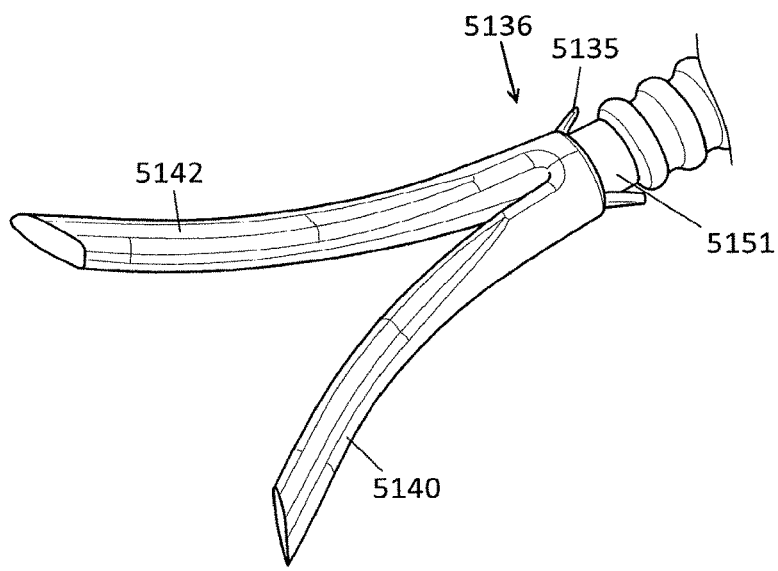

FIGS. 51A-51B illustrate another implant with anchoring features. The implant 5132 includes a central body 5138, a distal end 5136 with two forked arms 5140, 5142, and an atraumatic proximal end 5134. The implant 5132 includes two barbs 5135 at the portion of the implant where the forked arms 5142, 5140 meet the central body 5138 of the implant. The barbs 5135 extend in line with the plane defined by the arms 5142, 5140 of the implant. The barbs 5135 extend from two opposing sides of the implant 5132. Further, in contrast to implant 5032, implant 5132 has a narrow or tapered section 5151 between the central portion 5138 and the distal end 5136 over which the barbs 5135 extend. In one example, the barbs 5135 can be molded inside of undercuts. Additionally, the central body 5138 can include a series of raised rings 5105 therearound that can act as anchoring features.

Figure 52A:
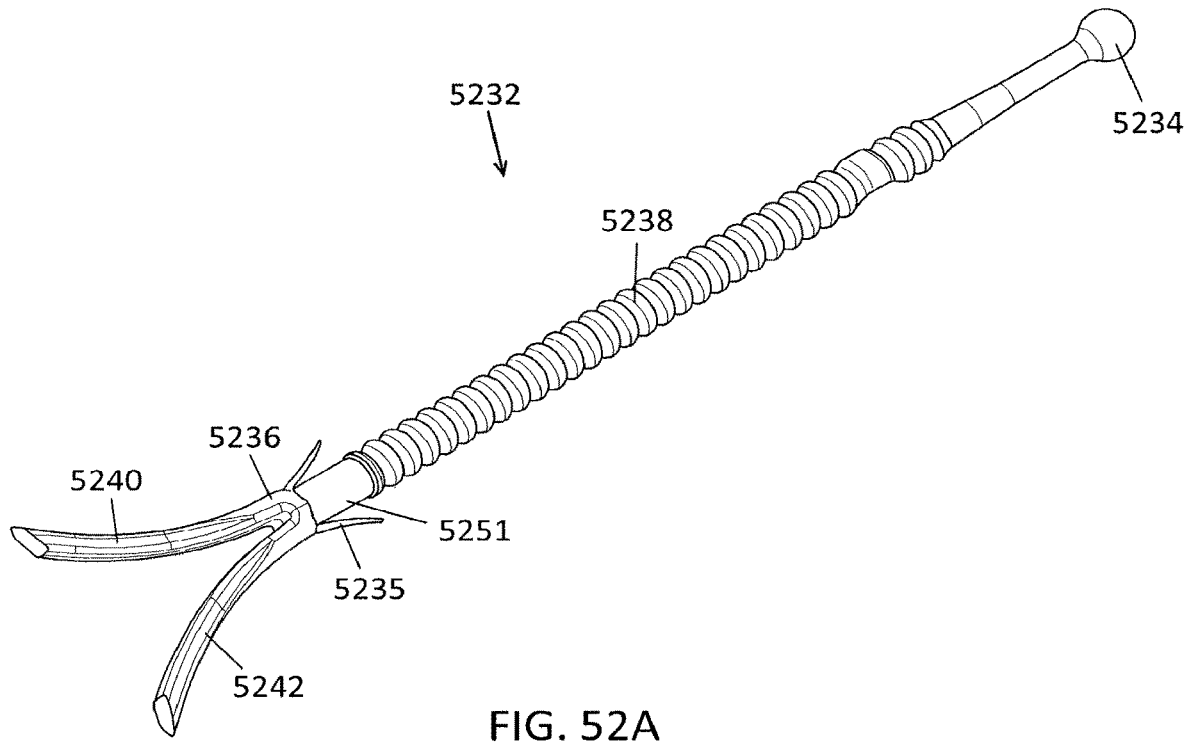
FIGS. 52A-52B show another nasal implant with two barbs at the necked region of the implant.
Figure 52B:
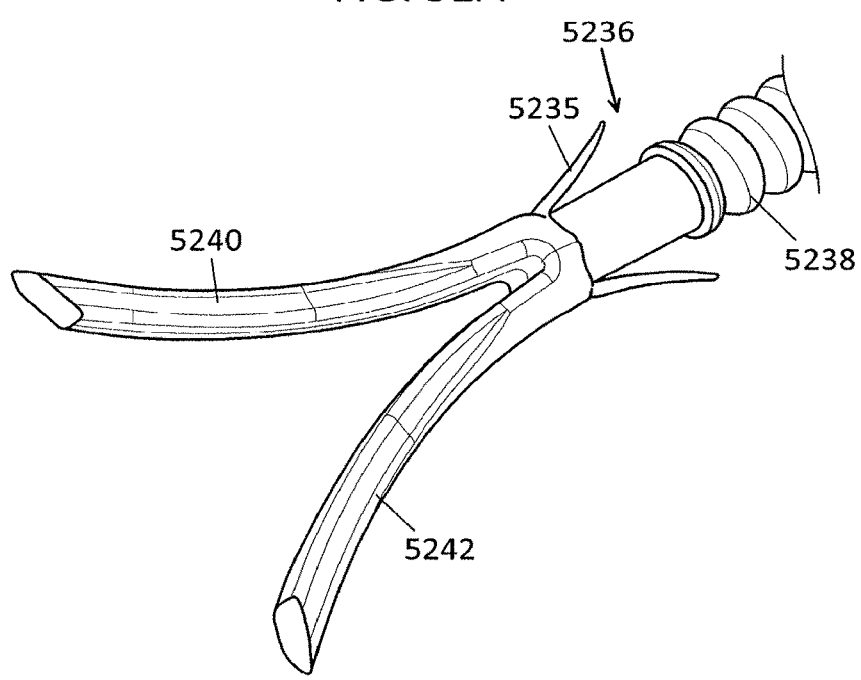

FIGS. 52A-52B illustrate another implant with anchoring features. The implant 5232 includes a central body 5238, a distal end 5236 with two forked arms 5240, 5242, and an atraumatic proximal end 5234. The implant 5232 includes two barbs 5235 at the portion of the implant where the forked arms 5242, 5240 meet the central body 5238 (and extend over narrow section 5240). The barbs 5235 are longer and thinner than the barbs of implant 5132. The barbs 5235 extend in line with the plane defined by the arms 5240, 5242 and extend from two opposing sides of the implant 5232. The neck barbs 5235 can be molded inside of undercuts. Additionally, the central body 5238 can include undulations that can help to anchor the implant in the tissue.

FIGS. 59A-59B illustrate an embodiment of a nasal implant with one or more barbs or barb features. The implant 5932 includes a central body 5938, a distal end 5936 with two forked arms 5940, 5942, and an atraumatic proximal end 5934. The implant 5932 further includes barbs 5935 between the distal tip of the distal end 5936 and the central portion 5938. Different barb geometries can be used, such as varying the thickness of the barb at its base, the length of the barb, how far the barb is offset from the implant surface and the thickness of the barb itself. Additionally, the barbs 5935 can be in any orientation plane positioned about the entire 360 degrees circumference of implant 5392. The dimensions and geometries of the barb can be designed to achieve a desired or pre-selected anchoring performance of the implant.

Figure 61A:
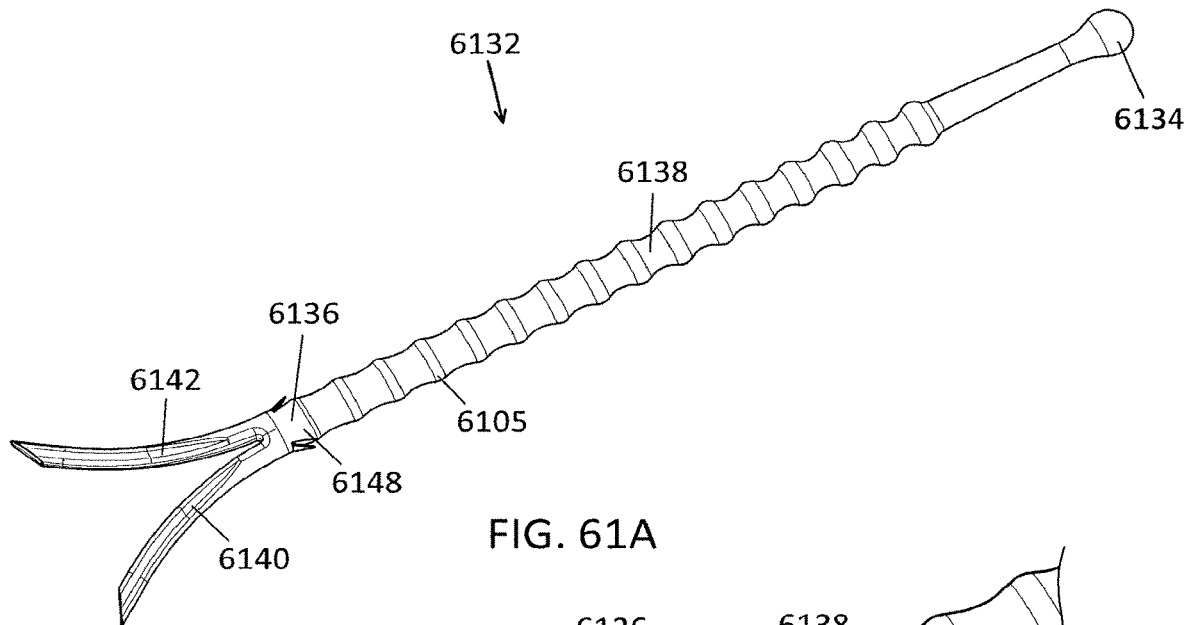
FIGS. 61A-61C show another nasal implant with two barbs at the necked region of the implant.
Figure 61B:
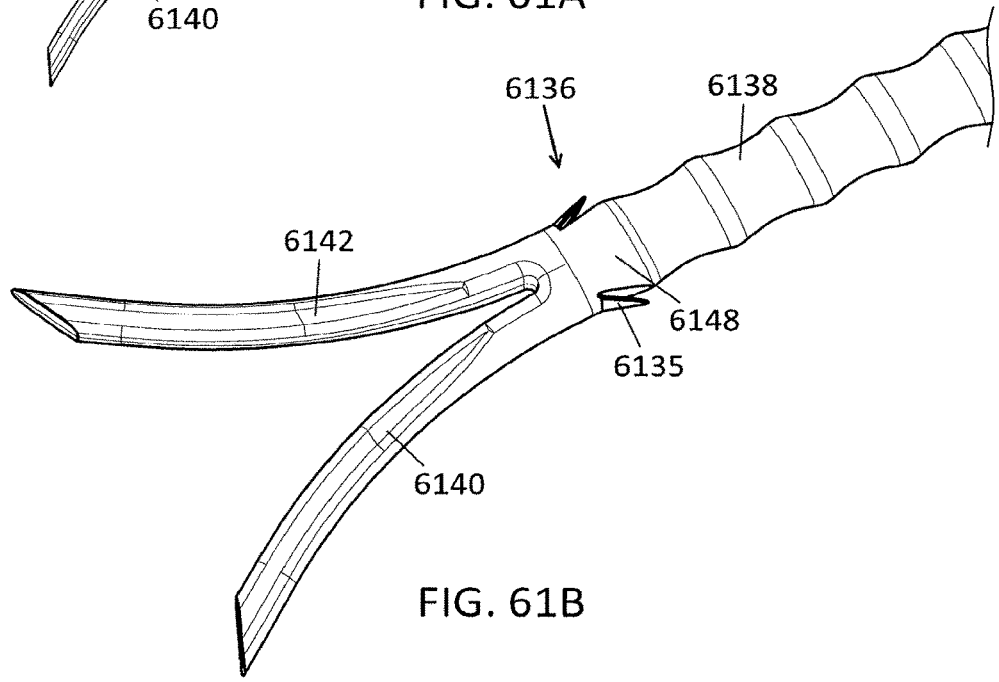
Figure 61C:
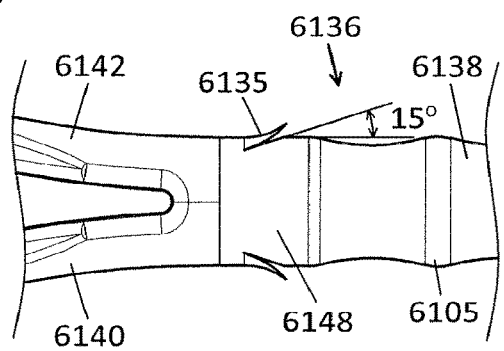

FIGS. 61A-61B illustrate a nasal implant 6132 with barbs 6135 at the portion of the implant where the forked arms 6142, 6140 meet the central body 6138. The barbs 6135 extend in line with the plane defined by the 6140, 6142. The barbs 6135 extend from two opposing sides of the implant. The barbs 6135 illustrated in FIG. 61 are molded with an undercut. As shown in FIG. 61C, the barbs 6135 can be angled at greater than 10 degrees, such as greater than 15 degrees relative to the neck of the distal end 6136. In other embodiments, the barbs are positioned relative to the neck of the distal end (e.g., at an angle of 10-20 degrees relative to the neck or at an angle of more than 20 degrees relative to the neck). Additionally, the central body 6138 can include a series of raised rings 6105 therearound that can act as anchoring features. There can be, for example, 12-18 rings 6105, such as 15 rings 6105. Further, the valley between the rings 6105 can increase in depth from the distal end 6136 to the proximal end 6134 (e.g., from approximately 0.0027" to approximately 0.004"). The core of the central portion 6138 can thus be tapered from the distal end 6136 to the proximal end 6134 (e.g., at a 5 degree taper). A diameter of the central body 6138 at the rings 6105 can be approximately 1 mm, and a length of the central body 6138 can be 0.5"-0.6", such as approximately 0.55". Further, the implant 6132 can include a smooth neck 6148 at the distal end 6136 that is approximately 0.02"-0.03" long, such as 0.025" long. The implant 6132 can include a smooth tail 6149 at the proximal end 6134 that does not include rings 6105 and is approximately 0.15"-0.19", such as 0.18" long. The tail can include a bulbous atraumatic end. The design of the implant 6132 can advantageously be optimized to reduce the maximum stress on the implant upon implantation.

Figure 62:
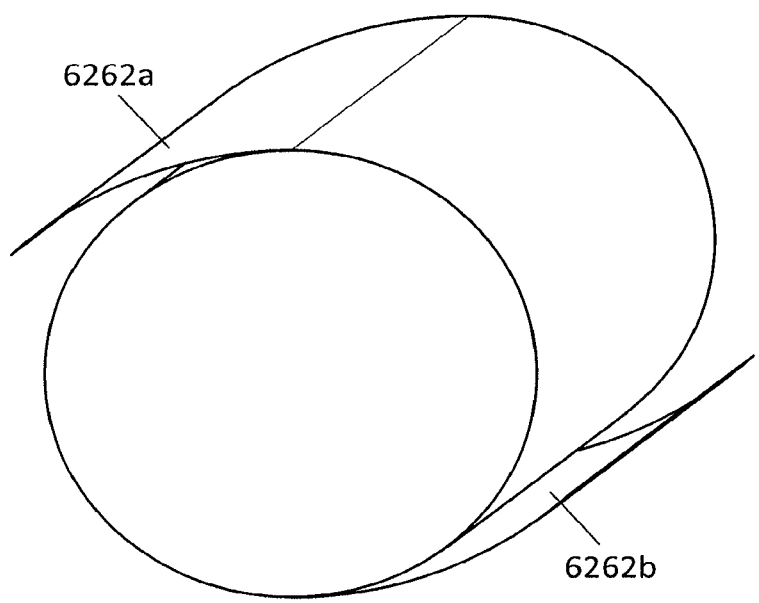
FIG. 62 shows compressed wings that can be used with a nasal implant.

FIG. 62 illustrates an example showing an axial cross-sectional view that includes compressed wings 6262*a,b* having a sheet-like configuration that can be used as part of the implants described herein as anchoring features, e.g., to engage with tissue to prevent migration. The wings 6262*a,b* can also increase stiffness in certain planes of the implant.

Figure 20A:
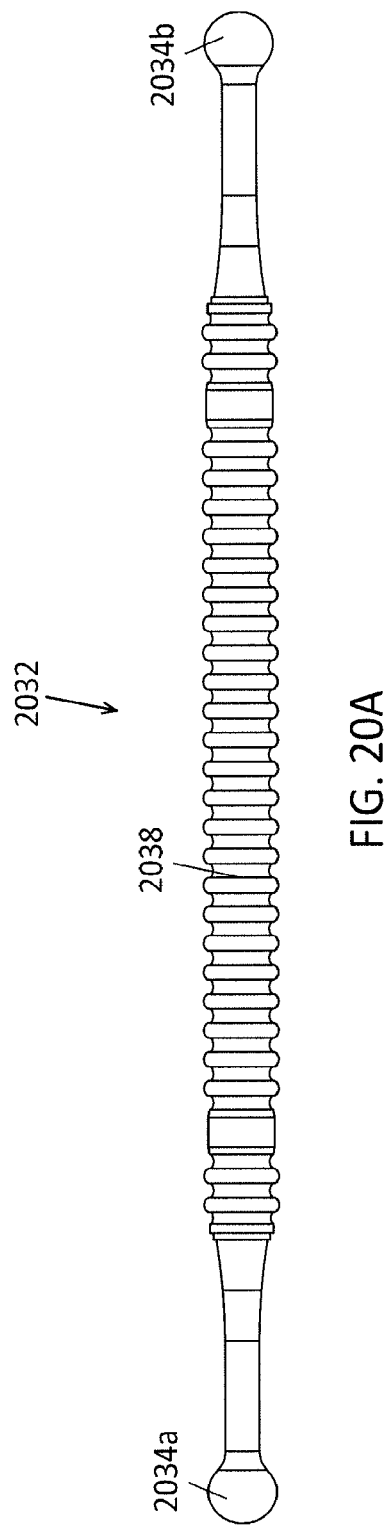
FIG. 20A shows a nasal implant with two rounded atraumatic ends.
Figure 20B:
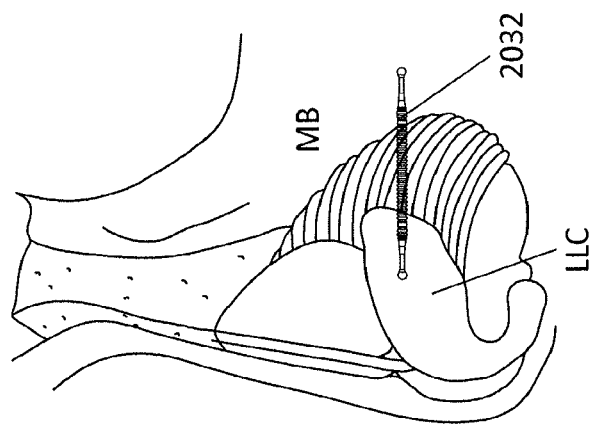
FIG. 20B shows the implant of FIG. 20A positioned within the nasal anatomy.

In some embodiments, the nasal implant may not include forked arms. For example, FIG. 20A illustrates a nasal implant 2032 with a central body 2038 and two rounded atraumatic ends 2034A,b instead of a single rounded atraumatic end and another end having arms or forks. FIG. 20B illustrates an example of how the nasal implant 2032 can be implanted relative to the nasal anatomy to support the nasal valve. As shown in FIG. 20B, the nasal implant 2032 is implanted with one rounded end 2034*a* in the lower lateral cartilage (LLC) and the other rounded end 2034*b* of the nasal implant is adjacent to the maxilla bone (MB).

In some embodiments, the forked arms of the implants can have sharpened edges.

Figure 53A:
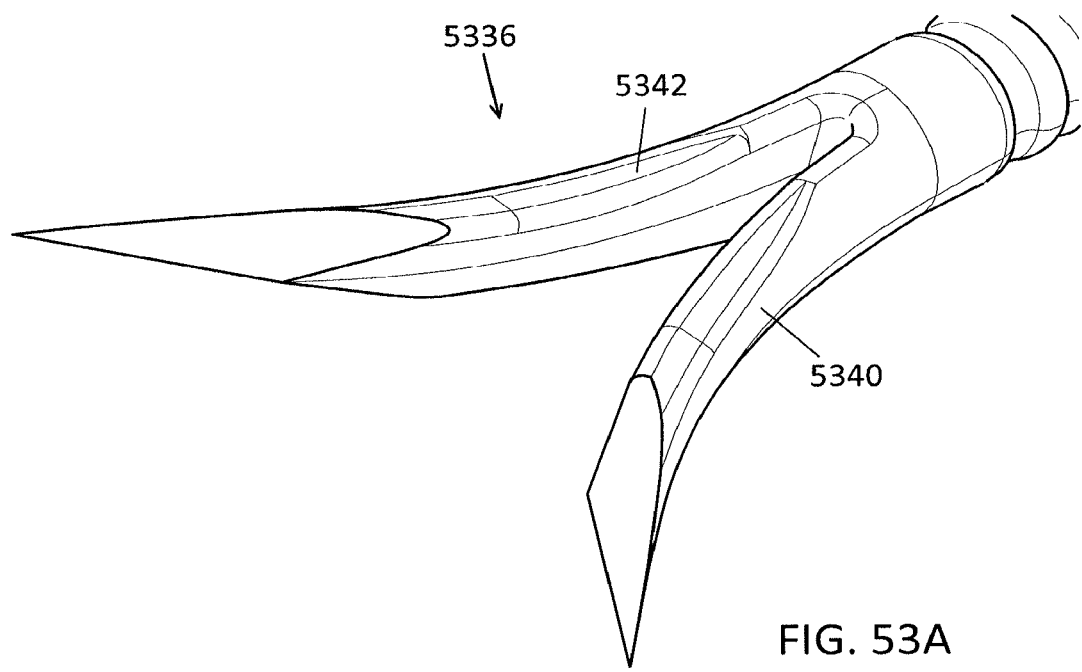
FIGS. 53A-53B show a forked distal end of a nasal implant that includes sharp faceted tips on the arms.
Figure 53B:
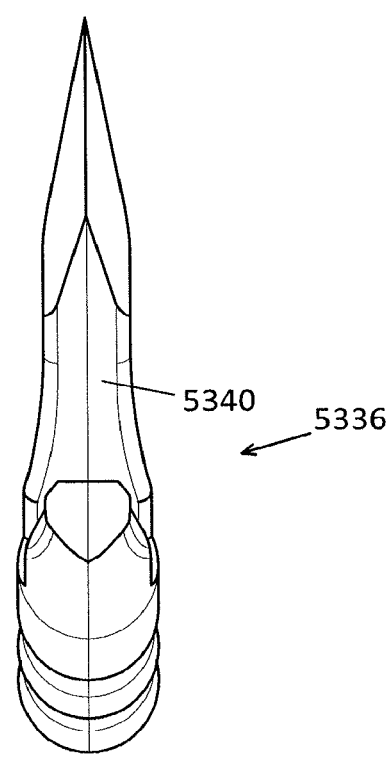

For example, FIGS. 53A-53B illustrate an embodiment of a forked distal end 5336 of a nasal implant. Each of the arms 5342, 5340 of the distal end 5336 includes a sharp faceted tip that is sharpened to facilitate tissue piercing and separation for tissue in or adjacent to the nasal tissue, such as mucosa and cartilage. The faceted tip design shown in FIGS. 53A-53B can be used in any of the nasal implants described herein. The faceted tip design can be formed by molding a beveled cutting tip into the fork tines. The facets are on the parting line plane of the part thereby facilitating ease of molding. The design can improve the piercing and slicing of soft tissue, which can reduce piercing and fixation forces used to deliver the implant to the targeted tissue. The outward angle of the bevels can also enhance the spreading of the arms for the expanded configuration during deployment.

Figure 54A:
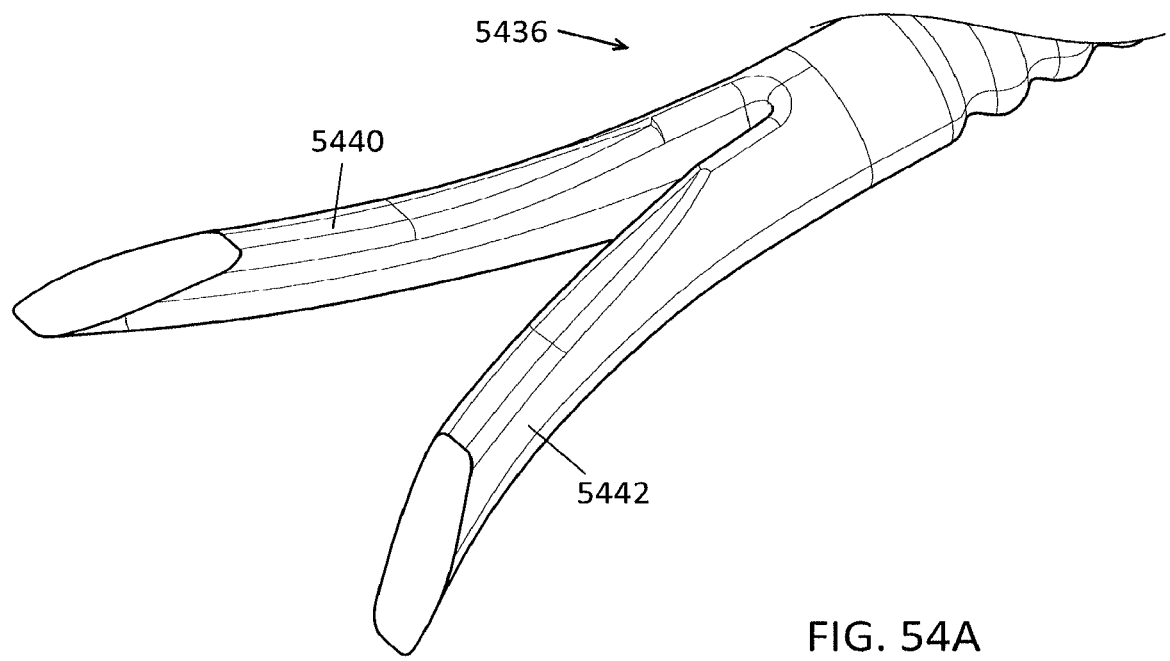
FIGS. 54A-54B show another forked distal end of a nasal implant that includes sharp faceted tips on the arms.
Figure 54B:
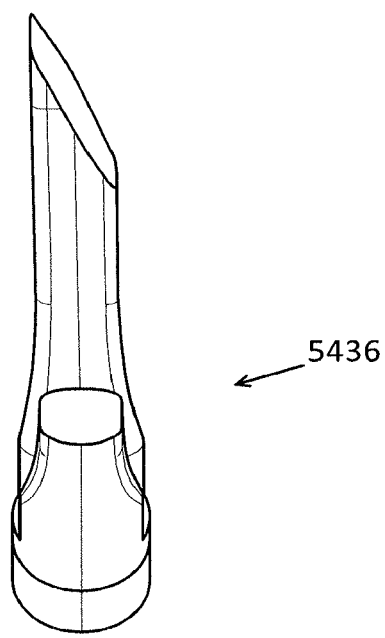

As another example, FIGS. 54A-54B illustrates an embodiment of a forked distal end 5436 of a nasal implant. Each arm 5442, 5440 includes a faceted tip having a 30 degree angle cut, which can help reduce piercing force. The faceted tip design shown in FIGS. 54A-54B can be used in any of the nasal implants described herein. The design shown in FIGS. 54A-54B can be formed by cutting the arm of the fork at a 30 degree angle from the parting line plane in one direction. The cutting process can cut off a portion of the bridge as well as the tines. In embodiments that use a circular cut made by a trimming fixture, the resulting tips shown in FIG. 54 can form points with two flat facets and one rounded surface. The single angle also provides the potential benefit of biasing the direction of the arms 5440, 5442 towards the nasal bone, which can potentially prevent the forks from piercing the patient's skin.

In some embodiments, the arms of the nasal implants can be axially offset from one another.

Figure 55A:
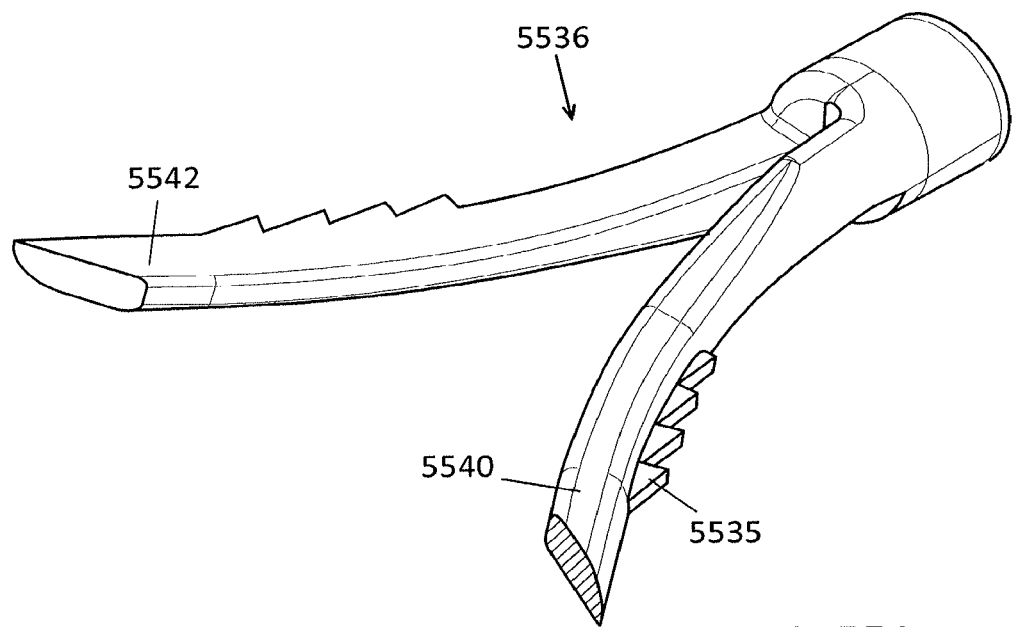
FIGS. 55A-55B show a forked distal end of a nasal implant in which the arms are offset from one another.
Figure 55B:
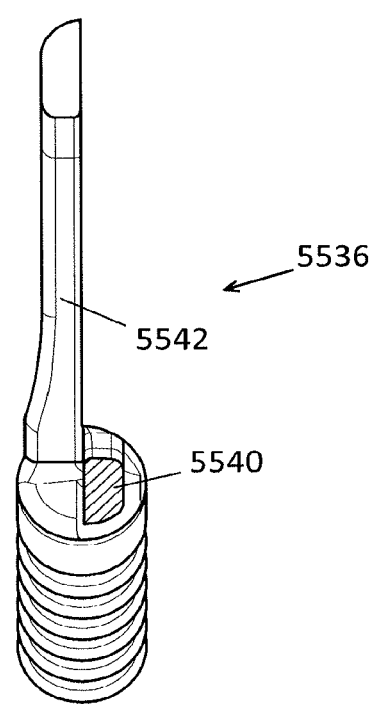

For example, FIGS. 55A-55B illustrate an embodiment of a forked distal end 5536 of a nasal implant with axially offset arms 5540, 5542. Each arm 5540, 5542 includes a faceted tip. Further, each of the arms 5540, 5542 include a plurality of teeth 5535 projecting outward. The offset arms 5540, 5542 can provide for a lower profile for the arms 5540, 5542 when the implant 5532 is in a compressed configuration. The design shown in FIG. 55 can be formed by molding the fork arms 5540, 5542 in an offset, scissor-like design, which enables the arms 5540, 5542 to fold completely inwards within the diameter of the implant profile. By enabling the complete folding of the fork arms 5540, 5542, a plurality of outward facing teeth can be added without adding to the overall profile of the implant 5532 in the compressed configuration, as an increase in the implant profile would increase drag within the cannula. The facets at the distal ends of the arms 5540, 5542 can also enhance piercing into soft tissue.

In some embodiments, the nasal implants described herein can be delivered to the targeted anatomy using a delivery tool with a hollow needle or cannula. The delivery tool can pierce the patient anatomy to locate the tip of the hollow needle or cannula adjacent to the targeted tissue. The hollow needle or cannula can be used to advance the nasal implant in the delivery configuration (e.g. compressed configuration). The nasal implant can be placed by pushing the nasal implant out of the needle, by withdrawing the needle relative to the implant, or combinations thereof. The hollow needle or cannula can have an orientation feature, like a non-circular cross-section, to control the orientation of the nasal implant so that the expanded configuration of the first arm and second arm of the implant can be deployed with the desired placement and orientation relative to the targeted tissue. Examples of delivery tools and delivery methods for orienting and delivering the nasal implant to the targeted tissue are described in U.S. application Ser. No. 15/274,986 titled "Nasal Implants and Systems and Method of Use" and U.S. 2016/0058556, the disclosures of each of which are incorporated by reference in their entirety.

In some variations, the implants described herein can have a relatively low profile (e.g., short height) in at least one dimension (length, width, height). The implant height can be, for example, less than 1 mm, less than 2 mm, less than 3 mm, less than 4 mm, less than 5 mm, less than 10 mm, less than 20 mm, or any size in between these, e.g., from 1 mm to 2 mm, from 1 to 5 mm, from 2 mm to 4 mm, etc. A low profile implant may be particularly beneficial, for example, because it may be inserted through a relatively small implant hole that heals easily, it may be the desired shape to fit anatomy of the space into which it is implanted, and/or it may not be obviously visible when implanted. The implant height may be chosen based on the implant environment and desired effect of the implant. For example, in the face and nose, underlying cartilage and bone generally determine face and nose shape, though muscle and skin play a role as well. The muscle, skin and associated tissues that cover the underlying cartilage and bone tend to take on the shape of the underlying structure that they cover. Skin and muscle thickness vary between individuals. Some people have relatively thicker skin and muscle and others have thinner skin and muscle. A relatively tall implant located over cartilage or bone may cause an obvious bump or protrusion in overlying thin muscle and skin that may be noticeable simply by looking at the person who may feel uncomfortable or self-conscious due to the attention, but may not cause an obvious bump or protrusion in a person with thicker muscle and skin which may better accommodate or mask the implant. An implant with a relatively small height may create a relatively low profile that is not obvious through the skin when the implant is in place in the nose. A low profile implant may, in some cases, make a small bump or protrusion that is detectable by close inspection or palpation. A body of the implant may be curved or bent (and may have various features that are not straight), but in general can be relatively straight and able to bend or flex. For example, the implant may flex to a minimum bend radius of 15 mm+/−0.5 mm.

An implant as described herein may be made of any biocompatible material that provides the desired support and shaping properties of the implant. The implant may be partially or wholly made from a non-biodegradable material as known in the art such as any polymer, metal, or shape memory material. The implant may be made from organic and/or inorganic materials. The material of the implant may be solid, (e.g. titanium, nitinol, or Gore-tex), braided or woven from a single material (such as titanium, or Polyethylene Terephthalate, or a combination of materials). If made of a woven material, the woven material may have pores that allow ingrowth of tissue after implantation. Representative synthetic polymers include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyacrylamides, polyorthoesters, polypheazenes, polysiloxanes, polyurethanes, polyvinyl alcohols, polyvinyl esters, polyvinyl ethers, polyvinyl halides, polyvinylpyrrolidone, poly(ether ketone)s, silicone-based polymers and blends and copolymers of the above.

Specific examples of these broad classes of polymers include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyurethane, poly(lactic acid), poly(butyric acid), poly(valeric acid), poly[lactide-coglycolide], poly(fumaric acid), poly(maleic acid), copolymers of poly (caprolactone) or poly (lactic acid) with polyethylene glycol and blends thereof.

A polymer used in the implants described herein may be non-biodegradable. Examples of non-biodegradable polymers that may be used include ethylene vinyl acetate (EVA), poly(meth)acrylic acid, polyamides, silicone-based polymers and copolymers and mixtures thereof.

In some embodiments, the implant can include one or more bioabsorbable materials in combination with a non-absorbing material. For example, in some cases, at least one of the distal end, proximal end, or central body is composed of a core made of a non-absorbable or an absorbable material. The implant can then include an outer layer made of a different non-absorbable or absorbable material from the core. In some examples, the core and outer layer are fixedly laminated to one another. In other examples, the core and outer layer are slid-ably engaged with one another.

In some embodiments, the first and second arms of the implant are configured to self-expand toward the deployed configuration. In some embodiments, the first and second arms of the implant are configured to move to the deployed configuration through engagement with tissue or part of the delivery tool.

For example, an implant or arms or features on an implant may include shape memory material. In some variations, an implant includes a biocompatible, bioabsorbable material such as a bioabsorbable polymer. A bioabsorbable or biodegradable implant may provide structure and support to a body tissue, such as nasal tissue, for a temporary period of time and may induce or cause the formation of scar or other tissue that provides structure and support to the body tissue for a longer period of time, including after the implant is degraded. Biologically formed scar or other tissue may be beneficial because it may be more comfortable, provide longer term support, stay in place better, etc. than does an implant. Part or all of an implant may be degradable in vivo (also referred to as biodegradable) into small parts and may be bioabsorbable. An implant or implant body may consist essentially of a bioabsorbable material. An implant or implant body may include two or more than two different bioabsorbable materials. A method as described herein may include biodegrading and bioabsorbing an implant or just part of an implant if an implant includes both bioabsorbable and non-bioabsorbable parts. Bioabsorbing may be facilitated by tissues and organs. Tissues and organs that bioabsorb may include bodily fluids, such as blood, lymph, mucus, saliva, etc. Bacteria may also aid in bioabsorbing a material. An implant may be partially or wholly made from one or more biocompatible biodegradable material, such as from a naturally occurring or synthetic polymer. A biodegradable implant may be made from a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof. In some examples, an implant includes poly-L-lactic acid (PLLA)), poly-D-lactic acid (PDLA), poly-D,L-lactic acid (PLDLLA) or a combination of two. In some examples, an implant is 90:10, 80:20, 70:30, 60:40, 50:50 PLLA/PDLA copolymer or is in between any of these values. In some examples, an implant is 70:30, +/−10% PLLA/PDLA copolymer. In some examples, an implant is 70:30, +/−10% PLLA/PDLLA.

An implant as described herein may include additional materials, such as an antibiotic, another antibacterial agent, an antifungal agent, an antihistamine, an anti-inflammatory agent, a cartilage growth inducer, a decongestant, a drug, a growth factor, microparticles, a mucolytic, a radiopaque material, a steroid, a vitamin, etc. Such materials may be attached to, adhered to, coated onto, or incorporated into to an implant. Such materials may be inserted into a body tissue along with the implant. Such materials may be required at different times and may be time sensitive or time release. For example, an anti-inflammatory agent may be useful immediately after implantation to prevent too much early inflammation and pain, but may not be desirable during later stages of scar formation and healing as it may interfere with a healing process that provides new tissue to provide support for tissues once the implant is remove. For example, an implant may be configured to release a cartilage growth inducer, such as a fibroblast growth factor (FGF; such as basic fibroblast growth factor or FGF2) or a transforming growth factor (TGF; such as TGFβ1) after several days or weeks so as to prevent an inappropriate or unwanted response early on.

The implants disclosed herein can include multiple materials to tailor the stiffness of the implant, outer hardness/softness, biocompatibility, and absorption profile of the implant. In some embodiments the implants can include an inner structure that is degradable with an outer coating that is hydrophobic. The degradable material can degrade in vivo through hydrolysis. Degradation can be slowed by coating the degradable material with a coating, such as a hydrophobic coating to control or tune the degradation of the implant. The hydrophobic coating can delay ingress of water and subsequently delay hydrolysis of the degradable portion of the implant. An example of a hydrophobic material that can be used is polycaprolactone, which is an absorbable material that is hydrophobic, crystalline, and highly elastic making it well suited for a coating. The coating can be applied with a specifically selected blend of solvents to minimize the impact on the underlying polymer structure. In some embodiments, a non-absorbable biocompatible coating, such as a silicone, an epoxy acrylate, or Parylene™ could be used to slow the absorption of water into the underlying polymer.

The biodegradation rate, profile, and/or period of the implant can be tuned. For example, a multitude of coatings both absorbable and non-absorbable can be applied to an underlying implant structure that already exhibits the necessary mechanical properties for supporting upper and lower lateral nasal cartilage. Many possible coatings exist including polycaprolactone, silicone, fluoropolymers, vinyl alcohol, acrylates, etc. In some embodiments the coating can be Parylene™. An exemplary hydrophobic coating compound, Parylene™ (poly(dichloro-para-xylylene)) has the forms:

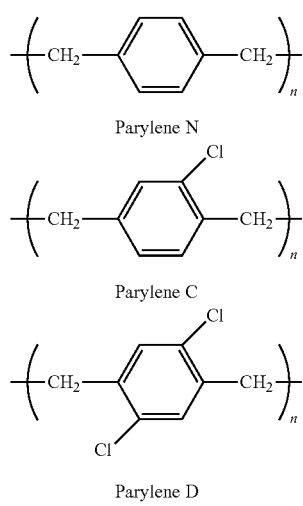

Parylene N

Parylene C

Parylene D

Parylene™ N is the basic member of the family and is typically most permeable to moisture. Parylene™ C and D are typically used for moisture barrier properties. Existing forms of Parylene™ have been primarily used as a complete moisture barrier for electronics and medical implants due to typically pinhole free coating properties. In some cases Parylene™ can be used as a control release agent for drugs being released out of a material below the coating. For example, the drug can be in a layer or material beneath the Parylene™ coating. In other forms of coatings, Parylene™ can also be used for adding lubricious coatings on guidewires and catheters. In the present disclosure Parylene™ is used differently than the traditional applications. In one embodiment, the semi-permeable nature of extremely thin coating layers can be used advantageously to control water ingress through the thin coating and into contact with the underlying implant structure. The biodegradation rate of the implant can be controlled by selecting and controlling the thicknesses and conformality of the coating, such as a Parylene™ coating.

The conformal coating process for Parylene™ can allow for controlling the thickness of the coat on the implant substrate. In order to facilitate some water transmission through the Parylene™ coating and initiate hydrolytic degradation, the implant may be coated at thicknesses in the range of about 0.1 to about 10 microns, preferably in the range of 0.1 to 5 micron to allow for a semi-permeable design. The design of a semi-permeable coat achieves selective tuning of the absorption rate of the implant, where the extent of permeation is determined by the coating thickness and conformality.

The thickness of the hydrophobic coating can be selected to modify the absorption profile of the implant. In some embodiments the thickness of the hydrophobic coating can be from about 0.1 micron to about 10 microns. In some embodiments the thickness of the hydrophobic coating can be from about 0.1 micron to about 5 microns. In some embodiments the thickness of the hydrophobic coating can be from about 0.1 micron to about 1 micron. In some embodiments the hydrophobic coating has a thickness of less than 10 microns. In some embodiments the hydrophobic coating has a thickness of less than 5 microns. In some embodiments the hydrophobic coating has a thickness of less than 1 micron. The thickness of the coating can be selected to control the rate of water ingress through the coating and into the core of the implant.

The hydrophobic coating can be applied to the entire outer surface of the implant or portions of the outer surface of the implant. In some embodiments the hydrophobic coating is applied to a central rod portion of the implant. In another embodiment the hydrophobic coating is applied to the implant except for the ends. For example, the proximal end or tip can be uncoated to act as a site for water ingress.

The conformality of the hydrophobic coating can also be selected to modify the absorption profile of the implant. In some embodiments, the conformality of the hydrophobic coating is selected to control the rate of water ingress through the hydrophobic coating and into the core of the implant. In some embodiments, the hydrophobic coating has a patterned conformality with coated sections and open sections. The patterned hydrophobic coating can be applied over the entire outer surface of the implant or on portions of the implant. In some embodiments the hydrophobic coating can have a porous structure.

In some embodiments the hydrophobic coating can have a laminated structure made out of multiple materials. For example, a combination of bioabsorbable layers and non-bioabsorbable layers can be used in some embodiments to tune the degradation rate or profile of the implant after implantation in the nasal tissue. The coatings can be applied using a variety of processes, such as vapor deposition, dip coating, spray coating, sputter coating, brush layering, etc.

In some embodiments, the hydrophobic coating is bioabsorbable. In the case of polycaprolactone, the coating itself is hydrophobic and bioabsorbable allowing for complete resorption over time. Using a dip coating method, a coating thickness of 0.1 to 10 microns can be achieved for desired results. Additionally, the same effect can be achieved by depositing 0.001 to 20 weight percent of polycaprolactone on the implant substrate. Polycaprolactone is dissolved readily in a mixture of various solvents consisting of but not limited to cycloalkanes, organic esters, chloroform and other such organic solvents.

The implants described herein can have an outer diameter of 0.5 mm-1.5 mm, such as approximately 1 mm.

The degradation profile rate of the implants described herein can be selectively tuned such that the life of the implant core or implant base polymeric substrate can be increased up to 20-fold.

In some embodiments, the delivery device used to implant the nasal implants described herein can include a needle with a non-circular cross-section, such as an oval in one example, to accommodate tissue ingrowth features and/or acute tissue attachment features of the implant.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A nasal implant comprising:
   a body portion having a proximal end, a distal end, a lateral side, a medial side, and a central portion along a length of the body portion between the lateral side and the medial side, wherein the body portion comprises a plurality of undulations along the lateral side and the medial side;
   a first arm disposed at the distal end, the first arm having a proximal end fixed to the distal end of the body portion and a distal end not fixed to the body portion, the distal end of the first arm being adapted to move away from a central longitudinal axis of the body portion from a delivery configuration toward a deployed configuration;
   a second arm having a proximal end fixed to the distal end of the body portion and a distal end not fixed to the body portion, the distal end of the second arm being adapted to move away from a central longitudinal axis of the body portion from a delivery configuration toward a deployed configuration; and
   a plurality of openings in the central portion along the length of the body portion,
   wherein the plurality of openings are adapted to allow tissue ingrowth.

2. The nasal implant of claim 1,
   wherein each of the plurality of openings is in a shape of a pointed oval.

3. The nasal implant of claim 1, wherein each of the plurality of openings comprises a through-hole that extends entirely through a thickness of the body portion.

4. The nasal implant of claim 3, wherein the plurality of openings decrease in diameter from the distal end towards the proximal end.

5. The nasal implant of claim 1, further comprising a coating on the body portion that is adapted to control a biodegradation rate of the body portion.

6. The nasal implant of claim 5, wherein the coating comprises parylene.

7. The nasal implant of claim 1, wherein the first arm and the second arm each comprise a grooved window that is recessed from an exterior surface of the first arm and the second arm.

8. The nasal implant of claim 7, further comprising a plurality of barbs in the grooved window of the first arm and the second arm.

9. A nasal implant comprising:
a body portion having a proximal end and a distal end;
a first arm disposed at the distal end, the first arm having a proximal end fixed to the distal end of the body portion and a distal end not fixed to the body portion, the distal end of the first arm being adapted to move away from a central longitudinal axis of the body portion from a delivery configuration toward a deployed configuration; and
a second arm having a proximal end fixed to the distal end of the body portion and a distal end not fixed to the body portion, the distal end of the second arm being adapted to move away from a central longitudinal axis of the body portion from a delivery configuration toward a deployed configuration,
wherein the body portion further comprises a plurality of tissue ingrowth features that extend outwardly from the body portion, and
wherein each tissue ingrowth feature comprise at least one feature selected from a group of: a web or a flap,
wherein each tissue ingrowth feature comprises a tip that has at least one characteristic selected from a group consisting of: (i) hollow and (ii) annular.

10. The nasal implant of claim 9, wherein the tip of each tissue ingrowth feature is hollow.

11. The nasal implant of claim 9, wherein the tip of each tissue ingrowth feature is annular.

12. The nasal implant of claim 9, wherein each tissue ingrowth feature extends outwardly and proximally from the body portion.

13. The nasal implant of claim 9, further comprising a coating on the body portion that is adapted to control a biodegradation rate of the body portion.

14. A method of forming a nasal implant comprising:
forming a body portion having a proximal end, a distal end, a lateral side, a medial side, and a central portion along a length of the body portion between the lateral side and the medial side, wherein the body portion comprises a plurality of undulations along the lateral side and the medial side;
forming a first arm disposed at the distal end, the first arm having a proximal end fixed to the distal end of the body portion and a distal end not fixed to the body portion, the distal end of the first arm being adapted to move away from a central longitudinal axis of the body portion from a delivery configuration toward a deployed configuration;
forming a second arm having a proximal end fixed to the distal end of the body portion and a distal end not fixed to the body portion, the distal end of the second arm being adapted to move away from a central longitudinal axis of the body portion from a delivery configuration toward a deployed configuration; and
forming a plurality of openings in the central portion along the length of the body portion,
wherein the plurality of openings are adapted to allow tissue ingrowth.

15. The method of claim 14, wherein each of the plurality of openings is in a shape of a pointed oval.

16. The method of claim 14, wherein each of the plurality of openings comprises a through-hole that extends entirely through a thickness of the body portion.

17. The method of claim 14, wherein the plurality of openings decrease in diameter from the distal end towards the proximal end.

18. The nasal implant of claim 14, wherein the first arm and
the second arm each comprise a grooved window that is recessed from an exterior surface of the first arm and the second arm.

19. The nasal implant of claim 18, further
comprising a plurality of barbs in the grooved window of the first arm and the second arm.

20. The nasal implant of claim 14, further comprising
applying a coating on the body portion that is adapted to control a biodegradation rate of the body portion.

* * * * *